_United States Patent_ [19]

Kimura et al.

[11] Patent Number: 5,610,303

[45] Date of Patent: Mar. 11, 1997

[54] ARYLAMINO PYRIMIDINE COMPOUND

[75] Inventors: Tomio Kimura, Niiza; Yoshiaki Kuroki, Ube; Hiroshi Fujiwara, Ube; Shigeharu Anpeiji, Ube, all of Japan

[73] Assignee: Ube Industries, Ltd., Ube, Japan

[21] Appl. No.: 411,838

[22] PCT Filed: Oct. 1, 1993

[86] PCT No.: PCT/JP93/01412

§ 371 Date: Apr. 3, 1995

§ 102(e) Date: Apr. 3, 1995

[87] PCT Pub. No.: WO94/07890

PCT Pub. Date: Apr. 14, 1994

[30] Foreign Application Priority Data

Oct. 5, 1992 [JP] Japan .................................... 4-266353

[51] Int. Cl.$^6$ ............................................ C07D 401/10
[52] U.S. Cl. .......................... 544/326; 544/253; 544/284; 544/298; 544/329
[58] Field of Search ................................. 544/253, 298, 544/326, 329, 284

[56] References Cited

U.S. PATENT DOCUMENTS

| 4,450,162 | 5/1984 | Kamioka et al. | 544/326 |
| 4,895,841 | 1/1990 | Sugimoto et al. | 514/212 |
| 5,100,901 | 3/1992 | Sugimoto et al. | 514/319 |
| 5,177,087 | 1/1993 | Goto et al. | 544/360 |

FOREIGN PATENT DOCUMENTS

| 0067630 | 5/1985 | European Pat. Off. . |
| 0378207 | 7/1990 | European Pat. Off. . |
| 57-203072 | 12/1982 | Japan . |
| 3-173867 | 7/1991 | Japan . |

_Primary Examiner_—Yogendra N. Gupta
_Attorney, Agent, or Firm_—Frishauf, Holtz, Goodman, Langer & Chick, P.C.

[57] ABSTRACT

A pyrimidine derivative represented by the formula (II) or (III):

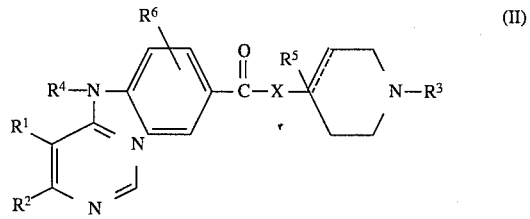

(II)

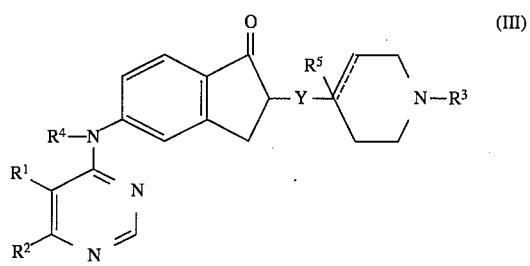

(III)

(wherein $R^1$ and $R^2$ each represent H, a halogen, amino, nitro, an unsubstituted or substituted alkyl, an alkoxy or an alkoxycarbonyl, or $R^1$ and $R^2$ are bonded together to form an unsubstituted or substituted alkylene; $R^3$ represents an aralkyl or a hetero aromatic ring type-alkyl, $R^4$ represents H or acyl, $R^5$ represents H, OH or an alkoxy, $R^6$ represents H, a halogen, an alkyl or an alkoxy, X represents —CH=, —CH=CH—$(CH_2)_p$—, —CH$_2$— or —CH$_2$CH$_2$—$(CH_2)_p$—, Y represents =CH— $(CH_2)_p$—, —CH$_2$—$(CH_2)_p$—, a single bond or a double bond, p represents 0 or 1, and . . . represents a single bond or a double bond), and a salt thereof have selective acetylcholinesterase-inhibiting activities and selective A type monoamine oxidase-inhibiting activities, and are useful as an antidepressant and an agent for curing senile dementia.

21 Claims, No Drawings

ARYLAMINO PYRIMIDINE COMPOUND

TECHNICAL FIELD

This invention relates to a pyrimidine derivative having both of an excellent selective acetylcholinesterase-inhibiting activity and an excellent selective A type monoamine oxidase-inhibiting activity and useful as an antidepressant and an agent for curing senile dementia, and a salt thereof.

BACKGROUND ART

In senile dementia, acetylcholine in a brain is lacking so that an acetylcholinesterase-inhibiting agent has been studied. For example, as an agent for curing dementia, there have been disclosed 1-benzyl-4-[(5,6-dimethoxy-1-indanon)-2-yl]methylpiperidine, etc. in Japanese Provisional Patent Publication No. 79151/1989 and 1-benzyl-4-[2-(4pyrrolidinobenzoyl)ethyl]piperidine, etc. in Japanese Provisional Patent Publication No. 173867/1991 (U.S. Pat. No. 5,177, 087). However, senile dementia is generally accompanied with symptoms such as depression, lowering of volition, etc. so that various symptoms of senile dementia cannot be ameliorated sufficiently only by an acetylcholinesterase-inhibiting agent. On the other hand, depression is related to monoamine (noradrenaline, serotonin), and as an antidepressant having an A type monoamine oxidase-inhibiting activity, there has been known, for example, 4-(4-cyanoanilino)-5,6-dihydro-7H-cyclopenta[d]pyrimidine as disclosed in Japanese Provisional Patent Publication No. 203072/1982 (U.S. Pat. No. 4,450,162).

The present inventors have studied for many years in order to develop a medicine having both of a selective acetylcholinesterase-inhibiting activity and a selective A type monoamine oxidase-inhibiting activity and therefore having a further improved curing effect as an agent for curing senile dementia, and consequently found that a pyrimidine derivative having a specific structure with selective inhibiting activities to both enzymes, to accomplish the present invention.

DISCLOSURE OF THE INVENTION

The present invention is a pyrimidine derivative represented by the formula (I):

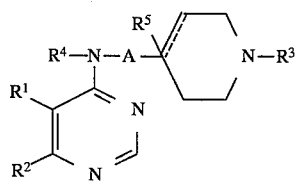

(wherein $R^1$ and $R^2$ each represent a hydrogen atom, a halogen atom, an amino group, a nitro group, an alkyl group, a lower alkoxy group or a lower alkoxycarbonyl group, or $R^1$ and $R^2$ are bonded together to form an alkylene group, and said alkyl group and alkylene group may be substituted by a halogen, hydroxy, a lower alkoxy, a lower alkenyloxy, an aryloxy, an aralkyloxy or an acyloxy.

$R^3$ represents an aralkyl group or a hetero aromatic ring type-alkyl group and the aryl portion of said aralkyl group and the hetero aromatic ring portion of the hetero aromatic ring type-alkyl group may be substituted by a halogen, amino, alkanoylamino, cyano, nitro, hydroxy, a lower alkyl, a lower alkoxy, an aralkyloxy, an alkylenedioxy, a halogeno-lower alkyl or a halogeno-lower alkoxy.

$R^4$ represents a hydrogen atom or an acyl group.

$R^5$ represents a hydrogen atom, a hydroxy group or a lower alkoxy group.

A represents

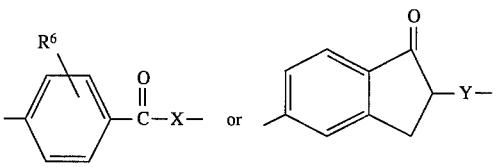

where $R^6$ represents a hydrogen atom, a halogen atom, a lower alkyl group or a lower alkoxy group, X represents —CH=, —CH=CH—$(CH_2)_p$—, —$CH_2$— or —$CH_2CH_2$—$(CH_2)_p$—, Y represents =CH—$(CH_2)_p$—, —$CH_2$—$(CH_2)_p$—, a single bond or a double bond and p represents 0 or 1.

Also, $\overline{\cdots}$ represents a single bond or a double bond, and when $\cdots$ represents a double bond or X represents —CH=, or Y represents a double bond, $R^5$ does not exist) and a salt thereof.

The compounds represented by the above formula (I) are roughly classified into compounds represented by the following formula (II) and formula (III):

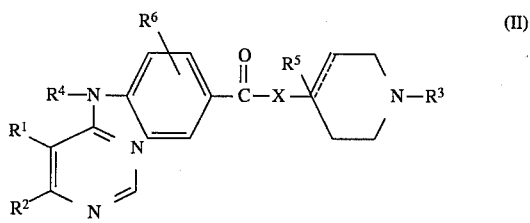

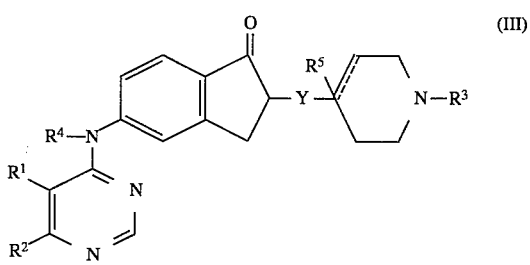

(wherein $R^1$, $R^2$, $R^3$, $R^4$, $R^5$, $R^6$, X, Y and $\overline{\cdots}$ have the same meanings as defined above)

As the halogen atom of $R^1$ and $R^2$, there may be mentioned fluorine, chlorine, bromine and iodine; as the alkyl group, there may be mentioned a $C_{1-10}$ straight or branched alkyl group such as methyl, ethyl, propyl, isopropyl, butyl, isobutyl, sec-butyl, t-butyl, pentyl, hexyl, heptyl, octyl, nonyl and decyl; as the lower alkoxy group, there may be mentioned a $C_{1-4}$ straight or branched lower alkoxy group such as methoxy, ethoxy, propoxy, isopropoxy, butoxy, isobutoxy, sec-butoxy and t-butoxy; as the lower alkoxycarbonyl group, there may be mentioned a $C_{2-5}$ atkoxycarbonyl group such as methoxycarbonyl, ethoxycarbonyl, propoxycarbonyl, isopropoxycarbonyl, butoxycarbonyl, isobutoxycarbonyl, sec-butoxycarbonyl and t-butoxycarbonyl; and as the alkylene group formed by bonding $R^1$ and $R^2$ together, there may be mentioned a $C_{3-6}$ straight or branched alkylene group such as trimethylene, 1-, 2- or 3-methyltrimethylene, 1,2-dimethyltrimethylene, 2,2-dimethyltrimethylene, 1,3-dimethyltrimethylene, tetramethylene, 1- or 2-methyltetramethylene and 1,2-dimethyltetramethylene.

The above alkyl group and alkylene group may have a substituent(s). As said substituent, there may be mentioned a halogen atom such as fluorine, chlorine, bromine and iodine; a hydroxy group; a $C_{1-4}$ straight or branched lower alkoxy group such as methoxy, ethoxy, propoxy, isopropoxy, butoxy, isobutoxy, sec-butoxy and t-butoxy; a $C_{3-4}$ lower alkenyloxy group such as allyloxy and 2-butenyloxy; an aryloxy group such as phenoxy and naphthoxy; an aralkyloxy group such as benzyloxy and phenethyloxy; a $C_{1-10}$ aliphatic acyloxy group such as formyloxy, acetyloxy, propionyloxy, butyryloxy, isobutyryloxy, valeryloxy, isovaleryloxy, pivaloyloxy, hexanoyloxy, heptanoyloxy, octanoyloxy, nonanonyloxy and decanoyloxy; an aromatic aliphatic acyloxy group such as phenylacetoxy and cinnamoyloxy; and an aromatic acyloxy group such as benzoyloxy and naphthoyloxy.

As the groups of $R^1$ and $R^2$, preferred are a hydrogen atom, a fluorine atom, a chlorine atom, a bromine atom, a $C_{1-7}$ straight or branched alkyl group, a trimethylene group, a tetramethylene group and a 2,2-dimethyltrimethylene group, and as the group having a substituent(s), preferred are a hydroxymethyl group, a fluoromethyl group, a chloromethyl group, a bromomethyl group, a methoxymethyl group, a phenoxymethyl group, a benzyloxymethyl group, an acetoxymethyl group, a propionyloxymethyl group, a benzoyloxymethyl group, a 1- or 2-hydroxyethyl group, a 1- or 2-fluoroethyl group, a 1- or 3-hydroxytrimethylene group, a 1- or 3-fluorotrimethylene group, a 1- or 3-chlorotrimethylene group, a 1- or 3-bromotrimethylene group, a 1- or 3-methoxytrimethylene group, a 1- or 3-phenoxytrimethylene group, a 1- or 3-acetoxytrimethylene group, a 1,3-dihydroxytrimethylene group and a 1,3-difluorotrimethylene group. As the groups of $R^1$ and $R^2$, particularly preferred are a hydrogen atom, a fluorine atom, a chlorine atom, a bromine atom, a methyl group, an ethyl group, a propyl group, an isopropyl group, a butyl group, a trimethylene group, a tetramethylene group and a 2,2-dimethyltrimethylene group, and as the group having a substituent(s), particularly preferred are a hydroxymethyl group, a fluoromethyl group, a methoxymethyl group, an acetoxymethyl group, a 1- or 3-hydroxytrimethylene group, a 1- or 3-fluorotrimethylene group, a 1- or 3-methoxytrimethylene group, a 1- or 3-acetoxytrimethylene group and a 1,3-difluorotrimethylene group. It is particularly preferred that $R^1$ and $R^2$ form a trimethylene group or a tetramethylene group in combination, or one is a $C_{1-4}$ alkyl group and the other is a hydrogen atom, a chlorine atom or a $C_{1-4}$ alkyl group, and most preferred is a compound wherein $R^1$ and $R^2$ form a trimethylene group in combination or $R^1$ is a $C_{1-4}$ alkyl group and $R^2$ is a hydrogen atom or a $C_{1-4}$ alkyl group.

As the aralkyl group of $R^3$, there may be mentioned an aryl $C_{1-4}$ alkyl group such as benzyl, phenethyl, sec-phenethyl, phenylpropyl, phenylbutyl, naphthylmethyl and diphenylmethyl; and as the hetero aromatic ring type-alkyl group, there may be mentioned a hetero aromatic ring type-$C_{1-4}$ alkyl group such as thienylmethyl, thienylethyl, thienylpropyl, thienylbutyl, furylmethyl, pyridylmethyl, pyrimidinylmethyl, thiazolylmethyl, oxazolylmethyl, imidazolylmethyl, 2-benzothiazolylmethyl, 2-benzoxazolylmethyl and 2-benzoimidazolylmethyl. The aryl portion of the above aralkyl group and the hetero aromatic ring portion of the hetero aromatic ring type-alkyl group may have a substituent(s), and as said substituent, there may be mentioned a halogen atom such as fluorine, chlorine, bromine and iodine; a $C_{1-4}$ straight or branched lower alkyl group such as methyl, ethyl, propyl, isopropyl, butyl, isobutyl, sec-butyl and t-butyl; a $C_{1-4}$ straight or branched lower alkoxy group such as methoxy, ethoxy, propoxy, iso-propoxy, butoxy, isobutoxy, sec-butoxy and t-butoxy; an aralkyloxy group such as benzyloxy, phenethyloxy and naphthylmethoxy; an alkylenedioxy group such as methylenedioxy and ethylenedioxy; an amino group, a $C_{1-4}$ alkanoylamino such as formylamino, acetylamino, propionylamino, butyrylamino and isobutyrylamino; a nitro group; a cyano group; a hydroxy group; a $C_{1-4}$ halogeno-lower alkyl group such as fluoromethyl, chloromethyl, difluoromethyl, trifluoromethyl, 2-fluoroethyl, 2-chloroethyl, 2-bromoethyl, 2,2,2-trifluoroethyl, 3-fluoropropyl and 4-fluorobutyl; and a $C_{1-4}$ halogeno-lower alkoxy group such as fluoromethoxy, difluoromethoxy, trifluoromethoxy, 2-fluoroethoxy, 2-chloroethoxy, 2-bromoethoxy, 2,2,2-trifluoroethoxy, 3-fluoropropoxy and 4-fluorobutoxy.

As the group of $R^3$, preferred are a benzyl group, a sec-phenethyl group, a fluorobenzyl group, a methoxybenzyl group, an ethylenedioxybenzyl group, a hydroxybenzyl group, a chlorobenzyl group, a methylbenzyl group, a trifluoromethylbenzyl group, an aminobenzyl group, an acetylaminobenzyl group, a nitrobenzyl group, a cyanobenzyl group, a diphenylmethyl group, a di(4-fluorophenyl)methyl group, a thienylmethyl group, a furylmethyl group, a pyridylmethyl group, a methylpyridylmethyl group and a pyrimidinylmethyl group. As the group of $R^3$, particularly preferred are a benzyl group, a sec-phenethyl group, a 2-, 3- or 4-fluorobenzyl group, a 2-, 3- or 4-chlorobenzyl group, a 2-, 3- or 4-methoxybenzyl group, a 2-, 3- or 4-cyanobenzyl group, a 2-, 3- or 4-nitrobenzyl group, a 2-thienylmethyl group, a 2-furylmethyl group, a 2-pyridylmethyl group and a 6-methyl-2-pyridylmethyl group.

As the acyl group of $R^4$, there may be mentioned a $C_{1-10}$ aliphatic acyl group such as formyl, acetyl, propionyl, butyryl, isobutyryl, valeryl, isovaleryl, pivaloyl, hexanoyl, heptanoyl, octanoyl, nonanoyl and decanoyl; an aromatic aliphatic acyl group such as phenylacetyl and cinnamoyl; and an aromatic acyl group such as benzoyl and naphthoyl.

As the group of $R^4$, preferred are a hydrogen atom, a formyl group, an acetyl group, a propionyl group, a butyryl group and a pivaloyl group, and particularly preferred are a hydrogen atom and an acetyl group.

As the lower alkoxy group of $R^5$, the same lower alkoxy group mentioned in $R^1$ and $R^2$ may be mentioned.

As the group of $R^5$, preferred are a hydrogen atom, a hydroxy group, a methoxy group and an ethoxy group, and particularly preferred is a hydrogen atom.

As the halogen atom and the lower alkoxy group of $R^6$, the same halogen atom and lower alkoxy group mentioned in $R^1$ and $R^2$ may be mentioned; and as the lower alkyl group, there may be mentioned a $C_{1-4}$ straight or branched alkyl group such as methyl, ethyl, propyl, isopropyl, butyl, isobutyl and sec-butyl.

As the group of $R^6$, preferred are a hydrogen atom, a fluorine atom, a chlorine atom, a methyl group and a methoxy group, and particularly preferred are a hydrogen atom, a fluorine atom, a chlorine atom and a methoxy group.

As X in the formula (II), —CH=, —CH$_2$—, —CH$_2$CH$_2$— and —CH=CH— are particularly preferred. As Y in the formula (III), —CH$_2$— and =CH— are particularly preferred. The compound of the formula (II) is preferred for achieving the object of the present invention.

The ... is preferably a single bond.

The compounds of the formula (I), the formula (II) and the formula (III) may be converted into salts, if necessary. As a pharmaceutically acceptable salt, there may be mentioned a salt of a mineral acid such as hydrochloride, hydrobromide, hydroiodide, sulfate and phosphate; a sulfonate such as methanesulfonate, ethanesulfonate, benzenesulfonate and p-toluenesulfonate; oxalate, maleate, fumarate and tartrate; and an acid addition salt of an organic acid such as citrate. The compounds of the formula (I), the formula (II) and the formula (III) or salts thereof may exist as hydrates.

Examples of the compound of the formula (II) are shown in Table 1 (Compound II), and examples of the compound of the formula (III) are shown in Table 2 (Compound III), respectively.

TABLE 1

(Compound II)

| No. | $R^1$ | $R^2$ | $R^4$ | $R^6$ | X | 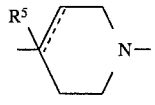 | $R^3$ |
|---|---|---|---|---|---|---|---|
| 1 | $-CH_2CH_2CH_2-$ | | H | H | $-CH_2-$ | 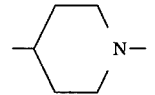 | benzyl |
| 2 | " | | " | " | $-(CH_2)_2-$ | " | " |
| 3 | " | | " | " | $-(CH_2)_3-$ | " | " |
| 4 | " | | " | " | $-CH=$ | 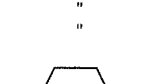 | " |
| 5 | " | | " | " | $-CH=CH-$ | 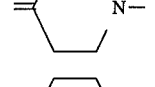 | " |
| 6 | " | | " | " | $-CH=CHCH_2-$ | " | " |
| 7 | " | | " | " | $-CH_2-$ | " | 4-fluoro-benzyl |
| 8 | " | | " | " | $-(CH_2)_2-$ | " | 4-fluoro-benzyl |
| 9 | " | | " | " | $-(CH_2)_3-$ | " | 4-fluoro-benzyl |
| 10 | " | | " | " | $-CH=$ | 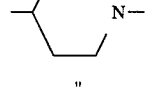 | 4-fluoro-benzyl |
| 11 | " | | " | " | $-CH=CH-$ |  | 4-fluoro-benzyl |
| 12 | " | | " | " | $-CH=CHCH_2-$ | " | 4-fluoro-benzyl |
| 13 | " | | " | " | $-CH_2-$ | " | 3-fluoro-benzyl |
| 14 | " | | " | " | $-(CH_2)_2-$ | " | 3-fluoro-benzyl |
| 15 | " | | " | " | $-(CH_2)_3-$ | " | 3-fluoro-benzyl |
| 16 | " | | " | " | $-CH=$ | 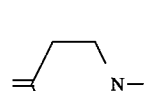 | 3-fluoro-benzyl |
| 17 | " | | " | " | $-CH=CH-$ | 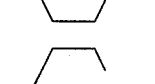 | 3-fluoro-benzyl |
| 18 | " | | " | " | $-CH=CHCH_2-$ | " | 3-fluoro-benzyl |
| 19 | $-CH_2CH_2CH_2-$ | | H | H | $-CH_2-$ | 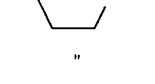 | 2-fluoro-benzyl |

TABLE 1-continued (Compound II)

| No. | R¹ | R² | R⁴ | R⁶ | X | $\overset{R^5}{\underset{}{\diagdown}}\hspace{-2pt}\text{N}-$ ring | R³ |
|---|---|---|---|---|---|---|---|
| 20 | | " | | " | " | —(CH₂)₂— | " | 2-fluoro-benzyl |
| 21 | | " | | " | " | —(CH₂)₃— | " | 2-fluoro-benzyl |
| 22 | | " | | " | " | —CH= | piperidinylidene | 2-fluoro-benzyl |
| 23 | | " | | " | " | —CH=CH— | piperidinyl | 2-fluoro-benzyl |
| 24 | | " | | " | " | —CH=CHCH₂— | " | 2-fluoro-benzyl |
| 25 | | " | | " | " | —CH₂— | " | 4-methoxy-benzyl |
| 26 | | " | | " | " | —(CH₂)₂— | " | 4-methoxy-benzyl |
| 27 | | " | | " | " | —(CH₂)₃— | " | 4-methoxy-benzyl |
| 28 | | " | | " | " | —CH= | piperidinylidene | 4-methoxy-benzyl |
| 29 | | " | | " | " | —CH=CH— | piperidinyl | 4-methoxy-benzyl |
| 30 | | " | | " | " | —CH=CHCH₂— | " | 4-methoxy-benzyl |
| 31 | | " | | " | " | —CH₂— | " | 3-methoxy-benzyl |
| 32 | | " | | " | " | —(CH₂)₂— | " | 3-methoxy-benzyl |
| 33 | | " | | " | " | —(CH₂)₃— | " | 3-methoxy-benzyl |
| 34 | | " | | " | " | —CH= | piperidinylidene | 3-methoxy-benzyl |
| 35 | | " | | " | " | —CH=CH— | piperidinyl | 3-methoxy-benzyl |
| 36 | | " | | " | " | —CH=CHCH₂— | " | 3-methoxy-benzyl |
| 37 | | " | | " | " | —CH₂— | " | 2-methoxy-benzyl |

TABLE 1-continued (Compound II)

| No. | $R^1$ | $R^2$ | $R^4$ | $R^6$ | X | ring | $R^3$ |
|---|---|---|---|---|---|---|---|
| 38 | $-CH_2CH_2CH_2-$ | | H | H | $-(CH_2)_2-$ | piperidine (saturated) | 2-methoxybenzyl |
| 39 | " | | " | " | $-(CH_2)_3-$ | " | 2-methoxybenzyl |
| 40 | " | | " | " | $-CH=$ | piperidine (=) | 2-methoxybenzyl |
| 41 | " | | " | " | $-CH=CH-$ | piperidine (saturated) | 2-methoxybenzyl |
| 42 | " | | " | " | $-CH=CHCH_2-$ | " | 2-methoxybenzyl |
| 43 | " | | " | " | $-CH_2-$ | " | 4-hydroxybenzyl |
| 44 | " | | " | " | $-(CH_2)_2-$ | " | 4-hydroxybenzyl |
| 45 | " | | " | " | $-(CH_2)_3-$ | " | 4-hydroxybenzyl |
| 46 | " | | " | " | $-CH=$ | piperidine (=) | 4-hydroxybenzyl |
| 47 | " | | " | " | $-CH=CH-$ | piperidine (saturated) | 4-hydroxybenzyl |
| 48 | " | | " | " | $-CH=CHCH_2-$ | " | 4-hydroxybenzyl |
| 49 | " | | " | " | $-CH_2-$ | " | 4-chlorobenzyl |
| 50 | " | | " | " | $-(CH_2)_2-$ | " | 4-chlorobenzyl |
| 51 | " | | " | " | $-(CH_2)_3-$ | " | 4-chlorobenzyl |
| 52 | " | | " | " | $-CH=$ | piperidine (=) | 4-chlorobenzyl |
| 53 | " | | " | " | $-CH=CH-$ | piperidine (saturated) | 4-chlorobenzyl |
| 54 | " | | " | " | $-CH=CHCH_2-$ | " | 4-chlorobenzyl |
| 55 | " | | " | " | $-CH_2-$ | " | 3-chlorobenzyl |
| 56 | " | | " | " | $-(CH_2)_2-$ | " | 3-chlorobenzyl |

TABLE 1-continued (Compound II)

| No. | R¹ | R² | R⁴ | R⁶ | X | $R^5$-piperidine | R³ |
|---|---|---|---|---|---|---|---|
| 57 | —CH₂CH₂CH₂— | | H | H | —(CH₂)₃— | 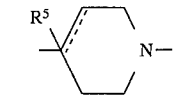 | 3-chlorobenzyl |
| 58 | " | | " | " | —CH= | 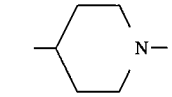 | 3-chlorobenzyl |
| 59 | " | | " | " | —CH=CH— | 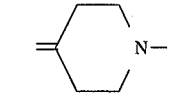 | 3-chlorobenzyl |
| 60 | " | | " | " | —CH=CHCH₂— | " | 3-chlorobenzyl |
| 61 | " | | " | " | —CH₂— | " | 2-chlorobenzyl |
| 62 | " | | " | " | —(CH₂)₂— | " | 2-chlorobenzyl |
| 63 | " | | " | " | —(CH₂)₃— | " | 2-chlorobenzyl |
| 64 | " | | " | " | —CH= |  | 2-chlorobenzyl |
| 65 | " | | " | " | —CH=CH— | 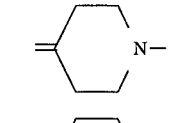 | 2-chlorobenzyl |
| 66 | " | | " | " | —CH=CHCH₂— | " | 2-chlorobenzyl |
| 67 | " | | " | " | —CH₂— | " | 4-methylbenzyl |
| 68 | " | | " | " | —(CH₂)₂— | " | 4-methylbenzyl |
| 69 | " | | " | " | —(CH₂)₃— | " | 4-methylbenzyl |
| 70 | " | | " | " | —CH= | 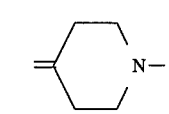 | 4-methylbenzyl |
| 71 | " | | " | " | —CH=CH— | 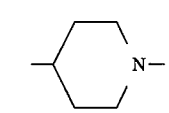 | 4-methylbenzyl |
| 72 | " | | " | " | —CH=CHCH₂— | " | 4-methylbenzyl |
| 73 | " | | " | " | —CH₂— | " | 4-nitrobenzyl |
| 74 | " | | " | " | —(CH₂)₂— | " | 4-nitrobenzyl |
| 75 | " | | " | " | —(CH₂)₃— | " | 4-nitrobenzyl |
| 76 | —CH₂CH₂CH₂— | | H | H | —CH= | 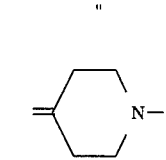 | 4-nitrobenzyl |

TABLE 1-continued (Compound II)

| No. | R¹ | R² | R⁴ | R⁶ | X | piperidine ring | R³ |
|---|---|---|---|---|---|---|---|
| 77 | " | | " | " | —CH=CH— | 4-piperidine | 4-nitrobenzyl |
| 78 | " | | " | " | —CH=CHCH₂— | " | 4-nitrobenzyl |
| 79 | " | | " | " | —CH₂— | " | 4-trifluoromethylbenzyl |
| 80 | " | | " | " | —(CH₂)₂— | " | 4-trifluoromethylbenzyl |
| 81 | " | | " | " | —CH= | =piperidine | 4-trifluoromethylbenzyl |
| 82 | " | | " | " | —(CH₂)₃— | 4-piperidine | 4-trifluoromethylbenzyl |
| 83 | " | | " | " | —CH=CH— | " | 4-trifluoromethylbenzyl |
| 84 | " | | " | " | —CH=CHCH₂— | " | 4-trifluoromethylbenzyl |
| 85 | " | | " | " | —CH₂— | " | sec-phenethyl |
| 86 | " | | " | " | —(CH₂)₂— | " | sec-phenethyl |
| 87 | " | | " | " | —(CH₂)₃— | " | sec-phenethyl |
| 88 | " | | " | " | —CH= | =piperidine | sec-phenethyl |
| 89 | " | | " | " | —CH=CH— | 4-piperidine | sec-phenethyl |
| 90 | " | | " | " | —CH=CHCH₂— | " | sec-phenethyl |
| 91 | " | | " | " | —CH₂— | " | diphenylmethyl |
| 92 | " | | " | " | —(CH₂)₂— | " | diphenylmethyl |
| 93 | " | | " | " | —(CH₂)₃— | " | diphenylmethyl |
| 94 | " | | " | " | —CH= | =piperidine | diphenylmethyl |
| 95 | —CH₂CH₂CH₂— | | H | H | —CH=CH— | 4-piperidine | diphenylmethyl |

TABLE 1-continued (Compound II)

| No. | R¹ | R² | R⁴ | R⁶ | X | piperidine (R⁵) | R³ |
|---|---|---|---|---|---|---|---|
| 96 | " |  | " | " | —CH=CHCH₂— | " | diphenyl-methyl |
| 97 | " |  | " | " | —CH₂— | " | di(4-fluoro-phenyl)-methyl |
| 98 | " |  | " | " | —(CH₂)₂— | " | di(4-fluoro-phenyl)-methyl |
| 99 | " |  | " | " | —(CH₂)₃— | " | di(4-fluoro-phenyl)-methyl |
| 100 | " |  | " | " | —CH= | =piperidin-4-ylidene (N—) | di(4-fluoro-phenyl)-methyl |
| 101 | " |  | " | " | —CH=CH— | piperidin-4-yl (N—) | di(4-fluoro-phenyl)-methyl |
| 102 | " |  | " | " | —CH=CHCH₂— | " | di(4-fluoro-phenyl)-methyl |
| 103 | " |  | " | " | —CH₂— | " | 2-thienyl-methyl |
| 104 | " |  | " | " | —(CH₂)₂— | " | 2-thienyl-methyl |
| 105 | " |  | " | " | —(CH₂)₃— | " | 2-thienyl-methyl |
| 106 | " |  | " | " | —CH= | =piperidin-4-ylidene (N—) | 2-thienyl-methyl |
| 107 | " |  | " | " | —CH=CH— | piperidin-4-yl (N—) | 2-thienyl-methyl |
| 108 | " |  | " | " | —CH=CHCH₂— | " | 2-thienyl-methyl |
| 109 | " |  | " | " | —CH₂— | " | 2-pyridyl-methyl |
| 110 | " |  | " | " | —(CH₂)₂— | " | 2-pyridyl-methyl |
| 111 | " |  | " | " | —(CH₂)₂— | " | 2-pyridyl-methyl |
| 112 | " |  | " | " | —CH= | =piperidin-4-ylidene (N—) | 2-pyridyl-methyl |
| 113 | —CH₂CH₂CH₂— |  | H | H | —CH=CH— | piperidin-4-yl (N—) | 2-pyridyl-methyl |
| 114 | " |  | " | " | —CH=CHCH₂— | " | 2-pyridyl- |

TABLE 1-continued (Compound II)

| No. | R¹ | R² | R⁴ | R⁶ | X | ring | R³ |
|---|---|---|---|---|---|---|---|
| 115 | | " | | " | " | —CH₂— | " | methyl 4-pyridyl-methyl |
| 116 | | " | | " | " | —(CH₂)₂— | " | 4-pyridyl-methyl |
| 117 | | " | | " | " | —(CH₂)₃— | " | 4-pyridyl-methyl |
| 118 | | " | | " | " | —CH= |  | 4-pyridyl-methyl |
| 119 | | " | | " | " | —CH=CH— | 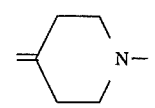 | 4-pyridyl-methyl |
| 120 | | " | | " | " | —CH=CHCH₂— | " | 4-pyridyl-methyl |
| 121 | | " | | " | " | —CH₂— | " | 2-pyrimidinyl-methyl |
| 122 | | " | | " | " | —(CH₂)₂— | " | 2-pyrimidinyl-methyl |
| 123 | | " | | " | " | —(CH₂)₃— | " | 2-pyrimidinyl-methyl |
| 124 | | " | | " | " | —CH= | 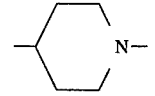 | 2-pyrimidinyl-methyl |
| 125 | | " | | " | " | —CH=CH— | 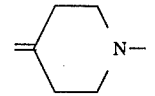 | 2-pyrimidinyl-methyl |
| 126 | | " | | " | " | —CH=CHCH₂— | " | 2-pyrimidinyl-methyl |
| 127 | | " | | " | " | —CH₂— | " | 4-pyrimidinyl-methyl |
| 128 | | " | | " | " | —(CH₂)₂— | " | 4-pyrimidinyl-methyl |
| 129 | | " | | " | " | —(CH₂)₃— | " | 4-pyrimidinyl-methyl |
| 130 | | " | | " | " | —CH= | 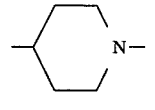 | 4-pyrimidinyl-methyl |
| 131 | | " | | " | " | —CH=CH— | 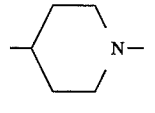 | 4-pyrimidinyl-methyl |

TABLE 1-continued (Compound II)

| No. | R¹ | R² | R⁴ | R⁶ | X | (R⁵-piperidinyl/tetrahydropyridinyl-N—) | R³ |
|---|---|---|---|---|---|---|---|
| 132 | —CH$_2$CH$_2$CH$_2$— |  | H | H | —CH=CHCH$_2$— | (piperidinyl-N—) | 4-pyrimidinylmethyl |
| 133 | " |  | " | " | —(CH$_2$)$_2$— | " | 4-difluoromethoxybenzyl |
| 134 | " |  | " | " | " | " | 3-difluoromethoxybenzyl |
| 135 | " |  | " | " | " | " | 2-difluoromethoxybenzyl |
| 136 | H | H | " | " | —(CH$_2$)$_2$— | " | benzyl |
| 137 | " | CH$_3$ | " | " | " | " | " |
| 138 | " | C$_2$H$_5$ | " | " | " | " | " |
| 139 | " | C$_3$H$_7$ | " | " | " | " | " |
| 140 | " | i-C$_3$H$_7$ | " | " | " | " | " |
| 141 | " | C$_4$H$_9$ | " | " | " | " | " |
| 142 | " | sec-C$_4$H$_9$ | " | " | " | " | " |
| 143 | " | C$_6$H$_{13}$ | " | " | " | " | " |
| 144 | " | C$_8$H$_{17}$ | " | " | " | " | " |
| 145 | " | C$_{10}$H$_{21}$ | " | " | " | " | " |
| 146 | " | Cl | " | " | " | " | " |
| 147 | " | Br | " | " | " | " | " |
| 148 | " | OCH$_3$ | " | " | " | " | " |
| 149 | " | OC$_2$H$_5$ | " | " | " | " | " |
| 150 | CH$_3$ | CH$_3$ | H | H | —(CH$_2$)$_2$— | (piperidinyl-N—) | benzyl |
| 151 | C$_2$H$_5$ | " | " | " | " | " | " |
| 152 | C$_3$H$_7$ | " | " | " | " | " | " |
| 153 | i-C$_3$H$_7$ | " | " | " | " | " | " |
| 154 | C$_4$H$_9$ | " | " | " | " | " | " |
| 155 | sec-C$_4$H$_9$ | " | " | " | " | " | " |
| 156 | i-C$_4$H$_9$ | " | " | " | " | " | " |
| 157 | C$_5$H$_{11}$ | " | " | " | " | " | " |
| 158 | C$_7$H$_{15}$ | " | " | " | " | " | " |
| 159 | C$_9$H$_{19}$ | " | " | " | " | " | " |
| 160 | Cl | " | " | " | " | " | " |
| 161 | Br | " | " | " | " | " | " |
| 162 | Cl | " | " | " | —CH=CH— | " | " |
| 163 | —CH$_2$CH$_2$CH$_2$CH$_2$— |  | " | " | —(CH$_2$)$_2$— | " | " |
| 164 | —CH(CH$_3$)CH$_2$CH$_2$— |  | " | " | " | " | " |
| 165 | —CH$_2$CH(CH$_3$)CH$_2$— |  | " | " | " | " | " |
| 166 | —CH$_2$CH$_2$CH(CH$_3$)— |  | " | " | " | " | " |
| 167 | —CH$_2$CH$_2$CH(OH)— |  | " | " | " | " | " |
| 168 | —CH$_2$CH$_2$CH(OCH$_3$)— |  | " | " | " | " | " |
| 169 | —CH$_2$CH$_2$CH(OC$_2$H$_5$)— |  | H | H | —(CH$_2$)$_2$— | (piperidinyl-N—) | benzyl |
| 170 | —CH$_2$CH$_2$CH(OC$_3$H$_7$)— |  | " | " | " | " | " |
| 171 | —CH$_2$CH$_2$CH(OCH$_2$CH=CH$_2$)— |  | " | " | " | " | " |
| 172 | —CH$_2$CH$_2$CH(OCH$_2$—C$_6$H$_5$)— |  | " | " | " | " | " |
| 173 | —CH$_2$CH$_2$CH(OCH$_3$)— |  | " | " | —CH=CH— | " | " |
| 174 | —CH$_2$CH$_2$CH(OCOH)— |  | " | " | —(CH$_2$)$_2$— | " | " |
| 175 | —CH$_2$CH$_2$CH$_2$— |  | " | " | —CH=CH— | " | " |
| 176 | —CH$_2$CH$_2$CH(OCOCH$_3$)— |  | " | " | —(CH$_2$)$_2$— | " | " |
| 177 | —CH$_2$CH$_2$CH(OCOC$_2$H$_5$)— |  | " | " | " | " | " |
| 178 | —CH$_2$CH$_2$CH(OCOC$_3$H$_7$)— |  | " | " | " | " | " |
| 179 | —CH$_2$CH$_2$CH(OCOC$_5$H$_{11}$)— |  | " | " | " | " | " |

TABLE 1-continued (Compound II)

| No. | R¹ | R² | R⁴ | R⁶ | X | (R⁵ ring) | R³ |
|---|---|---|---|---|---|---|---|
| 180 | —CH₂CH₂CH(OCOC₉H₁₉)— | | " | " | " | " | " |
| 181 | —CH₂CH₂CH(OCOCH₂—C₆H₅)— | | " | " | " | " | " |
| 182 | —CH₂CH₂CH(OCO—C₆H₅)— | | " | " | " | " | " |
| 183 | —CH₂CH₂CH(F)— | | " | " | " | " | " |
| 184 | —CH₂CH₂CH(Cl)— | | " | " | " | " | " |
| 185 | —CH₂CH₂CH(Br)— | | " | " | " | " | " |
| 186 | —CH₂CH₂C(F)₂— | | " | " | " | " | " |
| 187 | —CH(Br)CH₂CH(Br)— | | " | " | " | " | " |
| 188 | —CH₂CH₂CH(F)— | | H | H | —CH=CH— | piperidin-4-yl (N—) | benzyl |
| 189 | CH₃ | H | " | " | —(CH₂)₂— | " | " |
| 190 | " | Cl | " | " | " | " | " |
| 191 | " | Br | " | " | " | " | " |
| 192 | " | CH₂OH | " | " | " | " | " |
| 193 | " | CH₂OCH₃ | " | " | " | " | " |
| 194 | " | CH₂OCOCH₃ | " | " | " | " | " |
| 195 | " | CH₂F | " | " | " | " | " |
| 196 | " | CH₂Cl | " | " | " | " | " |
| 197 | C₂H₅ | H | " | " | " | " | 2-pyrimidinyl-methyl |
| 198 | —CH₂C(CH₃)₂CH₂— | | " | " | " | " | benzyl |
| 199 | CH₃ | CH₃ | " | " | —CH=CH— | " | " |
| 200 | C₂H₅ | C₂H₅ | " | " | " | " | " |
| 201 | —CH₂C(CH₃)₂CH₂— | | " | " | " | " | " |
| 202 | CH₃ | H | " | " | " | " | " |
| 203 | C₂H₅ | " | " | " | " | " | " |
| 204 | C₃H₇ | " | " | " | " | " | " |
| 205 | C₂H₅ | " | " | " | —(CH₂)₂— | " | " |
| 206 | C₃H₇ | " | " | " | " | " | " |
| 207 | —CH₂CH₂CH(O—C₆H₅)— | | H | H | —(CH₂)₂— | piperidin-4-yl (N—) | benzyl |
| 208 | —CH₂CH₂CH(O-1-C₁₀H₇)— | | " | " | " | " | " |
| 209 | —CH₂CH₂CH₂— | | " | " | —CH=CH— | " | 3-pyridyl-methyl |
| 210 | " | | " | " | —(CH₂)₂— | " | 3-pyridyl-methyl |
| 211 | " | | " | " | —CH=CH— | " | 2-methyl-benzyl |
| 212 | " | | " | " | —(CH₂)₂— | " | 2-methyl-benzyl |
| 213 | " | | " | " | —CH=CH— | " | 3-methyl-benzyl |
| 214 | " | | " | " | —(CH₂)₂— | " | 3-methyl-benzyl |
| 215 | " | | " | " | —CH₂— | 4-ethoxy-piperidin-4-yl (C₂H₅O, N—) | benzyl |
| 216 | " | | " | " | " | 4-hydroxy-piperidin-4-yl (OH, N—) | " |
| 217 | " | | " | " | " | tetrahydropyridin-4-yl (N—) | " |

TABLE 1-continued (Compound II)

| No. | R¹ | R² | R⁴ | R⁶ | X | (piperidine ring with R⁵) | R³ |
|---|---|---|---|---|---|---|---|
| 218 | " | | " | " | $-(CH_2)_2-$ | (4-piperidinyl) | 4-cyano-benzyl |
| 219 | $CH_3$ | H | " | " | $-CH_2-$ | " | 2-pyridyl-methyl |
| 220 | " | | " | " | " | " | benzyl |
| 221 | $-CH_2CH_2CH_2-$ | | $-COCH_3$ | " | $-(CH_2)_2-$ | " | " |
| 222 | $-COOC_2H_5$ | H | H | " | " | " | " |
| 223 | $C_2H_5$ | $C_2H_5$ | " | " | " | " | " |
| 224 | $-CH_2CH_2CH_2-$ | | " | " | " | " | 1-naphthyl-methyl |
| 225 | " | | " | " | " | " | 3-cyano-benzyl |
| 226 | $CH_3$ | H | H | 2-F | $-CH_2-$ | (4-piperidinyl) | benzyl |
| 227 | " | | " | 3-F | " | " | " |
| 228 | " | | " | 3-Cl | " | " | " |
| 229 | Cl | | " | H | $-(CH_2)_2-$ | " | " |
| 230 | Br | | " | " | " | " | " |
| 231 | $-CH_2CH_2CH_2-$ | | " | " | " | " | 3,4-methylene-dioxy-benzyl |
| 232 | " | | " | " | " | " | 3-tri-fluoro-methyl-benzyl |
| 233 | " | | " | " | " | " | 2,3-di-methoxy-benzyl |
| 234 | $CH_3$ | $CH_3$ | " | " | $-CH_2-$ | " | benzyl |
| 235 | $-CH_2CH_2CH_2-$ | | " | " | $-(CH_2)_2-$ | " | 3,4-ethylene-dioxy-benzyl |
| 236 | $-CH_2CH_2CH(OH)-$ | | " | " | $-CH_2-$ | " | " |
| 237 | $-CH_2CH_2CH(OCOCH_3)-$ | | " | " | " | " | " |
| 238 | $-CH_2CH_2CH_2-$ | | " | " | $-(CH_2)_2-$ | " | 6-methyl-2-pyridyl-methyl |
| 239 | " | | " | " | " | " | 3-benzyl-oxy-benzyl |
| 240 | $NO_2$ | $OCH_3$ | " | " | " | " | benzyl |
| 241 | $NH_2$ | Cl | " | " | " | " | " |
| 242 | $-CH_2CH_2CH_2-$ | | H | H | $-(CH_2)_2-$ | (4-piperidinyl) | 2-nitro-benzyl |
| 243 | " | | " | " | " | " | 3-nitro-benzyl |
| 244 | " | | " | " | " | " | 3-amino-benzyl |
| 245 | " | | " | 2-$OCH_3$ | $-CH_2-$ | " | " |
| 246 | $-CH_2CH_2CH_2CH_2-$ | | " | " | " | " | " |
| 247 | $-CH_2CH_2CH_2-$ | | " | 2-Cl | " | " | " |
| 248 | $CH_3$ | H | " | H | $-(CH_2)_2-$ | " | 2-pyridyl- |

TABLE 1-continued (Compound II)

| No. | R¹ | R² | R⁴ | R⁶ | X | (ring) | R³ |
|---|---|---|---|---|---|---|---|
| 249 | —CH₂CH₂CH₂— | | " | " | " | " | methyl 2-acetyl-aminobenzyl |
| 250 | CH₃ | H | " | 2-CH₃ | —CH₂— | " | benzyl |
| 251 | " | " | " | 3-CH₃ | " | " | " |
| 252 | C₂H₅ | " | " | H | " | " | " |
| 253 | C₃H₇ | " | " | " | " | " | " |
| 254 | i-C₃H₇ | " | " | " | " | " | " |
| 255 | C₄H₉ | " | " | " | " | " | " |
| 256 | sec-C₄H₉ | " | " | " | " | " | " |
| 257 | i-C₄H₉ | " | " | " | " | " | " |
| 258 | CH₃ | " | " | " | " | " | 2-thienylmethyl |
| 259 | " | " | " | " | " | " | 3-thienylmethyl |
| 260 | " | " | " | " | " | " | 2-furylmethyl |
| 261 | CH₃ | H | H | H | —CH₂— | 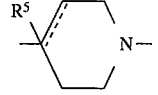 | 3-furylmethyl |
| 262 | " | " | " | " | " | " | 3-pyridylmethyl |
| 263 | " | " | " | " | " | " | 4-pyridylmethyl |
| 264 | " | " | " | " | " | " | 2-pyrimidinylmethyl |
| 265 | " | " | " | " | " | " | 4-pyrimidinylmethyl |
| 266 | " | " | " | 3-OCH₂ | " | " | benzyl |
| 267 | —CH₂CH₂CH₂— | " | " | H | " | " | 3-thienylmethyl |
| 268 | " | " | " | " | " | " | 3-pyridylmethyl |
| 269 | " | " | " | " | " | " | 2-furylmethyl |
| 270 | " | " | " | " | " | " | 3-furylmethyl |
| 271 | " | " | " | " | —(CH₂)₂— | " | 4-aminobenzyl |
| 272 | " | " | " | " | " | " | 2-aminobenzyl |
| 273 | " | " | " | " | " | " | 4-acetylaminobenzyl |
| 274 | " | " | " | " | " | " | 3-acetylaminobenzyl |
| 275 | CH₃ | H | —COH | " | —CH₂— | " | benzyl |
| 276 | " | " | —COC₂H₅ | " | " | " | " |
| 277 | " | " | —COC₃H₇ | " | " | " | " |
| 278 | CH₃ | H | —COC₄H₉ | H | —CH₂— | 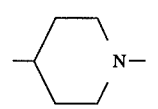 | benzyl |
| 279 | " | " | —COC₆H₁₃ | " | " | " | " |
| 280 | " | " | —COC₈H₂₇ | " | " | " | " |
| 281 | " | " | —COC₁₀H₂₁ | " | " | " | " |

TABLE 1-continued (Compound II)

| No. | R¹ | R² | R⁴ | R⁶ | X | (ring with R⁵) | R³ |
|---|---|---|---|---|---|---|---|
| 282 | " | " | H | " | " | C₃H₇O-[piperidine]-N— | " |
| 283 | " | " | " | " | " | C₄H₉O-[piperidine]-N— | " |
| 284 | " | " | " | " | " | CH₃O-[piperidine]-N— | " |
| 285 | " | " | " | 3-Br | " | [piperidine]-N— | " |
| 286 | " | " | " | 3-C₂H₅ | " | " | " |
| 287 | " | " | " | 3-C₃H₇ | " | " | " |
| 288 | " | " | " | 3-OC₂H₅ | " | " | " |
| 289 | " | " | " | 3-OC₃H₇ | " | " | " |
| 290 | " | " | " | 3-OC₄H₉ | " | " | " |
| 291 | " | " | " | H | " | " | 4-ethoxy-benzyl |
| 292 | " | " | " | " | " | " | 4-butoxy-benzyl |
| 293 | " | " | " | " | " | " | 4-t-butyl-benzyl |
| 294 | " | " | " | " | " | " | 4-difluoromethyl-benzyl |
| 295 | CH₃ | H | H | H | —CH₂— | [piperidine]-N— | 4-(2-fluoroethoxy)-benzyl |
| 296 | " | " | " | " | " | " | 4-butyryl-amino-benzyl |
| 297 | H | OC₃H₇ | " | " | " | " | benzyl |
| 298 | " | OC₄H₉ | " | " | " | " | " |
| 299 | —CH₂CH₂CH₂CH(CH₃)— | | " | " | " | " | " |
| 300 | —CH₂CH₂CH(OCH₂CH₂C₆H₅)— | | " | " | " | " | " |
| 301 | CH₃ | H | " | " | " | " | phenethyl |
| 302 | " | " | " | " | " | " | diphenylmethyl |
| 303 | C₂H₅ | " | " | 3-OCH₃ | " | " | benzyl |
| 304 | " | " | " | 3-F | " | " | " |
| 305 | " | " | " | 3-Cl | " | " | " |
| 306 | " | " | " | 3-CH₃ | " | " | " |
| 307 | " | " | " | H | " | " | 2-thienylmethyl |
| 308 | C₃H₇ | " | " | 3-OCH₃ | " | " | benzyl |
| 309 | " | " | " | 3-F | " | " | " |
| 310 | " | " | " | 3-Cl | " | " | " |
| 311 | " | " | " | 3-CH₃ | " | " | " |
| 312 | " | " | " | H | " | " | 2-thienylmethyl |
| 313 | i-C₃H₇ | H | H | 3-OCH₃ | —CH₂— | [piperidine]-N— | benzyl |

TABLE 1-continued (Compound II)

| No. | $R^1$ | $R^2$ | $R^4$ | $R^6$ | X | $R^5$-ring-N- | $R^3$ |
|---|---|---|---|---|---|---|---|
| 314 | " | " | " | 3-F | " | " | " |
| 315 | " | " | " | 3-Cl | " | " | " |
| 316 | " | " | " | 3-CH₃ | " | " | " |
| 317 | CH₃ | " | " | H | " | " | 3-phenyl-propyl |
| 318 | " | " | " | 3-OCH₃ | " | " | 2-thienyl-methyl |
| 319 | " | " | " | 3-F | " | " | 2-thienyl-methyl |
| 320 | " | " | " | 3-Cl | " | " | 2-thienyl-methyl |
| 321 | " | " | " | 3-CH₃ | " | " | 2-thienyl-methyl |
| 322 | —CH₂CH₂CH₂— | " | " | 3-OCH₃ | " | " | 2-thienyl-methyl |
| 323 | " | " | " | 3-F | " | " | 2-thienyl-methyl |
| 324 | " | " | " | 3-Cl | " | " | 2-thienyl-methyl |
| 325 | " | " | " | 3-CH₃ | " | " | 2-thienyl-methyl |
| 326 | C₂H₅ | " | " | H | " | " | 3-thienyl-methyl |
| 327 | CH₃ | " | " | 3-OCH₃ | " | " | 3-thienyl-methyl |
| 328 | " | " | " | 3-F | " | " | 3-thienyl-methyl |
| 329 | " | " | " | 3-Cl | " | " | 3-thienyl-methyl |
| 330 | " | " | " | 3-CH₃ | " | " | 3-thienyl-methyl |

TABLE 2

(Compound III)

| No. | $R^1$ | $R^2$ | $R^4$ | Y | $R^5$-ring-N- | $R^3$ |
|---|---|---|---|---|---|---|
| 1 | —CH₂CH₂CH₂— | | H | double bond | (=ring N-) | benzyl |
| 2 | " | | " | single bond | (ring N-) | " |
| 3 | " | | " | =CH— | " | " |
| 4 | " | | " | —CH₂— | " | " |
| 5 | " | | " | =CHCH₂— | " | " |
| 6 | " | | " | —(CH₂)₂— | " | " |
| 7 | " | | " | double bond | (=ring N-) | 4-fluorobenzyl |
| 8 | " | | " | single bond | (ring N-) | " |
| 9 | " | | " | =CH— | " | " |
| 10 | " | | " | —CH₂— | " | " |

TABLE 2-continued (Compound III)

| No. | R¹ | R² | R⁴ | Y | (ring structure) | R³ |
|---|---|---|---|---|---|---|
| 11 | | " | | " | =CHCH₂— | " | " |
| 12 | | " | | " | —(CH₂)₂— | " | " |
| 13 | | " | | " | double bond | =piperidin-4-ylidene (N—) | 3-fluorobenzyl |
| 14 | | " | | " | single bond | piperidin-4-yl (N—) | " |
| 15 | | " | | " | =CH— | " | " |
| 16 | | " | | " | —CH₂— | " | " |
| 17 | | " | | " | =CHCH₂— | " | " |
| 18 | | " | | " | —(CH₂)₂— | " | " |
| 19 | —CH₂CH₂CH₂— | | H | double bond | =piperidin-4-ylidene (N—) | 2-fluorobenzyl |
| 20 | | " | | " | single bond | piperidin-4-yl (N—) | " |
| 21 | | " | | " | =CH— | " | " |
| 22 | | " | | " | —CH₂— | " | " |
| 23 | | " | | " | =CHCH₂— | " | " |
| 24 | | " | | " | —(CH₂)₂— | " | " |
| 25 | | " | | " | double bond | =piperidin-4-ylidene (N—) | 4-methoxybenzyl |
| 26 | | " | | " | single bond | piperidin-4-yl (N—) | " |
| 27 | | " | | " | =CH— | " | " |
| 28 | | " | | " | —CH₂— | " | " |
| 29 | | " | | " | =CHCH₂— | " | " |
| 30 | | " | | " | —(CH₂)₂— | " | " |
| 31 | | " | | " | double bond | =piperidin-4-ylidene (N—) | 3-methoxybenzyl |
| 32 | | " | | " | single bond | piperidin-4-yl (N—) | " |
| 33 | | " | | " | =CH— | " | " |
| 34 | | " | | " | —CH₂— | " | " |
| 35 | | " | | " | =CHCH₂— | " | " |
| 36 | | " | | " | —(CH₂)₂— | " | " |
| 37 | —CH₂CH₂CH₂— | | H | double bond | =piperidin-4-ylidene (N—) | 4-hydroxybenzyl |

TABLE 2-continued (Compound III)

| No. | R¹ | R² | R⁴ | Y | ring group | R³ |
|---|---|---|---|---|---|---|
| 38 | | " | | single bond | piperidine | " |
| 39 | | " | | =CH— | " | " |
| 40 | | " | | —CH₂— | " | " |
| 41 | | " | | =CHCH₂— | " | " |
| 42 | | " | | —(CH₂)₂— | " | " |
| 43 | | " | | double bond | piperidinylidene | 4-chlorobenzyl |
| 44 | | " | | single bond | piperidine | " |
| 45 | | " | | =CH— | " | " |
| 46 | | " | | —CH₂— | " | " |
| 47 | | " | | =CHCH₂— | " | " |
| 48 | | " | | —(CH₂)₂— | " | " |
| 49 | | " | | double bond | piperidinylidene | 3-chlorobenzyl |
| 50 | | " | | single bond | piperidine | " |
| 51 | | " | | =CH— | " | " |
| 52 | | " | | —CH₂— | " | " |
| 53 | | " | | =CHCH₂— | " | " |
| 54 | | " | | —(CH₂)₂— | " | " |
| 55 | —CH₂CH₂CH₂— | | H | double bond | piperidinylidene | 2-chlorobenzyl |
| 56 | | " | | single bond | piperidine | " |
| 57 | | " | | =CH— | " | " |
| 58 | | " | | —CH₂— | " | " |
| 59 | | " | | =CHCH₂— | " | " |
| 60 | | " | | —(CH₂)₂— | " | " |
| 61 | | " | | double bond | piperidinylidene | 4-methylbenzyl |
| 62 | | " | | single bond | piperidine | " |
| 63 | | " | | =CH— | " | " |
| 64 | | " | | —CH₂— | " | " |
| 65 | | " | | =CHCH₂— | " | " |
| 66 | | " | | —(CH₂)₂— | " | " |

TABLE 2-continued (Compound III)

$$R^5 \diagup\!\!\!\diagdown N-$$

| No. | R¹ | R² | R⁴ | Y | (ring) | R³ |
|---|---|---|---|---|---|---|
| 67 | | " | " | double bond | =⟨N-⟩ | 4-nitrobenzyl |
| 68 | | " | " | single bond | -⟨N-⟩ | " |
| 69 | | " | | " | =CH- | " | " |
| 70 | | " | | " | -CH₂- | " | " |
| 71 | | " | | " | =CHCH₂- | " | " |
| 72 | | " | | " | -(CH₂)₂- | " | " |
| 73 | -CH₂CH₂CH₂- | | H | double bond | =⟨N-⟩ | 4-trifluoromethylbenzyl |
| 74 | | " | | " | single bond | -⟨N-⟩ | " |
| 75 | | " | | " | =CH- | " | " |
| 76 | | " | | " | -CH₂- | " | " |
| 77 | | " | | " | =CHCH₂- | " | " |
| 78 | | " | | " | -(CH₂)₂- | " | " |
| 79 | | " | | " | double bond | =⟨N-⟩ | sec-phenethyl |
| 80 | | " | | " | single bond | -⟨N-⟩ | " |
| 81 | | " | | " | =CH- | " | " |
| 82 | | " | | " | -CH₂- | " | " |
| 83 | | " | | " | =CHCH₂- | " | " |
| 84 | | " | | " | -(CH₂)₂- | " | " |
| 85 | | " | | " | double bond | =⟨N-⟩ | diphenylmethyl |
| 86 | | " | | " | single bond | -⟨N-⟩ | " |
| 87 | | " | | " | =CH- | " | " |
| 88 | | " | | " | -CH₂- | " | " |
| 89 | | " | | " | =CHCH₂- | " | " |
| 90 | | " | | " | -(CH₂)₂- | " | " |
| 91 | -CH₂CH₂CH₂- | | H | double bond | =⟨N-⟩ | di(4-fluorophenyl)methyl |

TABLE 2-continued (Compound III)

| No. | R¹ | R² | R⁴ | Y | (ring with R⁵) | R³ |
|---|---|---|---|---|---|---|
| 92 |  | " |  | " | single bond | piperidine (single bond to ring) | " |
| 93 |  | " |  | " | =CH— | " | " |
| 94 |  | " |  | " | —CH₂— | " | " |
| 95 |  | " |  | " | =CHCH₂— | " | " |
| 96 |  | " |  | " | —(CH₂)₂— | " | " |
| 97 |  | " |  | " | double bond | piperidine (=) | 2-thienylmethyl |
| 98 |  | " |  | " | single bond | piperidine | " |
| 99 |  | " |  | " | =CH— | " | " |
| 100 |  | " |  | " | —CH₂— | " | " |
| 101 |  | " |  | " | =CHCH₂— | " | " |
| 102 |  | " |  | " | —(CH₂)₂— | " | " |
| 103 |  | " |  | " | double bond | piperidine (=) | 2-pyridylmethyl |
| 104 |  | " |  | " | single bond | piperidine | " |
| 105 |  | " |  | " | =CH— | " | " |
| 106 |  | " |  | " | —CH₂— | " | " |
| 107 |  | " |  | " | =CHCH₂— | " | " |
| 108 |  | " |  | " | —(CH₂)₂— | " | " |
| 109 | —CH₂CH₂CH₂— |  | H | double bond | piperidine (=) | 4-pyridylmethyl |
| 110 |  | " |  | " | single bond | piperidine | " |
| 111 |  | " |  | " | =CH— | " | " |
| 112 |  | " |  | " | —CH₂— | " | " |
| 113 |  | " |  | " | =CHCH₂— | " | " |
| 114 |  | " |  | " | —(CH₂)₂— | " | " |
| 115 |  | " |  | " | double bond | piperidine (=) | 2-pyrimidinylmethyl |
| 116 |  | " |  | " | single bond | piperidine | " |
| 117 |  | " |  | " | =CH— | " | " |
| 118 |  | " |  | " | —CH₂— | " | " |
| 119 |  | " |  | " | =CHCH₂— | " | " |
| 120 |  | " |  | " | —(CH₂)₂— | " | " |

TABLE 2-continued (Compound III)

| No. | R¹ | R² | R⁴ | Y | ring (R⁵) | R³ |
|---|---|---|---|---|---|---|
| 121 | | " | " | double bond | =piperidinylidene | 4-pyrimidinylmethyl |
| 122 | | " | " | single bond | piperidinyl | " |
| 123 | | " | " | =CH— | " | " |
| 124 | | " | " | —CH₂— | " | " |
| 125 | | " | " | =CHCH₂— | " | " |
| 126 | | " | " | —(CH₂)₂— | " | " |
| 127 | H | H | H | —CH₂— | piperidinyl | benzyl |
| 128 | " | CH₃ | " | " | " | " |
| 129 | " | C₂H₅ | " | " | " | " |
| 130 | " | C₃H₇ | " | " | " | " |
| 131 | " | i-C₃H₇ | " | " | " | " |
| 132 | " | C₄H₉ | " | " | " | " |
| 133 | " | sec-C₄H₉ | " | " | " | " |
| 134 | " | C₆H₁₃ | " | " | " | " |
| 135 | " | C₈H₁₇ | " | " | " | " |
| 136 | " | C₁₀H₂₁ | " | " | " | " |
| 137 | " | Cl | " | " | " | " |
| 138 | " | Br | " | " | " | " |
| 139 | " | OCH₃ | " | " | " | " |
| 140 | " | OC₂H₅ | " | " | " | " |
| 141 | CH₃ | CH₃ | " | " | " | " |
| 142 | C₂H₅ | " | " | " | " | " |
| 143 | C₃H₇ | " | " | " | " | " |
| 144 | i-C₃H₇ | " | " | " | " | " |
| 145 | C₄H₉ | CH₃ | H | —CH₂— | piperidinyl | benzyl |
| 146 | sec-C₄H₉ | " | " | " | " | " |
| 147 | i-C₄H₉ | " | " | " | " | " |
| 148 | C₅H₁₁ | " | " | " | " | " |
| 149 | C₇H₁₅ | " | " | " | " | " |
| 150 | C₉H₁₉ | " | " | " | " | " |
| 151 | Cl | CH₃ | " | " | " | " |
| 152 | Br | " | " | " | " | " |
| 153 | —CH₂CH₂CH₂CH₂— | | " | " | " | " |
| 154 | —CH(CH₃)CH₂CH₂— | | " | " | " | " |
| 155 | —CH₂CH(CH₃)CH₂— | | " | " | " | " |
| 156 | —CH₂CH₂CH(CH₃)— | | " | " | " | " |
| 157 | —CH₂CH₂CH(OH)— | | " | " | " | " |
| 158 | —CH₂CH₂CH(OCH₃)— | | " | " | " | " |
| 159 | —CH₂CH₂CH(OC₂H₅)— | | " | " | " | " |
| 160 | —CH₂CH₂CH(OC₃H₇)— | | " | " | " | " |
| 161 | —CH₂CH₂CH(OCH₂CH=CH₂)— | | " | " | " | " |
| 162 | —CH₂CH₂CH(OCH₂—C₆H₅)— | | " | " | " | " |
| 163 | —CH₂CH₂CH(OCOH)— | | " | " | " | " |
| 164 | —CH₂CH₂CH(OCOCH₃)— | | H | —CH₂— | piperidinyl | benzyl |
| 165 | —CH₂CH₂CH(OCOC₂H₅)— | | " | " | " | " |
| 166 | —CH₂CH₂CH(OCOC₃H₇)— | | " | " | " | " |

TABLE 2-continued (Compound III)

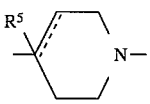

| No. | R¹ | R² | R⁴ | Y | (R⁵-piperidine) | R³ |
|---|---|---|---|---|---|---|
| 167 | $-CH_2CH_2CH(OCOC_5H_{11})-$ | | " | " | " | " |
| 168 | $-CH_2CH_2CH(OCOC_9H_{19})-$ | | " | " | " | " |
| 169 | $-CH_2CH_2CH(OCOCH_2-C_6H_5)-$ | | " | " | " | " |
| 170 | $-CH_2CH_2CH(OCO-C_6H_5)-$ | | " | " | " | " |
| 171 | $-CH_2CH_2CH(F)-$ | | " | " | " | " |
| 172 | $-CH_2CH_2CH(Cl)-$ | | " | " | " | " |
| 173 | $-CH_2CH_2CH(Br)-$ | | " | " | " | " |
| 174 | $-CH_2CH_2C(F)_2-$ | | " | " | " | " |
| 175 | $-CH(Br)CH_2CH(Br)-$ | | " | " | " | " |
| 176 | $CH_3$ | Cl | " | " | " | " |
| 177 | " | Br | " | " | " | " |
| 178 | " | $CH_2OH$ | " | " | " | " |
| 179 | " | $CH_2OCH_3$ | " | " | " | " |
| 180 | " | $CH_2OCOCH_3$ | " | " | " | " |
| 181 | " | $CH_2F$ | " | " | " | " |
| 182 | " | $CH_2Cl$ | " | " | " | " |
| 183 | $-CH_2CH_2CH_2-$ | | H | $-CH_2-$ | 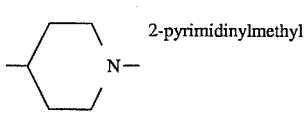 | 2-pyrimidinylmethyl |
| 184 | $-CH_2C(CH_3)_2CH_2-$ | | " | " | " | benzyl |
| 185 | $-CH_2CH_2CH(O-C_6H_5)-$ | | " | " | " | " |

In the formula (II), the compounds (IIa to e) wherein R⁴ is a hydrogen atom can be prepared by [Preparation process 1-1], [Preparation process 2-1], [Preparation process 3-1] or [Preparation process 4-1], and in the formula (III), the compounds (IIIa to e) wherein R⁴ is a hydrogen atom can be prepared by [Preparation process 1-2], [Preparation process 2-2], [Preparation process 3-2] or [Preparation process 4-2].

On the other hand, in the formula (II), the compound (IIf) wherein R⁴ is an acyl group can be prepared by [Preparation process 5-1] and in the formula (III), the compound (IIIf) wherein R⁴ is an acyl group can be prepared by [Preparation process 5-2].

[Preparation process 1-1]

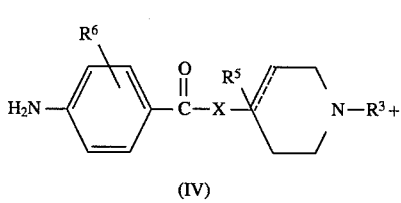

(IV)

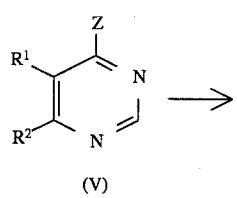

(V)

-continued

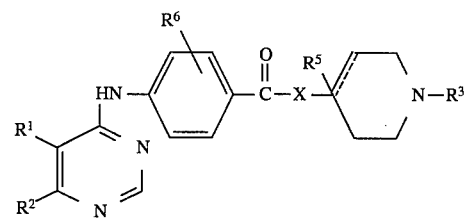

(IIa)

[Preparation process 1-2]

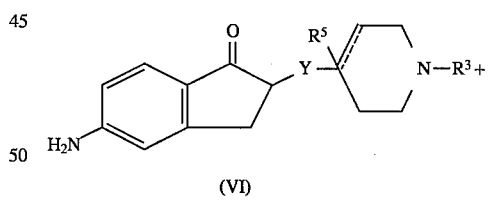

(VI)

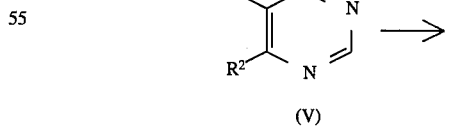

(V)

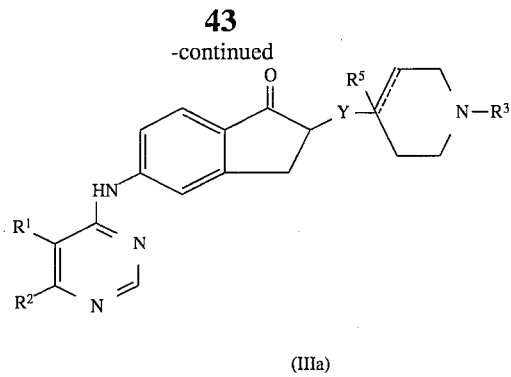

(IIIa)

(wherein $R^1$, $R^2$, $R^3$, $R^5$, $R^6$, X, Y and ⎯ have the same meanings as described above and Z represents a halogen atom)

In [Preparation process 1-1] or [Preparation process 1-2], the compound (IIa) or (IIIa) is prepared by reacting the compound (IV) or (VI) with the compound (V) in a 1- to 5-fold molar amount, preferably a 1- to 2-fold molar amount in a solvent in the presence or absence of an acid.

The solvent to be used is not particularly limited so long as it is inert to the above reactions, and may include, for example, alcohols such as methanol, ethanol, propanol, isopropanol, butanol, etc.; aprotic polar solvents such as dimethylformamide, dimethyl sulfoxide, dimethylacetamide, hexamethylphosphoric acid triamide, etc.; halogenated hydrocarbons such as chloroform, carbon tetrachloride, dichloroethane, etc.; esters such as ethyl acetate, etc.; and nitriles such as acetonitrile, etc. Preferred are the aforesaid alcohols, halogenated hydrocarbons and aprotic polar solvents.

As the acid to be used, there may be mentioned, for example, a Brønsted acid such as hydrochloric acid, sulfuric acid, phosphoric acid, acetic acid, propionic acid, methanesulfonic acid, benzenesulfonic acid, p-toluene-sulfonic acid, etc.; and a Lewis acid such as stannous chloride, stannic chloride, zinc chloride, aluminum chloride, titanium tetrachloride, etc., preferably hydrochloric acid, stannous chloride, stannic chloride and zinc chloride. The amount to be used is generally a 0.01- to 10-fold molar amount, preferably a 0.1- to 5-fold molar amount based on the compound (V).

The reaction temperature is 0° to 200° C., preferably the reaction is carried out in the range of 0° to 150° C. The reaction time varies depending on conditions other than those described above, but the reaction is carried out generally for 5 minutes to 24 hours, preferably for 10 minutes to 12 hours.

The compound (IV) is generally used as a free material, but a salt with the Brønsted acid or a complex with the Lewis acid as mentioned above may be also used. In that case, the reaction can proceed smoothly without further adding the Brønsted acid or Lewis acid as mentioned above to the reaction system.

Also, when the compound (IV) or (VI) wherein $R^5$ is a hydroxy group is reacted in the aforesaid alcohol in the presence of an acid, as the formed compound (IIa) or (IIIa), in addition to the compound wherein $R^5$ is a hydroxy group, a compound (for example, in the reaction in ethanol, a compound wherein $R_5$ is an ethoxy group) wherein $R^5$ is an alkoxy group which can be obtained by replacing the hydroxy group with an alcohol of the solvent and a compound having a double bond which is a dehydrated product can be obtained.

[Preparation process 2-1]

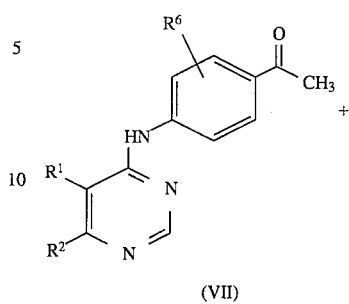

(VII)

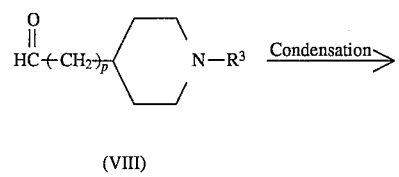

(VIII)

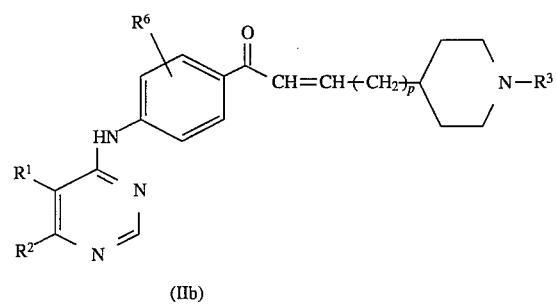

(IIb)

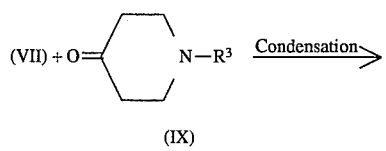

(IX)

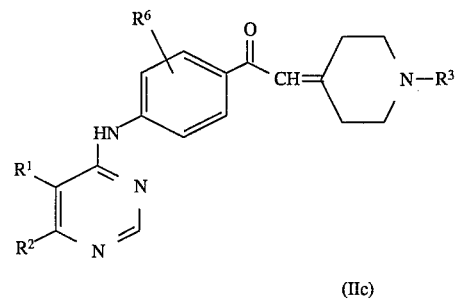

(IIc)

[Preparation process 2-2]

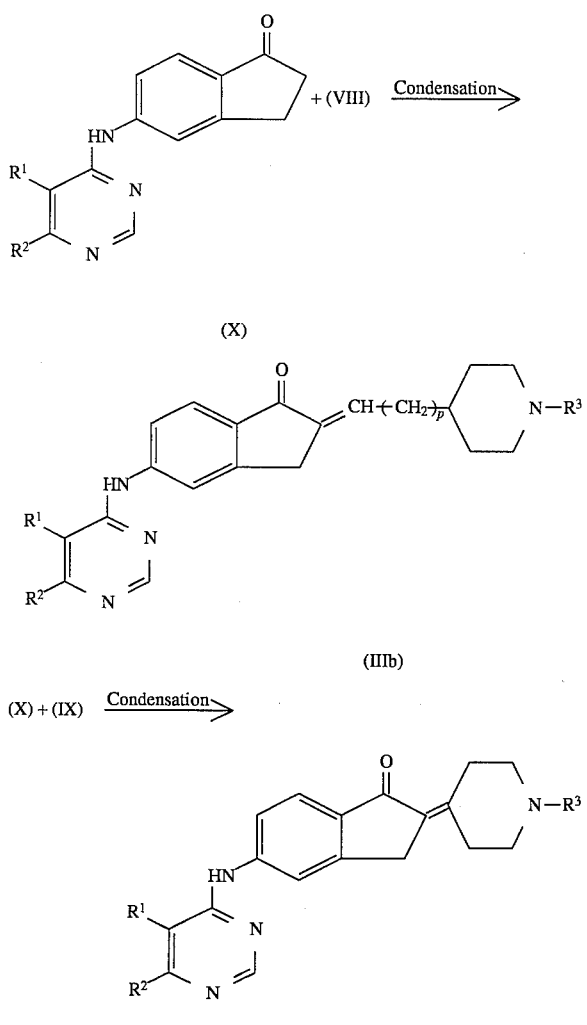

(wherein $R^1$, $R^2$, $R^3$, $R^6$ and p have the same meanings as described above)

In [Preparation process 2-1] or [Preparation process 2-2], the compound (IIb), (IIc), (IIIb) or (IIIc) is prepared by subjecting the compound (VII) or (X) and the compound (VIII) or (IX) in a 1- to 5-fold molar amount, preferably a 1- to 2-fold molar amount to condensation reaction in a solvent in the presence of a base.

The solvent to be used is not particularly limited so long as it is inert to the above reactions, and may include, for example, alcohols such as methanol, ethanol, propanol, isopropanol, butanol, etc.; ethers such as diethyl ether, diisopropyl ether, tetrahydrofuran, dioxane, etc.; aprotic polar solvents such as dimethylformamide, dimethyl sulfoxide, dimethylacetamide, etc.; nitriles such as acetonitrile, etc.; and esters such as ethyl acetate, etc. Preferred are the above alcohols, ethers and nitriles.

As the base to be used, there may be mentioned, for example, alkali metal alkoxides such as sodium methoxide, sodium ethoxide, potassium t-butoxide, etc.; alkyl lithiums such as butyl lithium, t-butyl lithium, etc.; alkali metal hydrides such as sodium hydride, lithium hydride, etc.; alkali metal amides such as sodium amide, etc.; amines such as triethylamine, tributylamine, diisopropylethylamine, pyridine, picoline, luridine, etc.; alkali metal hydroxides such as sodium hydroxide, potassium hydroxide, etc.; and alkali metal carbonates such as sodium carbonate, potassium carbonate, etc. Preferred are the above alkali metal alkoxides, alkyl lithiums, alkali metal hydrides and amines. The amount to be used is generally a 1- to 10-fold molar amount, preferably a 1- to 5-fold molar amount based on the compound (VII) or (X).

The reaction temperature is −70° to 150° C., preferably the reaction is carried out in the range of −50° to 100° C. The reaction time varies depending on conditions other than those described above, but the reaction is carried out generally for 15 minutes to 100 hours, preferably for 30 minutes to 72 hours.

[Preparation process 3-1]

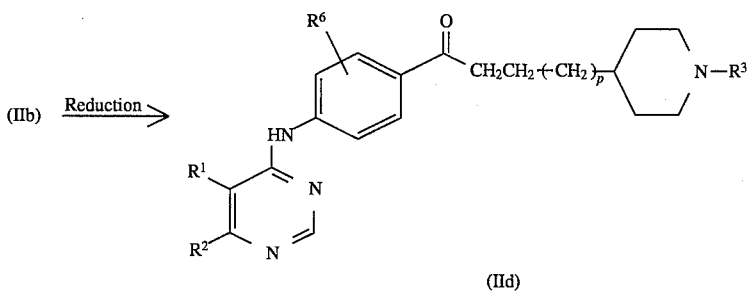

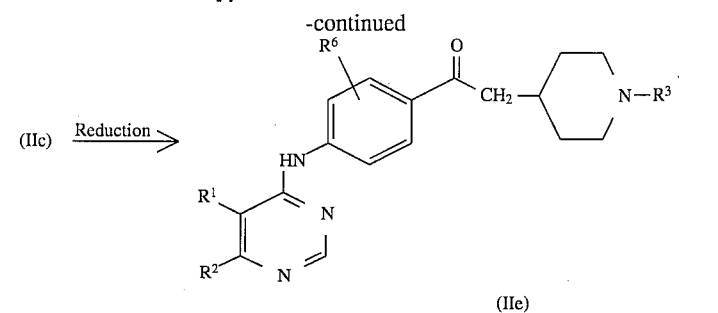

(IIe)

[Preparation process 3-2]

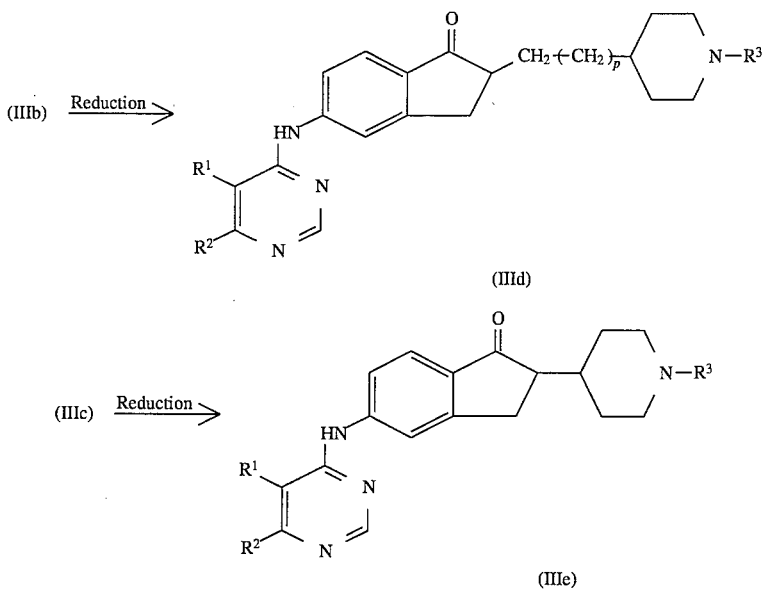

(wherein $R^1$, $R^2$, $R^3$, $R^6$ and p have the same meanings as described above)

In [Preparation process 3-1] or [Preparation process 3-2], the compound (IId), (IIe), (IIId) or (IIIe) is prepared by subjecting the compound (IIb), (IIc), (IIIb) or (IIIc) to catalytic reduction with a hydrogen gas in a solvent in the presence of a catalyst or to reduction by a reducing agent.

The solvent to be used when catalytic reduction with a hydrogen gas is carried out is not particularly limited so long as it is inert to the above reaction, and may include, for example, alcohols such as methanol, ethanol, propanol, isopropanol, butanol, etc.; ethers such as diethyl ether, tetrahydrofuran, dioxane, etc.; water; and acetic acid. Preferred are the above alcohols. When the compound (IIb), (IIc), (IIIb) or (IIIc) is not easily dissolved in the above solvent, dissolution can be accelerated by a method of mixing these solvents, adding a small amount of hydrochloric acid, etc., whereby the reaction can be accelerated.

As the catalyst to be used, there may be mentioned, for example, a noble metal type catalyst such as platinum oxide, palladium-carbon, platinum-carbon, etc., preferably platinum oxide and palladium-carbon. The amount of the catalyst to be used is generally 0.01 to 50% by weight, preferably 0.1 to 50% by weight based on the compound (IIb), (IIc), (IIIb) or (IIIc).

The hydrogen gas may be passed to the reaction mixture at normal pressure or may be reacted in an autoclave under pressurization up to 100 kg/cm². The pressure is preferably normal pressure to 50 kg/cm².

The reaction temperature is 0° to 200° C., preferably the reaction is carried out in the range of 0° to 150° C. The reaction time varies depending on conditions other than those described above, but the reaction is carried out generally for 10 minutes to 24 hours, preferably for 15 minutes to 12 hours.

On the other hand, when reduction is carried out by using a reducing agent, as the reducing agent, preferred is a reducing agent used for reduction of an αβ-unsaturated ketone, such as metallic lithium-ammonia, triethylsilane-trifluoroacetic acid, triphenyltin hydride, lithium aluminum hydride-cuprous iodide, etc. These reactions can be carried out, for example, under conditions described in "New Experimental Chemistry Lecture" edited by the Japan Chemical Society, vol. 14 (I), p. 5.

[Preparation process 4-1]
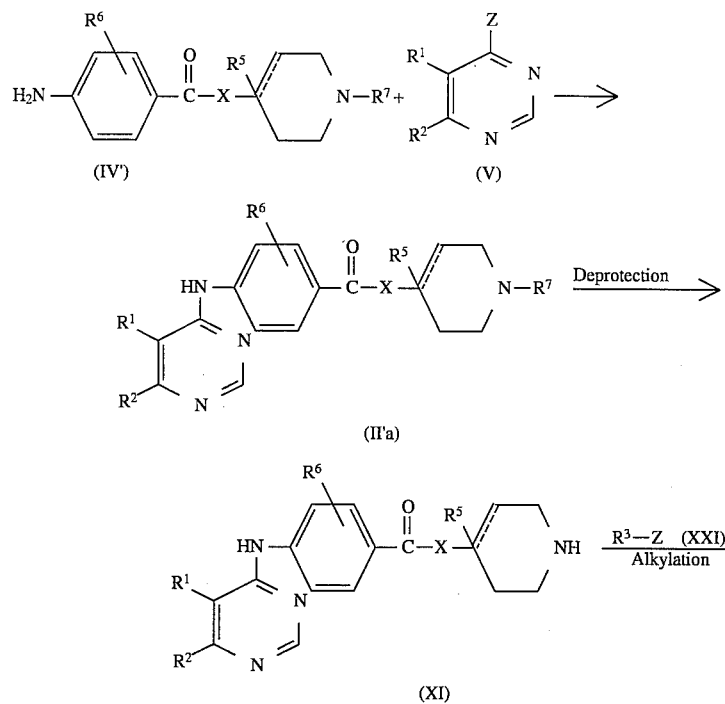
[Preparation process 4-2]
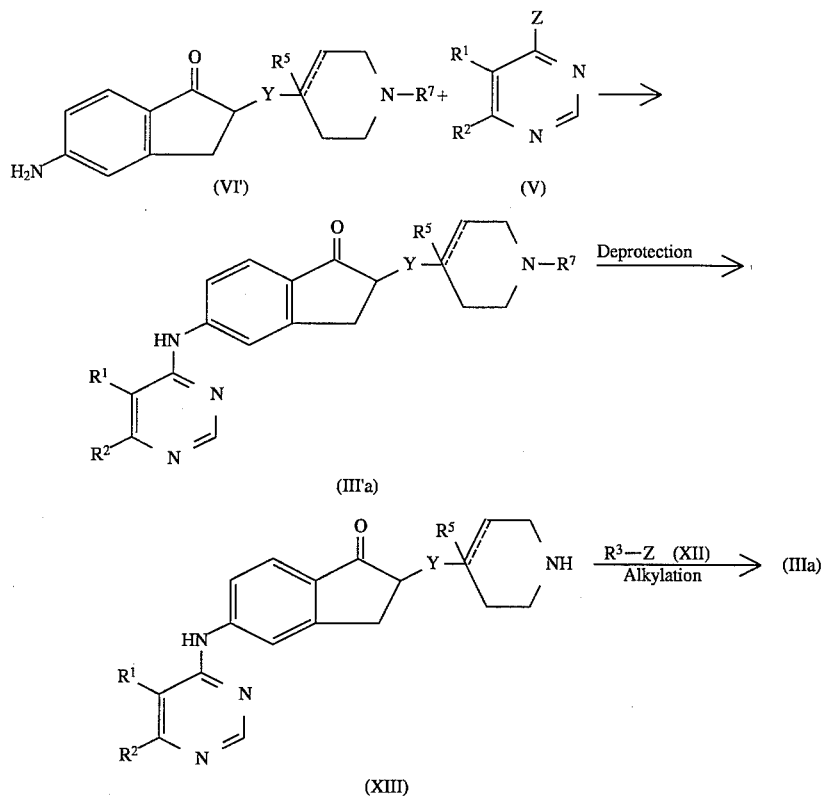
(wherein $R^1$, $R^2$, $R^3$, $R^5$, $R^6$ X, Y, Z and ⋯ have the same meanings as described above and $R^7$ represents a protective group such as a t-butoxycarbonyl group, a benzyloxycarbonyl group, an acetyl group, a trifluoroacetyl group, a benzoyl group, a triphenylmethyl group and a methoxymethyl group)

In [Preparation process 4-1] or [Preparation process 4-2], the compound (IIa) or (IIIa) can be also prepared by reacting the compound (IV') or (VI') having the protective group $R^7$ with the compound (V) to prepare the compound (II'a) or (III'a), removing the protective group and then carrying out alkylation.

The protective group $R^7$ may be any protective group generally used as a protective group for an amino group, and there may be mentioned, for example, a protective group such as a t-butoxycarbonyl group, a benzyloxycarbonyl group, an acetyl group, a trifluoroacetyl group, a benzoyl group, a triphenylmethyl group and a methoxymethyl group.

The reactions for obtaining the compound (II'a) from the compounds (IV') and (V) and the compound (III'a) from the compounds (VI') and (V) can be carried out according to the same method as described above in [Preparation process 1-1] and [Preparation process 1-2].

The deprotection reaction for obtaining the compound (XI) from the compound (II'a) or the compound (XIII) from the compound (III'a) can be carried out by suitably selecting from methods described in literature (e.g. T. W. Greene, "Protective Groups in Organic Synthesis" John Wiley & Sons), for example, a method using an acid, an alkali or hydrogen reduction, etc.

In the alkylation reactions for obtaining the compound (IIa) from the compound (XI) and the compound (IIIa) from the compound (XIII), the solvent to be used is not particularly limited so long as it is inert to the above reactions, and may include, for example, ketones such as acetone, methyl ethyl ketone, etc.; ethers such as diethyl ether, tetrahydrofuran, dioxane, etc.; alcohols such as methanol, ethanol, propanol, isopropanol, butanol, etc.; aprotic polar solvents such as dimethylformamide, dimethyl sulfoxide, dimethylacetamide, hexamethylphosphoric acid triamide, etc.; halogenated hydrocarbons such as chloroform, dichloromethane, dichloroethane, etc. and others.

It is generally desired to carry out the above reactions in the presence of a base. As the base, there may be mentioned alkali metal carbonates such as sodium carbonate, potassium carbonate, etc.; and amines such as triethylamine, tributylamine, diisopropylethylamine, pyridine, picoline, etc.

The reaction temperature is 0° to 150° C., preferably the reaction is carried out in the range of 0° to 100° C. The reaction time is generally 15 minutes to 72 hours, preferably the reaction is carried out for 30 minutes to 24 hours.

[Preparation process 5-1]

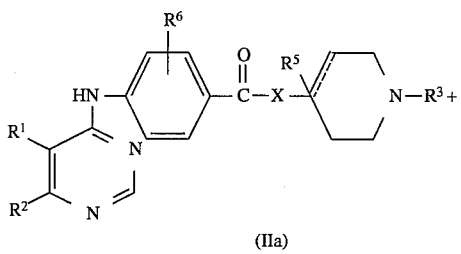

(IIa)

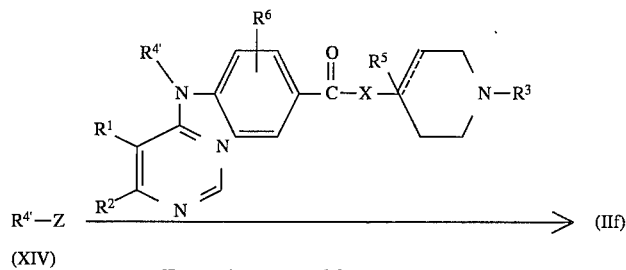

[Preparation process 5-2]

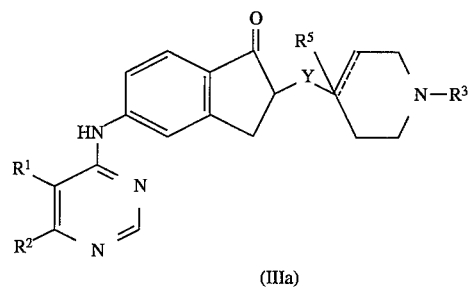

(IIIa)

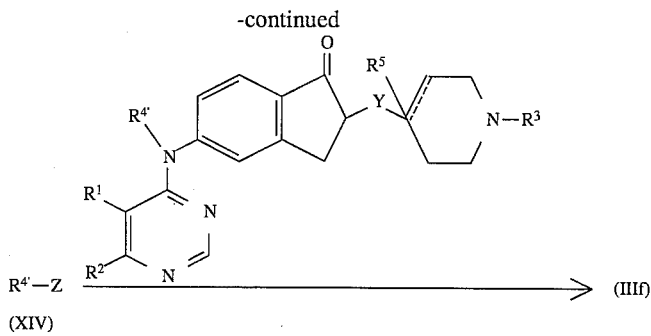

(XIV) → (IIIf)

(wherein $R^1, R^2, R^3, R^5, R^6, X, Y, Z$ and $\overline{\cdots}$ have the same meanings as described above and $R^{4'}$ represents the same acyl group described in $R^4$)

In [Preparation process 5-1] or [Preparation process 5-2], the compound (IIf) or (IIIf) is prepared by reacting the compound (IIa) or (IIIa) with the acyl halide (XIV) in a 1- to 5-fold molar amount, preferably a 1- to 2-fold molar amount in the presence of a base.

The solvent to be used is not particularly limited so long as it is inert to the above reactions, and may include, for example, halogenated hydrocarbons such as methylene chloride, chloroform, dichloroethane, etc.; aprotic polar solvents such as dimethylformamide, dimethyl sulfoxide, dimethylacetamide, hexamethylphosphoric acid triamide, etc.; esters such as ethyl acetate, etc.; and nitriles such as acetonitrile, etc. Preferred are halogenated hydrocarbons and aprotic polar solvents.

As the base to be used, there may be mentioned amines such as triethylamine, tributylamine, diisopropylethylamine, pyridine, picoline, lutidine, etc.; alkali metal carbonates such as sodium carbonate, potassium carbonate, etc. and others. Preferred are amines. The amount to be used is generally a 1- to 10-fold molar amount, preferably a 1- to 5-fold molar amount based on the acyl halide.

The reaction temperature is −70° to 150° C., preferably the reaction is carried out in the range of −50° to 100° C. The reaction time varies depending on conditions, but the reaction is carried out generally for 15 minutes to 100 hours, preferably for 30 minutes to 72 hours.

In the compound (II) or (III), when at least one of $R^1$, $R^2$ and $R^3$ has a functional group such as a hydroxy group, an amino group, etc., these can be converted into an acyloxy group, an acylamino group, etc., respectively, according to a known method, for example, by subjecting it to acylation reaction. When it has a nitro group, it can be converted into an amino group by reduction reaction.

The compounds (VIII) and (IX) to be used in the above [Preparation process 2-1] and [Preparation process 2-2] are known compounds or compounds easily prepared from known compounds according to a conventional method.

The compounds (V), (VII) and (X) to be used as starting materials in [Preparation process 1-1], [Preparation process 1-2], [Preparation process 2-1], [Preparation process 2-2], [Preparation process 4-1] and [Preparation process 4-2] can be prepared easily according to known methods (see Japanese Provisional Patent Publication No. 203072/1982 and Japanese Provisional Patent Publication No. 70/1987). The compounds (IV), (VI), (IV') and (VI') to be used as starting materials in [Preparation process 1-1], [Preparation process 1-2], [Preparation process 4-1] and [Preparation process 4-2] can be prepared by [Preparation process 6-1], [Preparation process 6-2], [Preparation process 8-1], [Preparation process 8-2], [Preparation process 9-1] and [Preparation process 9-2] shown below.

[Preparation process 6-1]

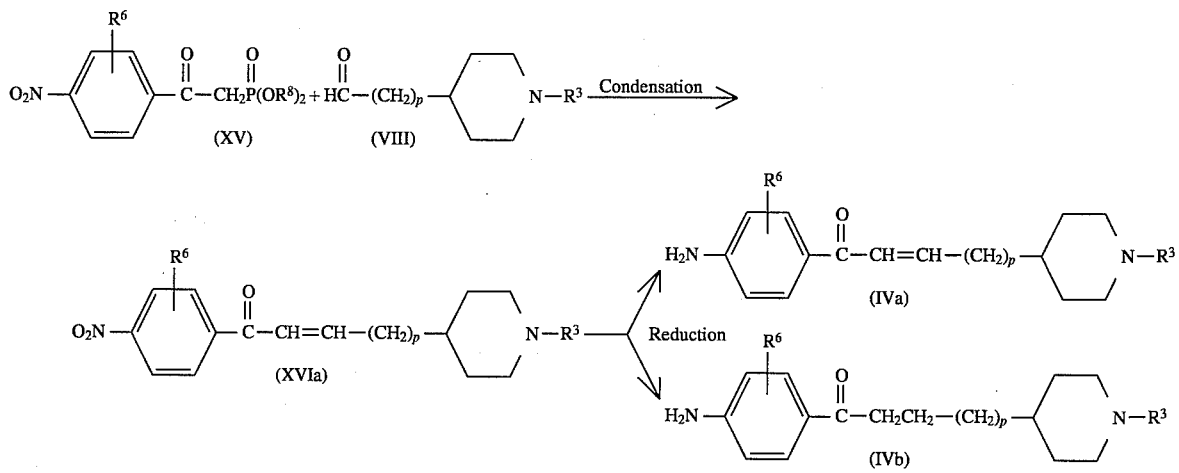

[Preparation process 6-1]
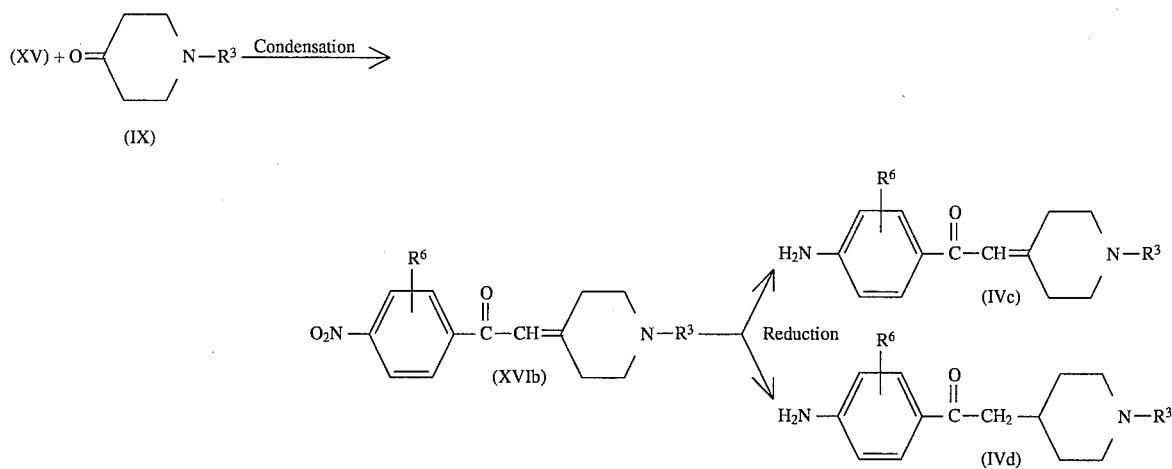
(wherein $R^3$, $R^6$ and p have the same meanings as described above and $R^8$ represents a methyl group, an ethyl group or a phenyl group)
[Preparation process 6-2]
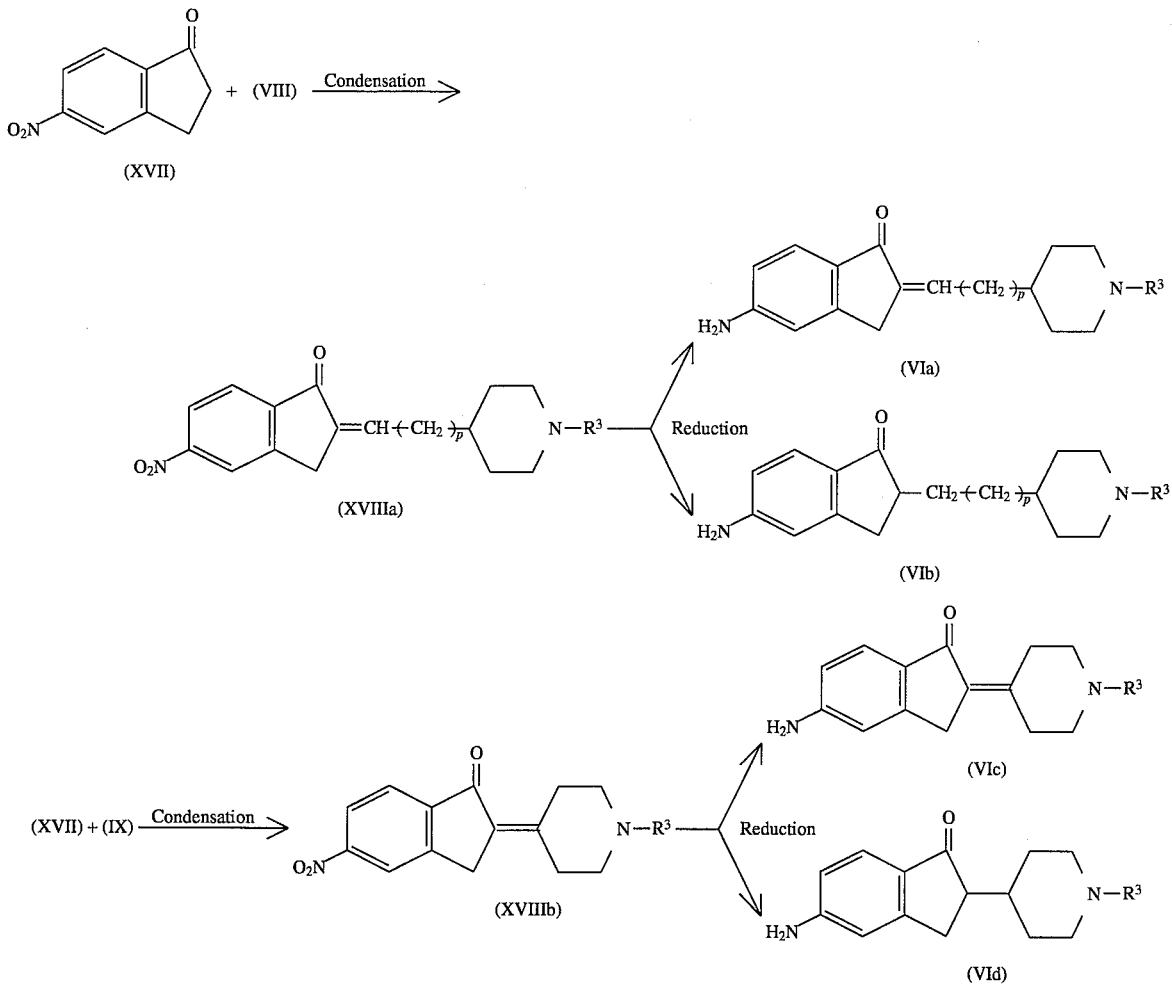

(wherein $R^3$ and p have the same meanings as described above)

The condensation reactions of [Preparation process 6-1] and [Preparation process 6-2] are carried out by the same methods as described above in [Preparation process 2-1] and [Preparation process 2-2], or carried out by a known method known as the Horner-Wadsworth-Emmons reaction (see, for example, M. A. Blanchette et at., Tetrahedron Letters, vol. 25, 2183).

In the reduction reactions of [Preparation process 6-1] and [Preparation process 6-2], partial reduction reactions for obtaining the compound (IVa) from the compound (XVIa), the compound (IVc) from the compound (XVIb), the compound (VIa) from the compound (XVIIIa) and the compound (VIc) from the compound (XVIIIb) are carried out by a method of using stannous chloride, tin, zinc or iron, preferably stannous chloride or tin under acidic conditions or using zinc under neutral or alkaline conditions. As the solvent to be used for these reactions, there may be mentioned, in addition to alcohols such as methanol, ethanol, propanol, etc., acetonitrile, acetic acid, water, etc. Preferred are alcohols, acetic acid and water. These may be used as a mixture. Further, as the acid to be used, there may be mentioned mineral acids such as hydrochloric acid, sulfuric acid and phosphoric acid or organic acids such as acetic acid and propionic acid. Preferred are hydrochloric acid, sulfuric acid and acetic acid. As the alkali, there may be mentioned an alkali metal hydroxide such as sodium hydroxide and potassium hydroxide. The reactions are carried out generally at a temperature of 0° to 200° C., preferably in the range of 0° to 150° C. for 30 minutes to 72 hours, preferably 1 hour to 24 hours.

On the other hand, in the reduction reactions of [Preparation process 6-1] and [Preparation process 6-2], simultaneous reduction reactions of nitro groups and double bonds for obtaining the compound (Ivb) from the compound (XVIa), the compound (IVd) from the compound (XVIb), the compound (VIb) from the compound (XVIIIa) and the compound (VId) from the compound (XVIIIb) are carried out by the same methods as described above in [Preparation process 3-1] and [Preparation process 3-2].

The nitro compounds (XVIa), (XVIb), (XVIIIa) and (XVIIIb) which are intermediates in [Preparation process 6-1] and [Preparation process 6-2] and the compounds (IV') (i.e., IV'a, IV'b, IV'c and IV'd) and the compounds (VI') (i.e., VI'a, VI'b, VI'c and VI'd) which are starting materials in [Preparation process 4-1] and [Preparation process 4-2] can be also prepared by [Preparation process 7-1] and [Preparation process 7-2] shown below.

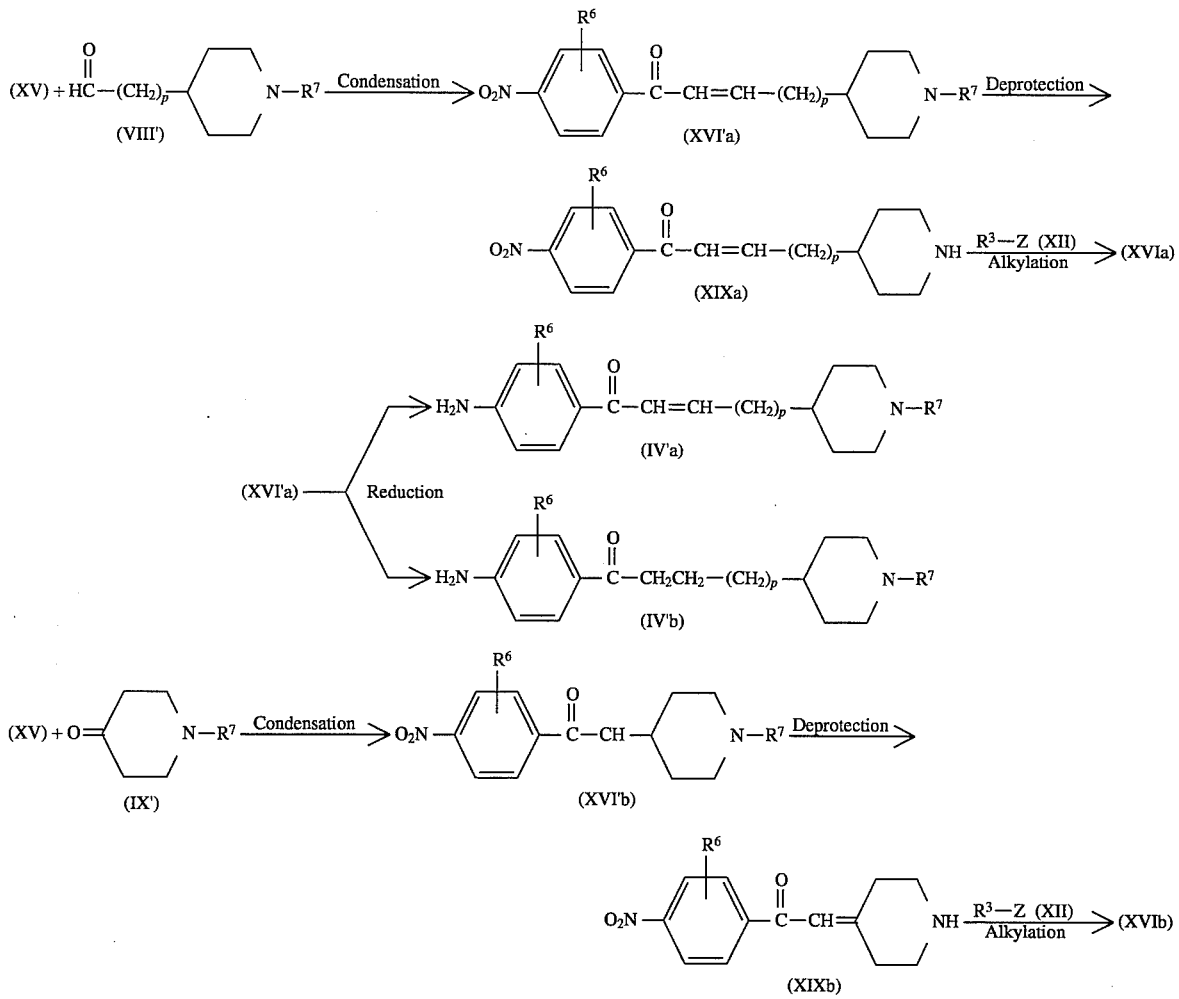

-continued
[Preparation process 7-1]
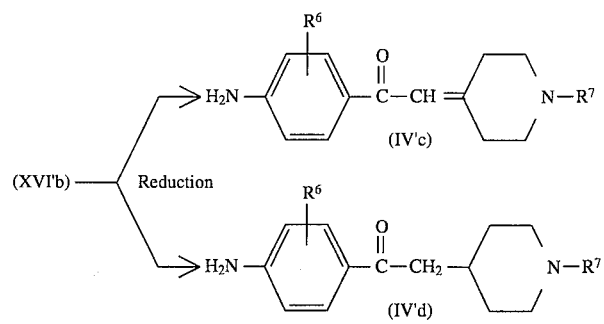
(wherein $R^3$, $R^6$, $R^7$, Z and p have the same meanings as described above)
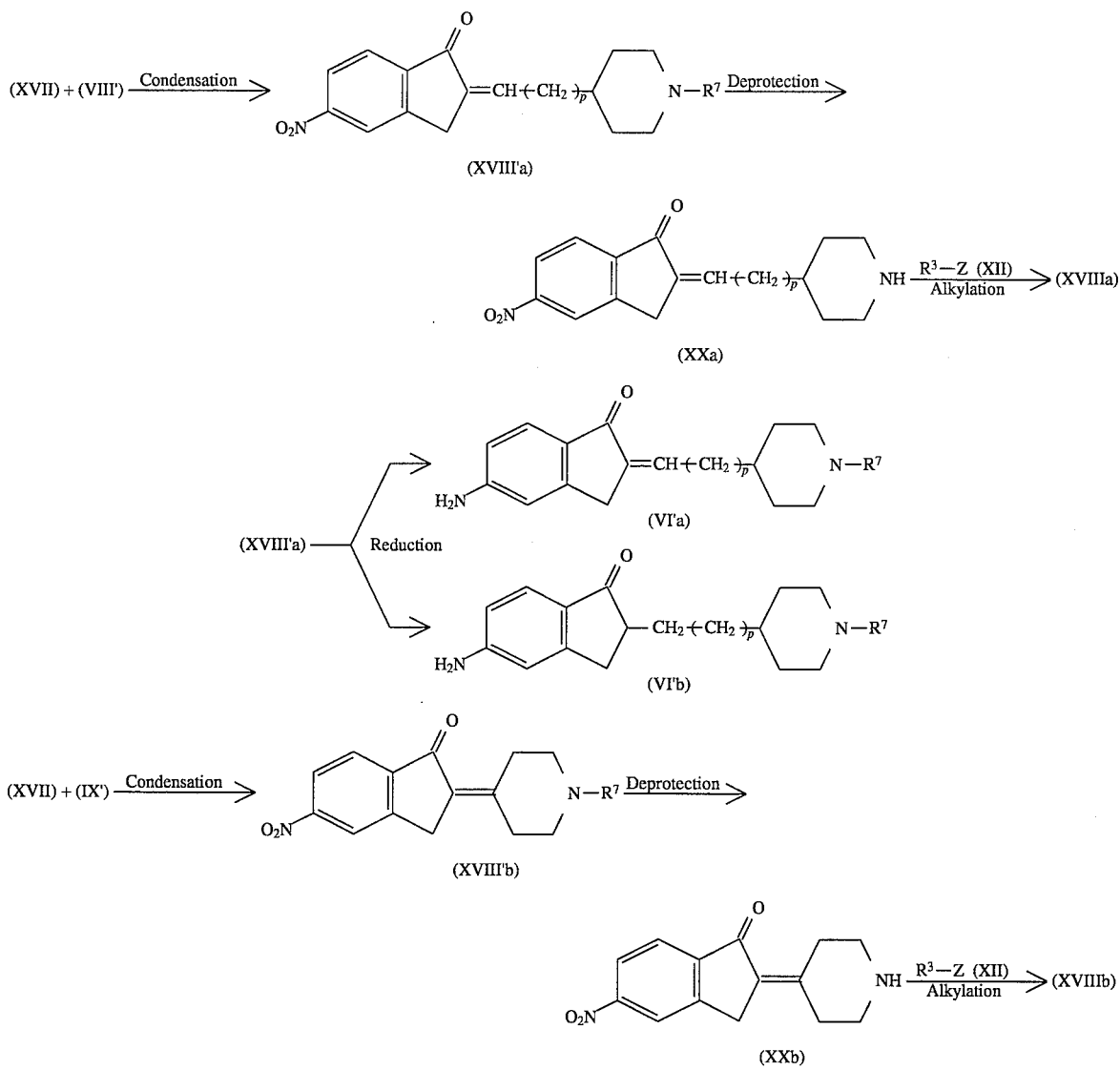

-continued
[Preparation process 7-2]

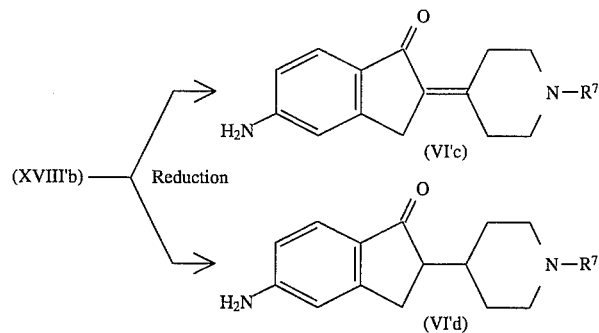

(wherein $R^3$, $R^7$ and p have the same meanings as described above)

The condensation reactions of [Preparation process 7-1] and [Preparation process 7-2] are carried out by the same methods as described above in [Preparation process 6-1] and [Preparation process 6-2], and the deprotection reactions are carried out in the same manner as in [Preparation process 4-1] and [Preparation process 4-2], by suitably selecting a known method of using an acid, an alkali or hydrogen reduction, etc. Also, the N-alkylation reaction by the compound (XII) is carried out by the same methods as described above in [Preparation process 4-1] and [Preparation process 4-2], and the reduction reactions of the compounds (XVI'a), (XVI'b), (XVIII'a) and (XVIII'b) can be carried out by the same methods as described above in [Preparation process 6-1] and [Preparation process 6-2].

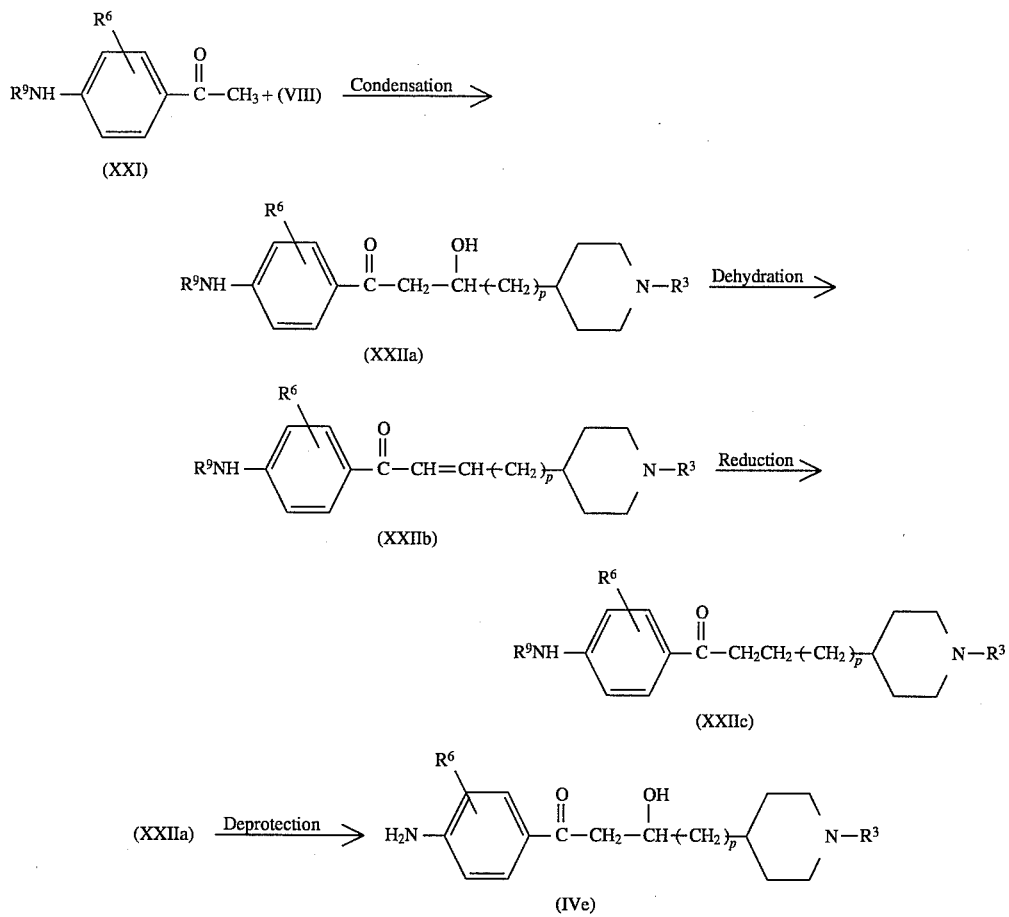

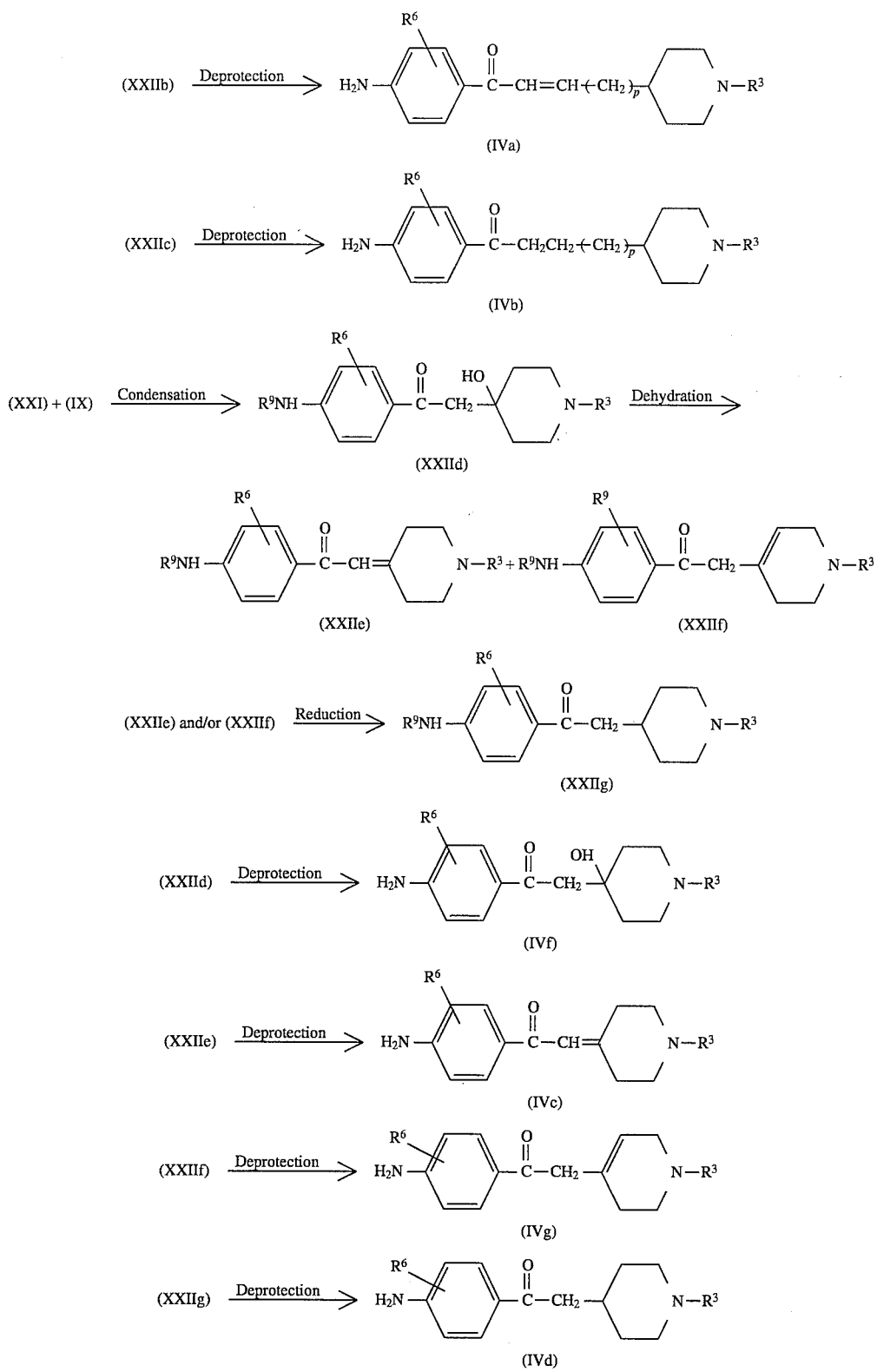
(wherein $R^3$, $R^6$ and p have the same meanings as described above and $R^9$ represents a protective group such as a t-butoxycarbonyl group, a benzyloxycarbonyl group, an acetyl group, a trifluoroacetyl group and a benzoyl group)

[Preparation process 8-2]
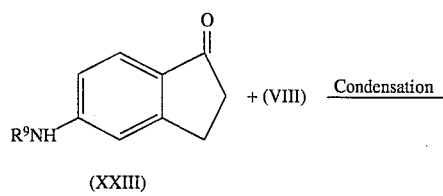
(XXIII) + (VIII) →<sup>Condensation</sup>
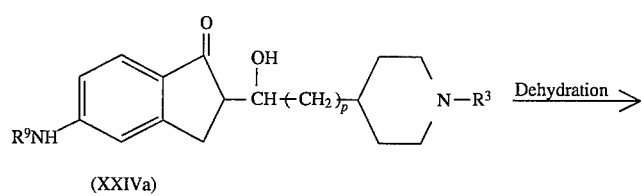 →<sup>Dehydration</sup>
(XXIVa)
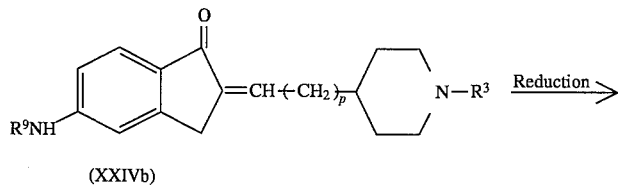 →<sup>Reduction</sup>
(XXIVb)
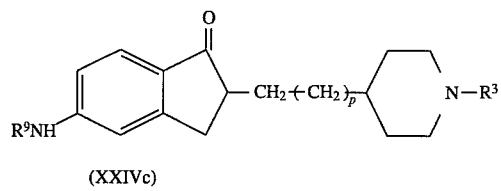
(XXIVc)
(XXIVa) →<sup>Deprotection</sup> 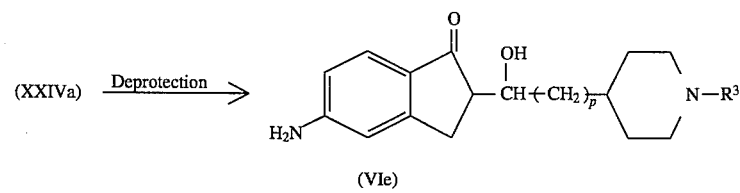
(VIe)
(XXIVb) →<sup>Deprotection</sup> 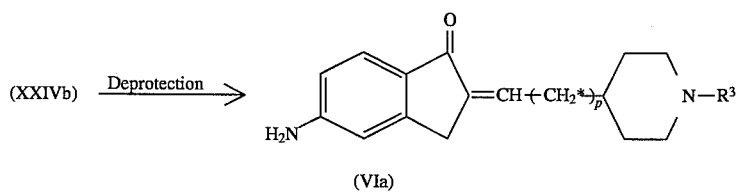
(VIa)
(XXIVc) →<sup>Deprotection</sup> 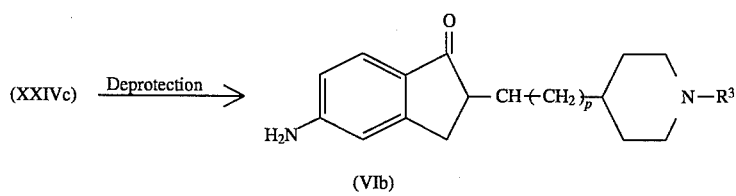
(VIb)
(XXIII) + (IX) →<sup>Condensation</sup> 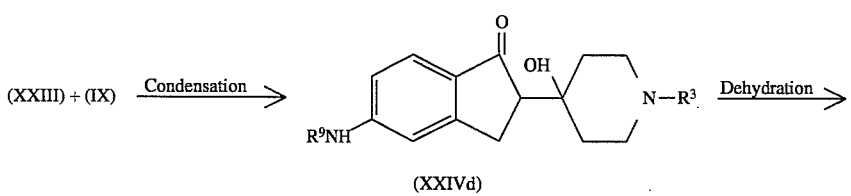 →<sup>Dehydration</sup>
(XXIVd)

-continued
[Preparation process 8-2]

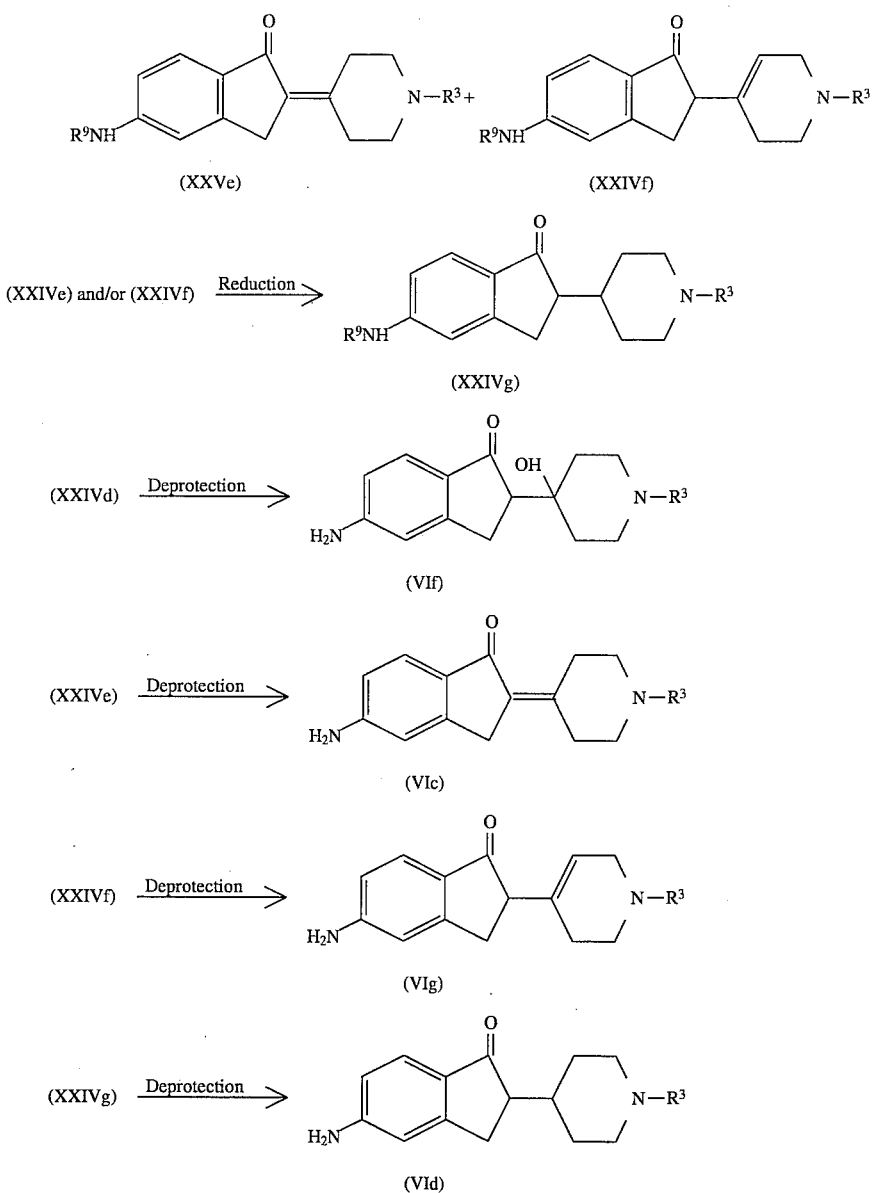

(wherein $R^3$, $R^9$ and p have the same meanings as described above)

In [Preparation process 8-1] or [Preparation process 8-2], the compound (XXIIa), (XXIId), (XXIVa) or (XXIVd) is prepared by subjecting the compound (XXI) or (XXIII) with the compound (VIII) or (IX) in a 1- to 5-fold molar amount, preferably a 1- to 2-fold molar amount to condensation reaction in a solvent in the presence of a strong base.

$R^9$ as the protective group is not particularly limited so long as it is stable under these reaction conditions, and preferred are a t-butoxycarbonyl group, a benzyloxycarbonyl group, an acetyl group, a trifluoroacetyl group, a benzoyl group, etc.

As the solvent to be used, there may be mentioned ethers such as diethyl ether, diisopropyl ether, tetrahydrofuran, dioxane, etc.; aliphatic and aromatic hydrocarbons such as pentane, hexane, cyclohexane, benzene, toluene, etc.; and aprotic polar solvents such as hexamethylphosphoric acid triamide, dimethyl sulfoxide, etc. Also, a mixture of these solvents may be used.

As the strong base to be used, preferred are alkyl lithiums such as n-butyl lithium, t-butyl lithium, etc.; alkali metal amides such as lithium diisopropylamide, lithium ditrimethylsilylamide, sodium amide, etc.; and alkali metal hydrides such as sodium hydride, potassium hydride, etc. The amount to be used is generally a 1- to 5-fold molar amount, preferably a 2- to 3-fold molar amount based on the compound (XXI) or (XXIII).

The reaction temperature is $-70°$ to $100°$ C., preferably the reaction is carried out in the range of $-70°$ to $50°$ C.

The dehydration reactions of [Preparation process 8-1] and [Preparation process 8-2] are generally carried out by suitably selecting from various known methods used when an olefin is synthesized from an alcohol. There may be mentioned, for example, a dehydration method under acidic conditions using an inorganic acid such as hydrochloric acid, sulfuric acid, phosphoric acid, etc.; or an organic acid such as p-tolunesulfonic acid, benzenesulfonic acid, etc., or a dehydration method in the coexistence of a dehydrating agent such as thionyl chloride, phosphorus oxychloride, methanesulfonic acid chloride, methanesulfonic anhydride, acetic anhydride, etc. and an organic base such as pyridine, picoline, lutidine, 1,8-diazabicyclo[5.4.0.]-7-undecene, triethylamine, etc. Particularly when the protective group $R^9$ is unstable under acidic conditions, the latter method is preferred.

In the above dehydration reactions, as in the examples of the compounds (XXIIe) and (XXIIf), and (XXIVe) and (XXIVf), isomers having the double bond at different positions may be produced. These may be separated and used or may be used as a mixture when they are used for the reduction reactions.

The reduction reactions of [Preparation process 8-1] and [Preparation process 8-2] are carried out by the same methods as described above in [Preparation process 3-1] and [Preparation process 3-2].

By deprotecting the above compounds (XXIIa), (XXIIb), (XXIIc), (XXIId), (XXIIe), (XXIIf), (XXIIg), (XXIVa), (XXIVb), (XXIVc), (XXIVd), (XXIVe), (XXIVf) and (XXIVg), the compounds (IVe), (IVa), (IVb), (IVf), (IVc), (IVg), (IVd), (VIe), (VIa), (VIb), (VIf), (VIc), (VIg) and (VId) are prepared, respectively. The deprotection reactions are carried out by the same methods as described above in [Preparation process 4-1] and [Preparation process 4-2].

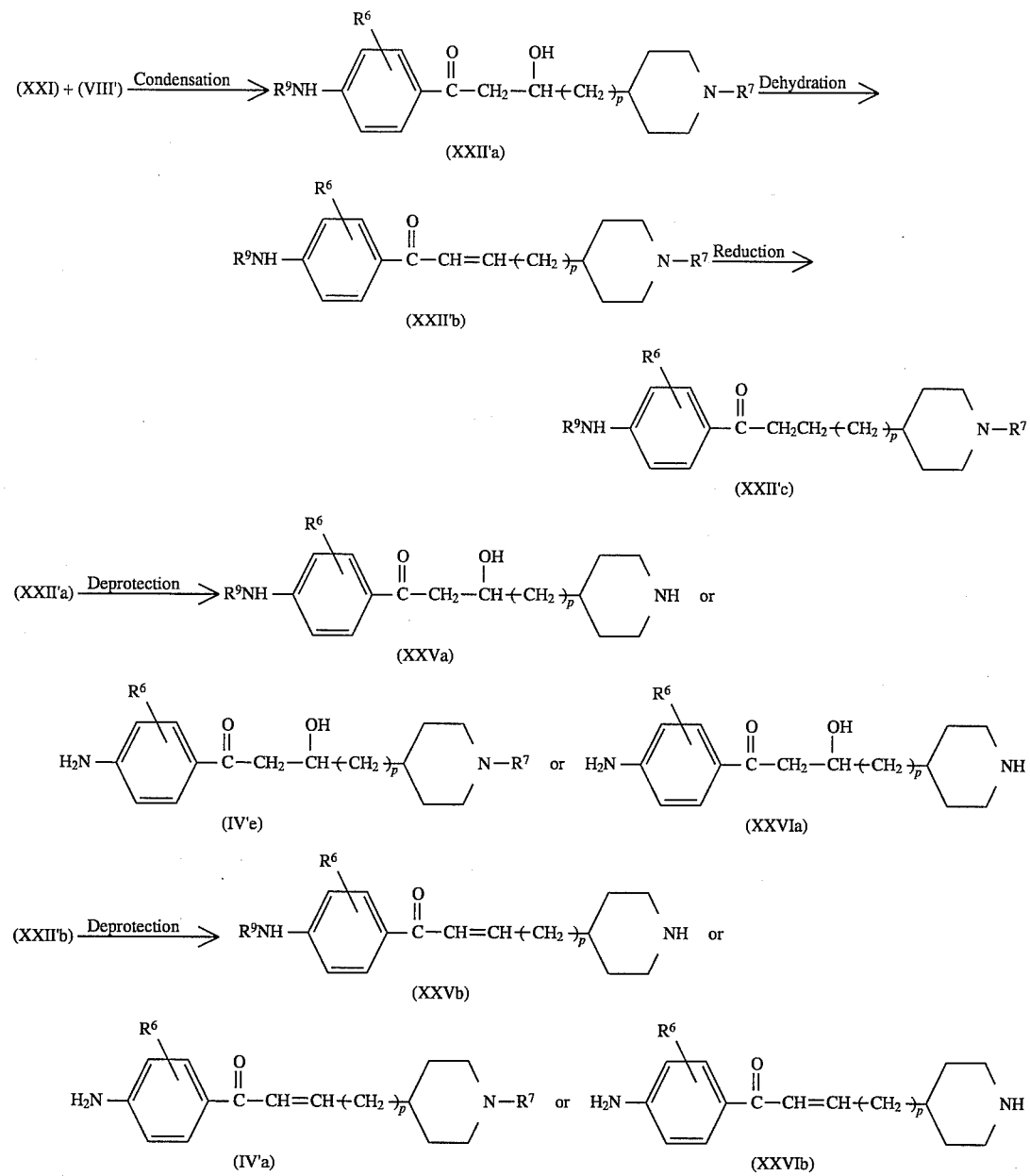

-continued
[Preparation process 9-1]
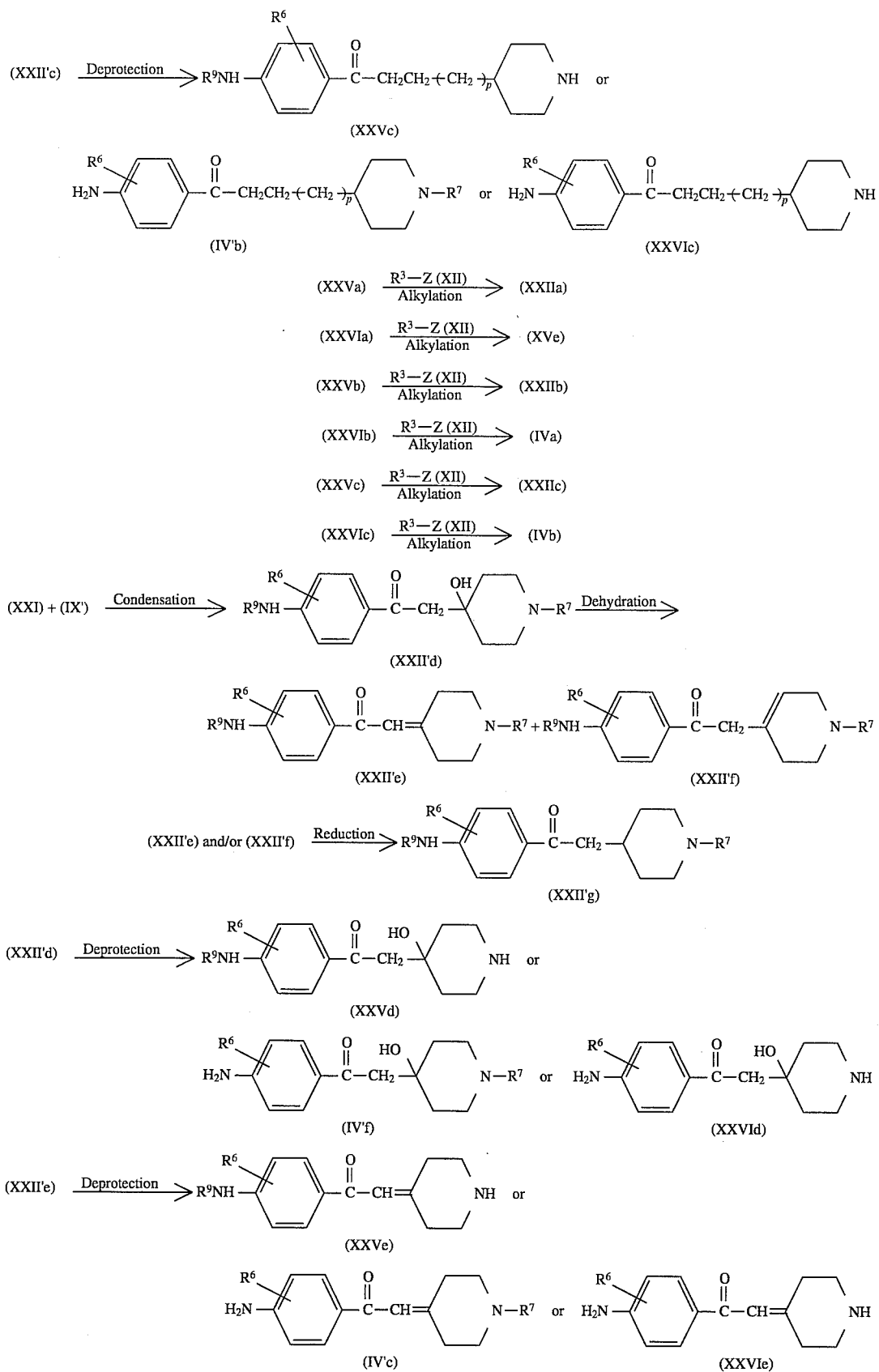

-continued
[Preparation process 9-1]
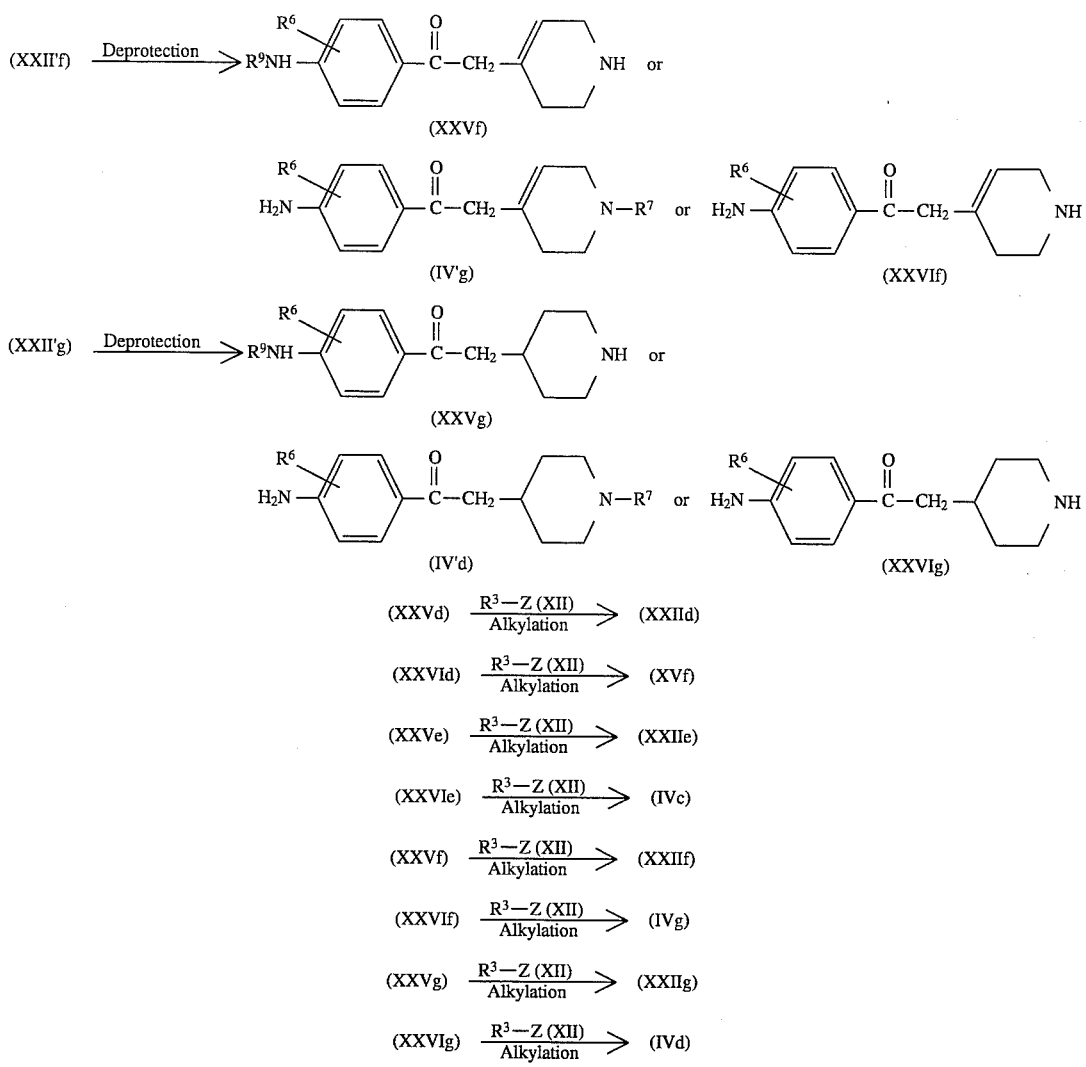
(wherein $R^3$, $R^6$, $R^7$, $R^9$, Z and p have the same meanings as described above)
[Preparation process 9-2]
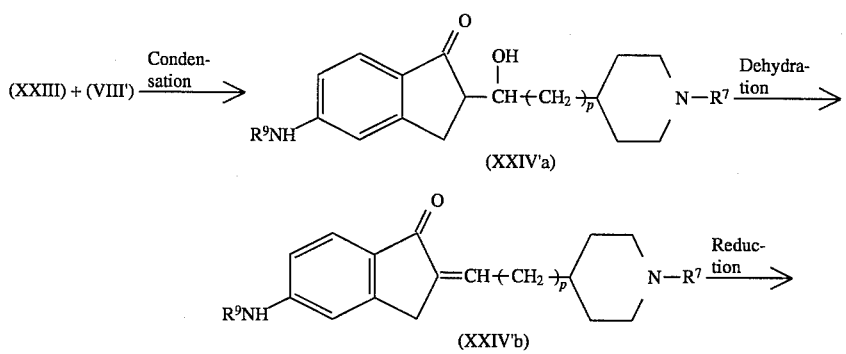

-continued
[Preparation process 9-2]

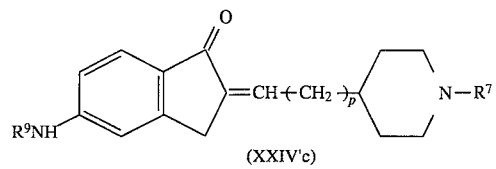
(XXIV'c)

(XXIV'a) →Deprotection→ 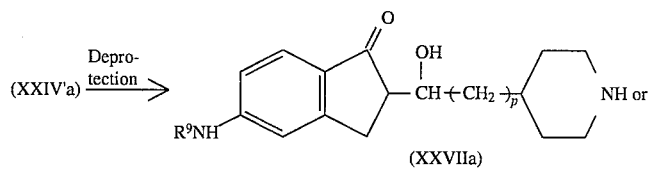
(XXVIIa)

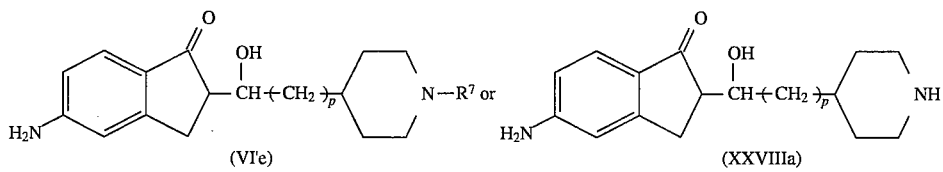
(VI'e)    (XXVIIIa)

(XXIV'b) →Deprotection→ 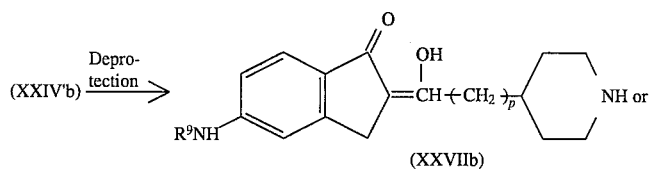
(XXVIIb)

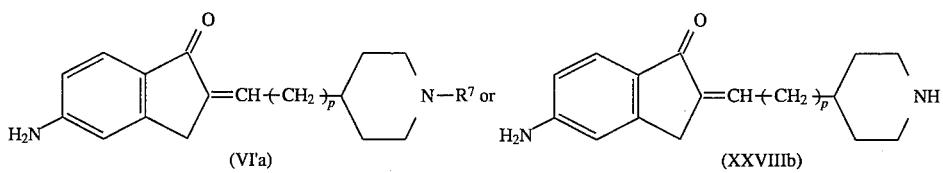
(VI'a)    (XXVIIIb)

(XXIV'c) →Deprotection→ 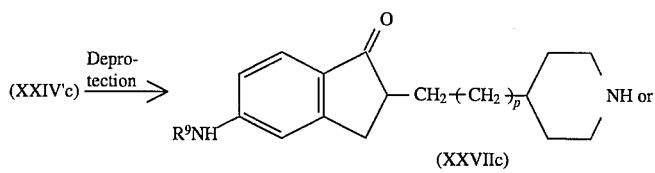
(XXVIIc)

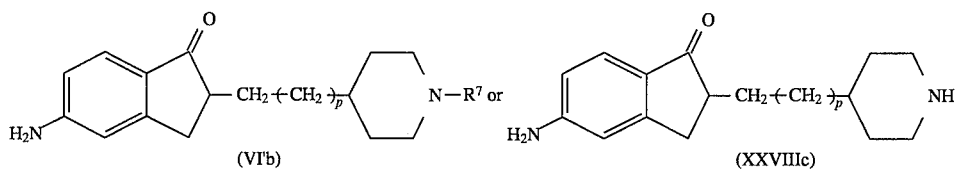
(VI'b)    (XXVIIIc)

(XXVIIa) $\xrightarrow{R^3-Z\ (XII)}{Alkylation}$ (XXIVa)

(XXVIIIa) $\xrightarrow{R^3-Z\ (XII)}{Alkylation}$ (VIe)

(XXVIIb) $\xrightarrow{R^3-Z\ (XII)}{Alkylation}$ (XXIVb)

(XXVIIIb) $\xrightarrow{R^3-Z\ (XII)}{Alkylation}$ (VIa)

(XXVIIc) $\xrightarrow{R^3-Z\ (XII)}{Alkylation}$ (XXIVc)

(XXVIIIc) $\xrightarrow{R^3-Z\ (XII)}{Alkylation}$ (VIb)

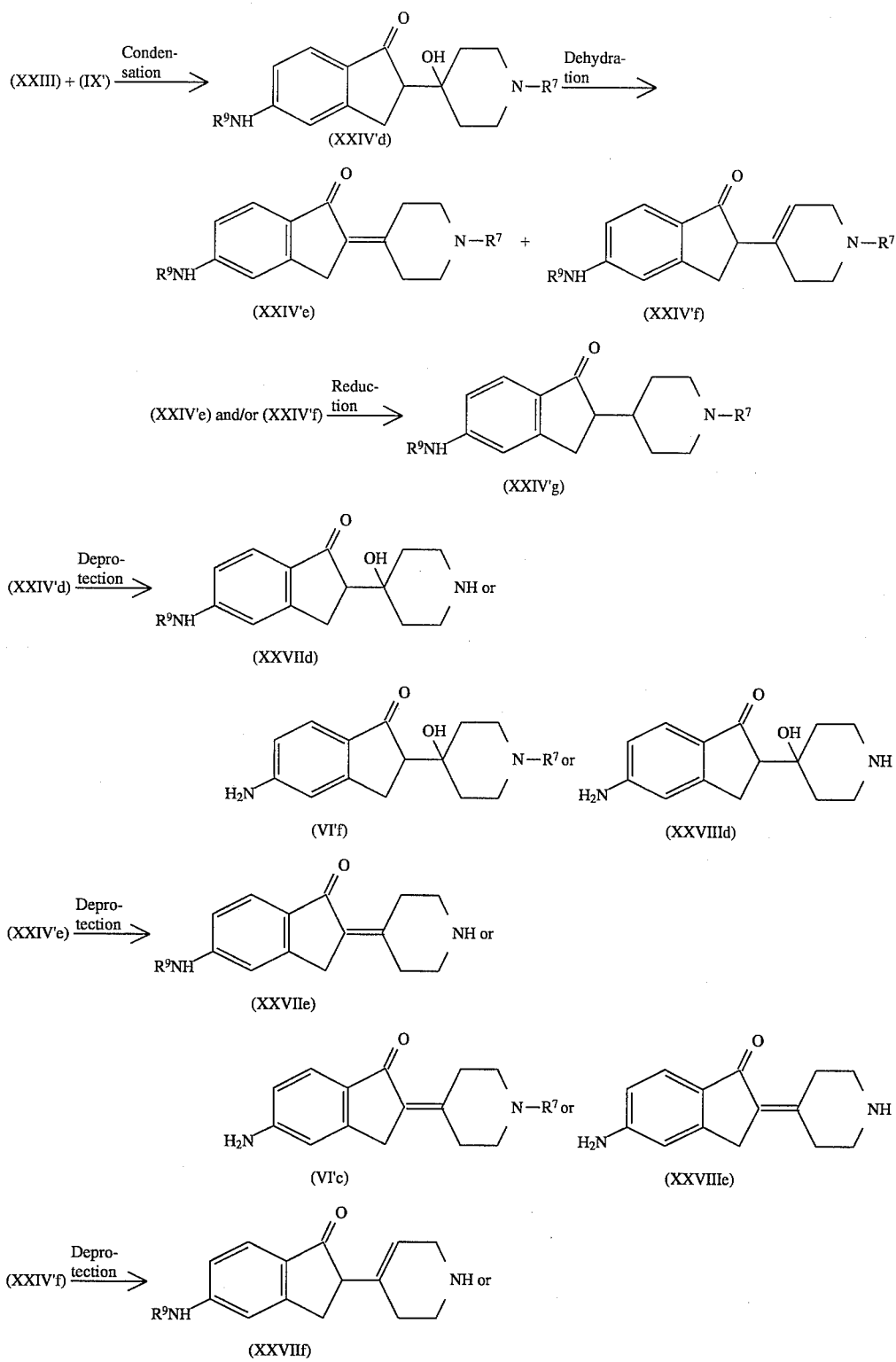

-continued
[Preparation process 9-2]

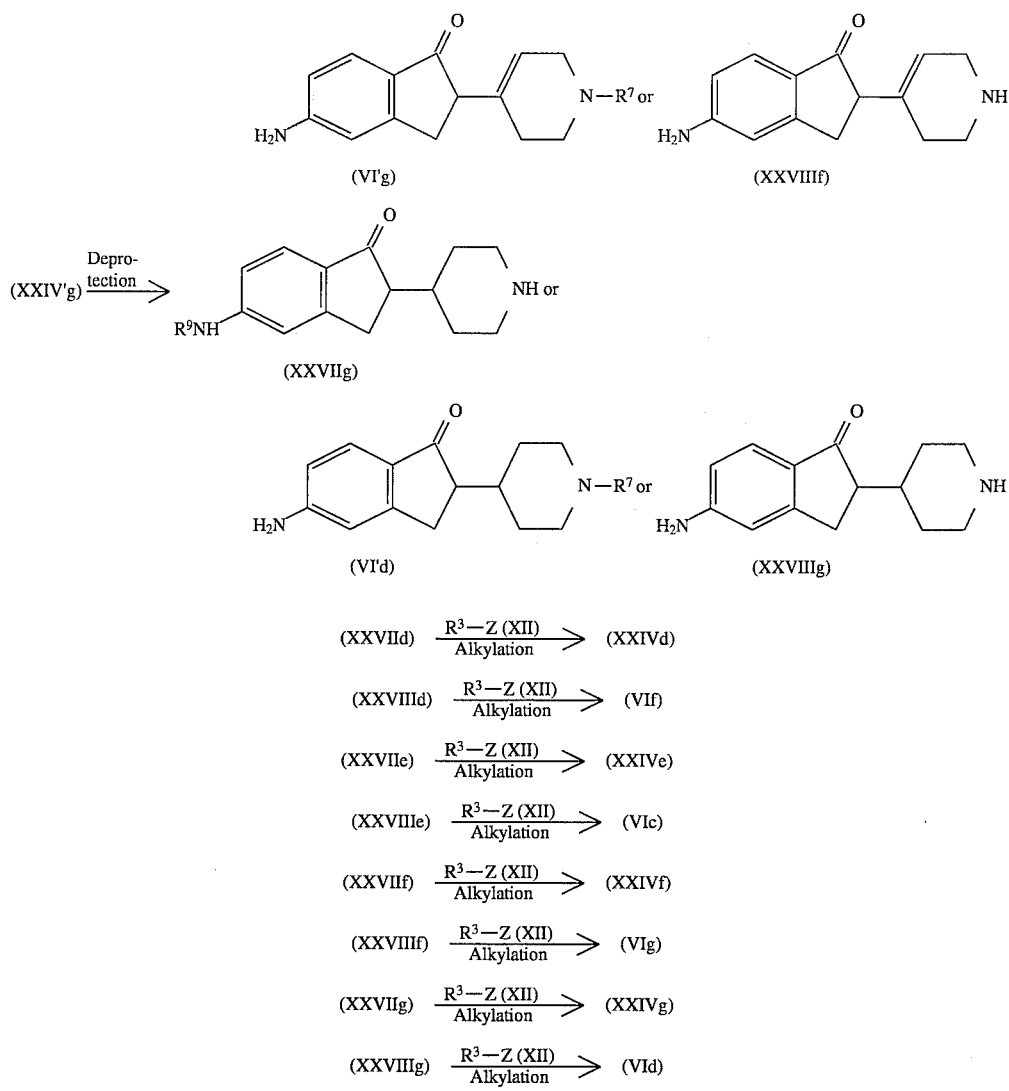

(wherein $R^3$, $R^6$, $R^7$, $R^9$, Z and p have the same meanings as described above)

In [Preparation process 9-1] and [Preparation process 9-2], the condensation reactions, dehydration reactions and reduction reactions are carried out by the same methods as described in [Preparation process 8-1] and [Preparation process 8-2].

$R^7$ and $R^9$ as protective groups may be different or may be the same. The respective compounds obtained in the respective reactions of [Preparation process 9-1] and [Preparation process 9-2] are supplied to the deprotection reactions, respectively. In this case, by suitably selecting the kinds of the two protective groups $R^7$ and $R^9$ or suitably selecting deprotection conditions, either one of $R^7$ and $R^9$ can be selectively removed. Also, both of them can be removed simultaneously. The selections of these $R^7$ and $R^9$ and deprotection conditions can be carried out by referring to literature, for example, T. W. Greene, "Protective Groups in Organic Synthesis" John Wiley & Sons.

The compounds (XXVa), (XXVIa), (XXVb), (XXVIb), (XXVc), (XXVIc), (XXVd), (XXVId), (XXVe), (XXVIe), (XXVf), (XXVIf), (XXVg), (XXVIg), (XXVIIa), (XXVIIIa), (XXVIIb), (XXVIIIb), (XXVIIc), (XXVIIIc), (XXVIId), (XXVIIId), (XXVIIe), (XXVIIIe), (XXVIIf), (XXVIIIf), (XXVIIg) and (XXVIIIg) thus obtained can be converted into (XXIIa), (IVe), (XXIIb), (IVa), (XXIIc), (IVb), (XXIId), (IVf), (XXIIe), (IVc), (XXIIf), (IVg), (XXIIg), (IVd), (XXIVa), (VIe), (XXIVb), (VIa), (XXIVc), (VIb), (XXIVd), (VIf), (XXIVe), (VIc), (XXIVf), (VIg), (XXIVg) and (VId), respectively, by subjecting to alkylation using the compound (XII) ($R^3$-Z) by the same methods as described above in [Preparation process 4-1] and [Preparation process 4-2], respectively.

After completion of the reactions, the desired compounds of the respective reactions can be obtained by treating the reaction mixtures according to a conventional method and further can be purified by using a conventional purification means such as recrystallization, column chromatography, etc., if necessary. The compounds of the formula (I), the formula (II) and the formula (III) of the present invention are converted into desired salts according to a conventional method, if necessary.

In the compounds of the formula (I), the formula (II) and the formula (III) thus prepared, optical isomers or geometric (cis and trans or E and Z) isomers may exist. In that case, by carrying out the above reactions by using starting compounds which are optically resolved or separated as desired, optical isomers or geometric isomers of the corresponding desired compounds can be obtained. Also, by treating a mixture of optical isomers or geometric isomers according to a conventional optical resolution method or separation method, the respective isomers can be obtained.

In the formula (I), the formula (II) and the formula (III), all of optical isomers, geometric isomers and mixtures thereof are represented by the same formulae, but the respective isomers and mixtures thereof are included in the present invention as a matter of course.

BEST MODE FOR PRACTICING THE INVENTION

In the following, the present invention is described in detail by showing Examples, but the scope of the present invention is not limited by these.

EXAMPLE 1

(E)-N-(5,6-dimethylpyrimidin-4-yl)-4-[3-(1-benzyl-piperidin-4-yl)propenoyl]aniline (Compound II-199 in Table 1)

1.27 g of 4-[3-(1-benzylpiperidin-4-yl)propenoyl]-nitrobenzene was added to a mixed solution of 10 ml of acetic acid and 2 ml of hydrochloric acid, and then 1.38 g of stannous chloride was added thereto under ice cooling. The mixture was stirred for 24 hours while further adding 0.69 g of stannous chloride twice during the reaction. The solvent was removed under reduced pressure to obtain a crude product of (E)-4-[3-(1-benzylpiperidin-4-yl)propenoyl]aniline. Then, this was dissolved in 15 ml of ethanol, and to the solution was added 0.67 g of 4-chloro-5,6-dimethylpyrimidine. Subsequently, the mixture was reacted by heating at 60° C. for 30 minutes. The reaction mixture was neutralized by adding a 28% sodium methylate-methanol solution under cooling, solids were removed by filtration, and then the filtrate was consensed under reduced pressure. The obtained residue was applied to silica gel column chromatography to obtain 1.02 g of the title compound as pale yellow powder.

m.p. 188° to 190° C. (decomposed)

Mass; m/z=426 (M$^+$)

NMR ($\delta$, CDCl$_3$); 1.45 to 1.87 (4H, m), 1.96 to 2.13 (2H, m), 2.13 to 2.40 (1H, m), 2.22 (3H, s), 2.49 (3H, s), 2.86 to 3.02 (2H, m), 3.52 (2H, s), 6.62 (1H, s, br), 6.87 (1H, d, J=15.6 Hz), 7.03 (1H, dd, J=15.6 Hz, J=6.5 Hz), 7.18 to 7.43 (5H, m), 7.74 (2H, d, J=8.8 Hz), 7.96 (2H, d, J=8.8 Hz), 8.58 (1H, s)

EXAMPLE 2

N-(5,6-dimethylpyrimidin-4-yl)-4-[3-(1-benzylpiperidin-4-yl)propanoyl]aniline (Compound II-150 in Table 1)

0.82 g of (E)-N-(5,6-dimethylpyrimidin-4-yl)-4-[3-(1-benzylpiperidin-4-yl)propenoyl]aniline obtained in Example 1 was added to a mixed solvent of 30 ml of ethanol and 40 ml of dioxane, and then 0.05 g of platinum oxide was added thereto. The mixture was stirred in a hydrogen stream at room temperature for 3.5 hours. After the catalyst was removed by filtration, the filtrate was condensed under reduced pressure. The obtained residue was applied to silica gel column chromatography to obtain 0.39 g of the title compound as pale yellow powder.

m.p. 168° to 170° C.

Mass; m/z =428 (M$^+$)

NMR ($\delta$, CDCl$_3$); 1.20 to 1.46 (3H, m), 1.60 to 1.85 (4H, m), 1.85 to 2.07 (2H, m), 2.22 (3H, s), 2.49 (3H, s), 2.83 to 3.04 (4H, m), 3.50 (2H, s), 6.60 (1H, s, br), 7.20 to 7.40 (5H, m), 7.72 (2H, d, J=8.8 Hz), 7.96 (2H, d, J=8.8 Hz), 8.58 (1H, s)

EXAMPLE 3

N-(5-chloro-6-methylpyrimidin-4-yl)-4-[3-(1-benzyl-piperidin-4-yl)propanoyl]aniline·2HCl (2HCl salt of Compound II-160 in Table 1)

0.29 g of N- (5-chloro-6-methylpyrimidin-4-yl) -4- [3-(1-benzylpiperidin-4-yl)propanoyl]aniline obtained in the same manner as in Example 1 was dissolved in a mixed solvent of 10 ml of ethyl acetate and 5 ml of ethanol, and a hydrogen chloride gas-saturated ethyl acetate solution was added to the mixture until the pH became 3. Crystals precipitated were collected by filtration and dried to obtain 0.21 g of the title compound as white powder.

(as ½H$_2$O adduct)

m.p. 217° to 220° C.

Mass; m/z=448 (M$^+$)

NMR ($\delta$, CDCl$_3$-DMSO-d$_6$); 1.70 to 1.90 (7H, m), 2.71 (3H, s), 2.82 to 3.23 (4H, m), 3.34 to 3.42 (2H, m), 4.28 (2H, d, J=4.9 Hz), 7.43 to 7.46 (3H, m), 7.67 to 7.69 (2H, m), 7.83 (2H, d, J=8.8 Hz), 8.00 (2H, d, J=8.8 Hz), 8.71 (1H, s), 10.24 (1H, s), 11.15 (1H, s, br)

In the same manner as in Example 1, Example 2 or Example 3, the following compounds were synthesized.

EXAMPLE 4

(E) -N- ( 5-chloro-6-methylpyrimidin-4-yl ) -4-[3-(1-benzylpiperidin-4-yl)propenoyl]aniline (Compound II-162 in Table 1)

White powder m.p. 164° to 166° C.

Mass; m/z=446 (M$^+$)

NMR ($\delta$, CDCl$_3$); 1.49 to 1.70 (2H, m), 1.73 to 1.88 (2H, m), 1.98 to 2.10 (2H, m), 2.18 to 2.36 (1H, m), 2.59 (3H, s), 2.90 to 2.98 (2H, m), 3.52 (2H, s), 6.87 (1H, d, J=15 to 16 Hz), 7.04 (1H, dd, J=15 to 16 Hz, J=6 to 7 Hz), 7.41 (1H, s), 7.79 (2H, d, J=8 to 9 Hz), 7.98 (2H, d, J=8 to Hz), 8.58 (1H, s)

EXAMPLE 5

N-(6-chloropyrimidin-4-yl)-4-[3-(1-benzylpiperidin-4-yl)propanoyl]aniline·HCl (HCl salt of Compound II-146 in Table 1)

(as ½H$_2$O adduct)

Pale yellow powder m.p. 246° to 260° C. (decomposed)

Mass; m/z=434 (M$^+$)

NMR ($\delta$, CDCl$_3$-DMSO-d$_6$); 1.40 to 1.72 (4H, m), 1.72 to 2.03 (3H, m), 2.77 to 3.20 (6H, m), 4.22 (2H, d, J=4.9 Hz), 6.95 (1H, s), 7.38 to 7.49 (3H, m), 7.38 to 7.63 (2H, m), 7.83 ( 2H, d, J=8.8 Hz ), 7.93 ( 2H, d, J=8.8 Hz ), 8.52 (1H, s ), 10.05 (1H, br), 10.28 (1H, s)

EXAMPLE 6

(E)-N-(5,6-dihydro-7H-cyclopenta[d]pyrimidin-4-yl)-4-[3-(1-benzylpiperidin-4-yl)propenoyl]aniline (Compound II-5 in Table 1)

Pale yellow powder m.p. 212° to 214° C.

Mass; m/z=438 (M$^+$)

NMR (δ, CDCl$_3$); 1.46 to 1.87 (4H, m), 1.93 to 2.38 (5H, m), 2.78 to 3.06 (6H, m), 3.52 (2H, s), 6.61 (1H, s, br), 6.87 (1H, d, J=15.6 Hz), 7.04 (1H, dd, J=15.6 Hz, J=6.4 Hz), 7.20 to 7.40 (5H, m), 7.77 (2H, d, J=8.8 Hz), 7.96 (2H, d, J=8.8 Hz ), 8.65 ( 1H, s )

EXAMPLE 7

N-(5,6-dihydro-7H-cyclopenta[d]pyrimidin-4-yl)-4-[3(1-benzylpiperidin-4-yl)propanoyl]aniline (Compound II-2 in Table 1)

Pale yellow powder m.p. 203° to 205° C.

Mass; m/z=440 (M$^+$)

NMR (δ, CDCl$_3$); 1.23 to 1.41 (3H, m), 1.63 to 1.77 (4H, m), 1.88 to 1.99 (2H, m), 2.14 to 2.26 (2H, m), 2.78 to 3.07 (8H, m), 3.49 (2H, s), 6.49 (1H, s), 7.20 to 7.30 (2H, m), 7.20 to 7.26 ( 3H, m), 7.76 (2H, d, J=8.8 Hz), 9.96 (2H, d, J=8.8 Hz ), 8.65 (1H, s )

EXAMPLE 8

N-(5,6-dihydro-7H-cyclopenta[d]pyrimidin-4-yl)-4-[3(1-benzylpiperidin-4-yl)propanoyl]aniline. 2HCl (2HCl salt of Compound II-2 in Table 1)

(as H$_2$O adduct)

Grayish white crystal m.p. 198° to 201° C. (decomposed)

Mass; m/z=440 (M$^+$)

NMR (δ, CDCl$_3$-DMSO-d$_6$); 1.52 to 2.21 (7H, m), 2.20 to 2.42 (2H, m), 2.68 to 3.55 (10H, m), 4.21 (2H, d, J=4.9 Hz), 7.38 to 7.52 (3H, m), 7.60 to 7.80 (2H, m), 7.80 to 8.03 (4H, m), 8.60 (1H, s), 11.53 to 11.80 (1H, m, br)

EXAMPLE 9

(E)-N-(5,6,7,8-tetrahydroquinazolin-4-yl)-4-[3-(1-benzylpiperidin-4-yl)propenoyl]aniline (Compound II-175 in Table 1)

White crystal m.p. 171° to 172° C.

Mass (CI); m/z=453 (M$^+$+1)

NMR (δ, CDCl$_3$); 1.52 to 2.15 (10H, m), 2.18 to 2.36 (1H, m), 2.56 to 2.60 (2H, m), 2.82 to 2.88 (2H, m), 2.92 to 3.13 (2H, m), 3.55 (2H, s), 6.56 (1H, s), 6.87 (1H, d, J=15.6 Hz), 7.04 (1H, dd, J=6.4 Hz, J=15.6 Hz), 7.25 to 7.35 (5H, m), 7.77 (2H, d, J=8.8 Hz), 7.97 (2H, d, J=8.8 Hz), 8.60 (1H, s)

EXAMPLE 10

N-(5,6,7,8-tetrahydroquinazolin-4-yl)-4-[3-(1-benzyl-piperidin-4-yl)propanoyl]aniline (Compound II-163 in Table 1)

(as ¾H$_2$O adduct)

White crystal m.p. 156° to 157° C.

Mass (CI); m/e=455 (M$^+$+1)

NMR (δ, CDCl$_3$); 1.22 to 1.44 (3H, m), 1.61 to 1.74 (4H, m), 1.90 to 2.00 (6H, m), 2.52 to 2.58 (2H, m), 2.79 to 2.98 (6H, m), 3.48 (2H, s), 6.52 (1H, s), 7.25 to 7.32 (5H, m), 7.74 (2H, d, J=8.8 Hz), 7.96 (2H, d, J=8.8 Hz), 8.59 (1H, s)

EXAMPLE 11

(E)-N-(7-methoxy-5,6-dihydro-7H-cyclopenta[d]pyrimidin-4-yl)-4-[3-(1-benzylpiperidin-4-yl)propenoyl]aniline (Compound II-173 in Table 1)

(as ¼H$_2$O adduct)

White crystal m.p. 193° to 195° C. (decomposed)

Mass; m/z=468 (M$^+$)

NMR (δ, CDCl$_3$); 1.50 to 1.82 ( 4H, m), 2.00 to 2.38 (4H, m), 2.40 to 2.56 (1H, m), 2.64 to 2.80 ( 1H, m), 2.90 to 3.12 (3H, m), 3.54 (2H, s), 3.58 (3H, s), 4.72 to 4.77 (1H, m), 6.59 (1H, s), 6.87 (1H, d, J=15.6 Hz ), 7.04 ( 1H, dd, J=6.4 Hz, 15.6 Hz), 7.26 to 7.34 (5H, m), 7.79 (2H, d, J=8.8 Hz), 7.97 ( 2H, d, J=8.8 Hz), 8.75 (1H, s)

EXAMPLE 12

N-(7-methoxy-5,6-dihydro-7H-cyclopenta[d]pyrimidin-4-yl)-4-[3-(1-benzylpiperidin-4-yl)propanoyl]aniline (Compound II-168 in Table 1)

(as ¼H$_2$O adduct)

White crystal m.p. 178° to 180° C.

Mass; m/z=470 (M$^+$)

NMR (δ, CDCl$_3$); 1.19 to 1.45 (3H, m), 1.60 to 1.81 (4H, m), 1.88 to 2.01 (2H, m), 2.07 to 2.24 (1H, m), 2.39 to 2.60 (1H, m), 2.64 to 2.78 (1H, m), 2.85 to 3.02 (5H, m), 3.48 (2H, s), 3.58 (3H, s), 4.71 to 4.76 (1H, m), 6.52 (1H, s), 7.21 to 7.28 (5H, m), 7.76 (2H, d, J=8.8 Hz), 7.96 (2H, d, J=8.8 Hz)

EXAMPLE 13

(E)-N-(7-fluoro-5,6-dihydro-7H-cyclopenta[d]pyrimidin-yl)-4-[3-(1-benzylpiperidin-4-yl)propanoyl]aniline (Compound II-188 in Table 1)

Pale yellow powder

Mass ; m/z=456 (M$^+$)

NMR (δ, CDCl$_3$-DMSO-d$_6$); 1.47 to 1.90 (4H, m), 1.96 to 2.16 (2H, m), 1.86 to 2.16 (1H, m), 2.16 to 2.76 ( 3H, m), 2.76 to 3.23 (4H, m), 3.54 (2H, s), 5.70 to 5.78 and 5.96 to 6.06 (total 1H, each m), 6.89 (1H, d, J=15 to 16 Hz), 7.02 (1H, dd, J=15 to 16 Hz, J=5 to 6 Hz), 7.18 to 7.40 (5H, m), 7.86 to 8.04 (4H, m), 8.46 (1H, s), 8.74 (1H, s)

EXAMPLE 14

N-(7-fluoro-5,6-dihydro-7H-cyclopenta[d]pyrimidin-4-yl)-4-[3-(1-benzylpiperidin-4-yl)propanoyl]aniline·2HCl (2HCl salt of Compound II-183 in Table 1)

(as ½H$_2$O adduct)
White crystal
m.p. 173° to 175° C.
Mass; m/z=458 (M$^+$)
NMR (δ, CDCl$_3$-DMSO-d$_6$); 1.55 to 1.98 (7H, m), 2.16 to 2.80 (2H, m), 2.80 to 3.47 (8H, m), 4.30 (2H, d, J=4.9 Hz), 5.95 to 6.02 and 6.20 to 6.31 (total 1H, each m), 7.36 to 7.53 (3H, m), 7.59 to 7.76 (2H, m), 7.90 to 8.12 (4H, m), 8.88 (1H, s), 10.70 (1H, s), 10.88 (1H, br)

EXAMPLE 15

(E)-N-(5,6-dihydro-7H-cyclopenta[d]pyrimidin-4-yl)-4-{3-[1-(4-methoxybenzyl)piperidin-4-yl]propenoyl}aniline (Compound II-29 in Table 1)

(as ½H$_2$O adduct)
White powder
m.p. 198° to 199.5° C.
Mass; m/z=468 (M$^+$)
NMR (δ, CDCl$_3$-DMSO-d$_6$); 1.50 to 1.68 (2H, m), 1.76 to 1.82 (2H, m), 2.00 to 2.28 (5H, m), 2.88 to 3.04 (6H, m), 3.47 (2H, s), 3.80 (3H, s), 6.80 to 6.95 (3H, m), 7.01 (1H, dd, J=15.1 Hz, J=6.4 Hz), 7.23 (2H, d, J=8.3 Hz), 7.57 (1H, s), 7.84 (2H, d, J=8.8 Hz), 7.94 (2H, d, J=8.8 Hz), 8.61 (1H, s)

EXAMPLE 16

(E)-N-(5,6-diethylpyrimidin-4-yl)-4-[3-(1-benzylpiperidin-4-yl)propenoyl]aniline (Compound II-200 in Table 1)

Pale yellow powder
Mass (CI); m/z=455 (M++i)
NMR (δ, CDCl$_3$); 1.20 to 1.38 (6H, m), 1.46 to 1.88 (4H, m), 1.96 to 2.16 (2H, m), 2.15 to 2.40 (1H, m), 2.60 to 2.84 (4H, m), 2.88 to 3.02 (2H, m), 3.51 (2H, s), 6.71 (1H, s, br), 6.88 (1H, d, J=15 to 16 Hz), 7.04 (1H, dd, J=15 to 16 Hz, J=6 to 7 Hz), 7.20 to 7.45 (5H, m), 7.35 (2H, d, J=8 to 9 Hz), 7.97 (2H, d, J=8 to 9 Hz), 8.64 (1H, s)

EXAMPLE 17

(E)-N-(5,6-dihydro-7H-cyclopenta[d]pyrimidin-4-yl)-4-{3-[1-(4-fluorobenzyl)piperidin-4-yl]propenoyl}aniline (Compound II-11 in Table 1)

(as ½H$_2$O adduct)
White powder
m.p. 209° to 210.5° C.
Mass; m/z=456 (M$^+$)
NMR (δ, CDCl$_3$); 1.52 to 1.64 (2H, m), 1.80 to 1.84 (2H, m), 2.05 to 2.10 (2H, m), 2.13 to 2.22 (2H, m), 2.23 to 2.31 (1H, m), 2.90 to 3.02 (6H, m), 3.49 (2H, s), 6.90 (1H, d, J=15.1 Hz), 6.92 to 7.03 (3H, m), 7.28 to 7.30 (2H, m), 7.85 (1H, s), 7.88 (2H, d, J=8.8 Hz), 7.94 (2H, d, J=8.8 Hz), 8.60 (1H, s)

EXAMPLE 18

N-(5,6-dihydro-7H-cyclopenta[d]pyrimidin-4-yl)-4-{3-[1-(4-fluorobenzyl)piperidin-4-yl]propanoyl}aniline (Compound II-8 in Table 1)

(as ½H$_2$O adduct)
Pale yellow powder
m.p. 179° to 181° C.
Mass; m/z=458 (M$^+$)
NMR (δ, CDCl$_3$); 1.29 to 1.45 (3H, m), 1.66 to 1.80 (4H, m), 1.94 to 2.10 (2H, m), 2.15 to 2.26 (2H, m), 2.82 to 3.05 (8H, m), 3.56 (2H, s, br), 6.46 (1H, s), 6.96 to 7.05 (2H, m), 7.25 to 7.36 (2H, m), 7.78 (2H, d, J=8.8 Hz), 7.96 (2H, d, J=8.8 Hz), 8.66 (1H, s)

EXAMPLE 19

(E)-N-(5,6-dihydro-7H-cyclopenta[d]pyrimidin-4-yl)-4-{3-[1-(3-fluorobenzyl)piperidin-4-yl]propenoyl}aniline (Compound II-17 in Table 1)

White powder
m.p. 210° to 211° C.
Mass (CI); m/z=457 (M$^+$+1)
NMR (δ, CDCl$_3$); 1.51 to 1.85 (4H, m), 2.02 to 2.30 (5H, m), 2.83 to 3.06 (6H, m), 3.52 (2H, s), 6.46 (1H, s), 6.89 (1H, d, J=15.6 Hz), 6.95 to 7.12 (4H, m), 7.23 to 7.35 (1H, m), 7.78 (2H, d, J=8.8 Hz), 7.98 (2H, d, J=8.8 Hz), 8.66 (1H, s)

EXAMPLE 20

N-(5,6-dihydro-7H-cyclopenta[d]pyrimidin-4-yl)-4-(3-[1-(3-fluorobenzyl)piperidin-4-yl]propanoyl)aniline·2HCl (2HCl salt of Compound II-14 in Table 1)

(as ³⁄₂H$_2$O adduct)
White powder
m.p.>252° C. (decomposed)
Mass (CI); 459 (M$^+$+1)
NMR (δ, CDCl$_3$); 1.24 to 1.40 (3H, m), 1.54 to 1.77 (4H, m), 1.89 to 2.02 (2H, m), 2.15 to 2.25 (2H, m), 2.82 to 2.91 (4H, m), 2.91 to 3.05 (4H, m), 3.47 (2H, s), 6.45 (1H, s), 6.89 to 6.96 (1H, m), 7.02 to 7.11 (2H, m), 7.22 to 7.28 (1H, m), 7.76 (2H, d, J=8.8 Hz), 7.97 (2H, d, J=8.8 Hz), 8.65 (1H, s)

EXAMPLE 21

4-[1-Oxo-2-(1-benzylpiperidin-4-yl)methyleneindan-5-yl]amino-5,6-dihydro-7H-cyclopenta[d]pyrimidine (Compound III-3 in Table 2)

Under ice cooling, 1.70 g of a 28% sodium methoxide·methanol solution was added to 1.96 g of 4-(1-oxoindan-5-yl)amino-5,6-dihydro-7H-cyclopenta[d]pyrimidine dissolved in tetrahydrofuran, and then 1.80 g of 1-benzyl-4-formylpiperidine was added dropwise thereto. After the mixture was stirred for 1.5 hours, a saturated saline solution was added to the reaction mixture, and the mixture was extracted with chloroform. The extract was dried over anhydrous sodium sulfate and condensed under reduced pressure. The obtained residue was applied to silica gel column chromatography and then recrystallized from chlo roform to obtain 1.35 g of the title compound as pale yellow crystal.

(as ½H$_2$O adduct)

m.p.>260° C. (decomposed)

Mass; m/z=450 (M$^+$)

NMR (δ, CDCl$_3$); 1.45 to 1.85 (4H, m), 1.96 to 2.46 (5H, m), 2.80 to 3.10 (6H, m), 3.56 (2H, s), 3.70 (2H, s), 6.55 (1H, s), 6.70 (1H, d, J=9.8 Hz), 7.24 to 7.41 (6H, m), 7.82 (1H, d, J=5.3 Hz), 8.18 (1H, s), 8.66 (1H, s)

EXAMPLE 22

4-[1-Oxo-2-(1-benzylpiperidin-4-yl)methylindan-5-yl]amino-5,6-dihydro-7H-cyclopenta[d]pyrimidine (Compound III-4 in Table 2)

0.53 g of platinum oxide was added to 1.35 g of 4-[1-oxo-2-(1-benzylpiperidin-4-yl)methyleneindan-5-yl]amino-5,6-dihydro-7H-cyclopenta[d]pyrimidine dissolved in a mixed solution of 60 ml of tetrahydrofuran, 60 ml of ethanol and 1 ml of acetic acid, and the mixture was stirred under a hydrogen stream at room temperature for 8 hours. After the catalyst was removed by filtration, the filtrate was condensed. The obtained residue was applied to silica gel column chromatography to obtain 1.31 g of the title compound as pale yellow powder.

m.p. 200° to 202° C.

Mass; m/z=452 (M$^+$)

NMR (δ, CDCl$_3$); 1.18 to 2.12 (9H, m), 2.12 to 2.30 (2H, m), 2.62 to 3.08 (8H, m), 3.25 to 3.44 (1H, m), 3.55 (2H, s), 6.49 (1H, s), 7.20 to 7.41 (6H, m), 7.71 (1H, d, J=8.3 Hz), 8.10 (1H, d, J=1 to 2 Hz), 8.66 (1H, s)

EXAMPLE 23

N-(5-ethylpyrimidin-4-yl)-4-[3-(1-benzylpiperidin-4-yl)propanoyl]aniline (Compound II-205 in Table 1)

To 10 ml of ethanol were added 0.23 g of 4-[3-(1-benzylpiperidin-4-yl)propanoyl]aniline and 0.13 g of 4-chloro-5-ethylpyrimidine, and after adding 2 ml of an ethanol solution of hydrochloric acid (containing 0.071 g of hydrochloric acid), the mixture was reacted under reflux for 2 hours. After cooling, a 28% sodium methylate-methanol solution was added to the reaction mixture to make it alkaline, and then the mixture was condensed under reduced pressure. The obtained residue was applied to silica gel column chromatography to obtain 0.18 g of the title compound as pale yellow crystal.

m.p. 136.5° to 138° C.

Mass (CI); m/z=429 (M$^+$+1)

NMR (δ, CDCl$_3$); 1.24 to 1.43 (3H, m), 1.37 (3H, t, J=7.3 Hz), 1.56 to 1.80 (4H, m), 1.87 to 2.05 (2H, m), 2.61 (2H, q, J=7.3 Hz), 2.81 to 3.00 (4H, m), 3.51 (2H, s), 6.63 (1H, s, br), 7.18 to 7.37 (5H, m), 7.77 (2H, d, J=9.2 Hz), 7.98 (2H, d, J=9.2 Hz), 8.27 (1H, s), 8.71 (1H, s)

EXAMPLE 24

N-(5,6-dihydro-7H-cyclopenta[d]pyrimidin-4-yl)-4-{3-[1-(2-nitrobenzyl)piperidin-4-yl]propanoyl}aniline (Compound II-242 in Table 1)

(1) N-(5,6-dihydro-7H-cyclopenta[d]pyrimidin-4-yl)-4-[3(1-acetylpiperidin-4-yl)propanoyl]aniline To 80 ml of chloroform were added 4.53 g of 4-[3-(1-acetylpiperidin-4-yl)propanoyl]aniline and 3.83 g of 4-chloro-5,6-dihydro-7H-cyclopenta[d]pyrimidine, and after adding 10 ml of a chloroform solution of hydrochloric acid (containing 0.9 g of hydrochloric acid), the mixture was refluxed under heating for 5 hours. After completion of the reaction, a 28% sodium methoxide was added to the mixture under ice cooling to make it alkaline and then the solvent was removed by distillation under reduced pressure. The obtained residue was applied to silica gel column chromatography to obtain 6.16 g of the title compound as brown powder.

Mass; m/z=392 (M$^+$)

NMR (δ, CDCl$_3$-DMSO-d$_6$); 1.00 to 1.27 (2H, m), 1.52 to 1.87 (5H, m), 2.05 (3H, s), 2.03 to 2.23 (2H, m), 2.45 to 2.61 (2H, m), 2.87 to 3.11 (6H, m), 3.76 to 3.89 (1H, m), 4.46 to 4.58 (1H, m), 7.86 to 7.96 (4H, m), 8.51 (1H, s), 8.70 (1H, s)

(2) N-(5,6-dihydro-7H-cyclopenta[d]pyrimidin-4-yl)-4-[3-(piperidin-4-yl)propanoyl]aniline·2HCl salt 30 ml of conc. hydrochloric acid was added to 6.16 g of N-(5,6-dihydro-7H-cyclopenta[d]pyrimidin-4-yl)-4-[3-(1-acetylpiperidin-4-yl)propanoyl]aniline, and after refluxing under heating for 7 hours, the mixture was condensed under reduced pressure. The obtained residue was washed with methanol to obtain 3.38 g of the title compound as yellow powder.

Mass; m/z=350 (M$^+$)

NMR (δ, CD$_3$OD); 1.36 to 1.56 (2H, m), 1.64 to 1.83 (3H, m), 1.95 to 2.09 (2H, m), 2.92 to 3.24 (8H, m), 3.35 to 3.46 (2H, m), 7.08 to 7.25 (1H, m), 7.90 (2H, d, J=9.2 Hz), 8.08 (2H, d, J=9.2 Hz), 8.75 (1H, s) (3) N-(5,6-dihydro-7H-cyclopenta[d]pyrimidin-4-yl)-{3-[1(2-nitrobenzyl)piperidin-4-yl]acetyl}aniline 30 ml of acetone, 7.12 g of potassium carbonate and 0.62 g of 2-nitrobenzyl bromide were added to 1.00 g of N-(5, 6-dihydro-7H-cyclopenta[d]pyrimidin-4-yl)-4-[3-(piperidin-4-yl)propanoyl]aniline·2HCl salt, and the mixture was stirred at room temperature for 2 hours and allowed to stand overnight. Then, after separating the solid by filtration and removing the solvent by distillation under reduced pressure, the obtained residue was applied to silica gel column chromatography to obtain 0.72 g of the title compound as white powder.

m.p. 164° to 166° C.

Mass (SIMS); m/z=486 (M$^+$+1)

NMR (δ, CDCl$_3$); 1.16 to 1.40 (3H, m), 1.52 to 1.77 (4H, m), 1.94 to 2.08 (2H, m), 2.09 to 2.27 (2H, m), 2.72 to 3.06 (8H, m), 3.75 (2H, s), 6.47 (1H, s), 7.32 to 7.43 (1H, m), 7.48 to 7.59 (1H, m), 7.60 to 7.68 (1H, m), 7.76 (2H, d, J=8.5 Hz), 7.74 to 7.83 (1H, m), 7.96 (2H, d, J=9.2 Hz), 8.65 (1H, s)

EXAMPLE 25

N-(5-methylpyrimidin-4-yl)-4-[(1-benzylpiperidin-4-yl)acetyl]aniline (Compound II-220 in Table 1)

To 70 ml of chloroform were added 7.00 g of 4-[(1-benzylpiperidin-4-yl)acetyl]aniline·2HCl salt and 8.38 g of 4-chloro-5-methylpyrimidine, and after further adding 10 ml of an ethanol solution of hydrochloric acid (containing 1.7 g of hydrochloric acid), the mixture was reacted under reflux for 5 hours. After the reaction, a 28% sodium methylate-methanol solution was added to the reaction mixture to make it alkaline and then the mixture was condensed under reduced pressure. The obtained residue was applied to silica gel column chromatography to obtain 5.30 g of the title compound as pale yellow crystal.

m.p. 211° to 213° C.

Mass; m/z=400 (M$^+$)

NMR (δ, CDCl$_3$); 1.26 to 1.47 (2H, m), 1.63 to 1.80 (3H, m), 1.89 to 2.08 (2H, m), 2.25 (3H, s), 2.76 to 2.93 (4H, m), 3.48 (2H, s), 6.58 (1H, s, br), 7.17 to 7.38 (5H, m), 7.78 (2H, d, J=8.6 Hz), 7.97 (2H, d, J=8.6 Hz), 8.24 (1H, s), 8.70 (1H, s)

EXAMPLE 26

N-(5,6-dihydro-7H-cyclopenta[d]pyrimidin-4-yl)-4-[(1-benzylpiperidin-4-yl)acetyl]aniline (Compound II-1 in Table 1)

(1) N-(5,6-dihydro-7H-cyclopenta[d]pyrimidin-4-yl)-4-[(1-acetylpiperidin-4-yl)acetyl]aniline To 50 ml of chloroform were added 6.63 g of 4-[(1-acetylpiperidin-4-yl)acetyl]aniline·trifluoroacetate and 3.01 g of 4-chloro-5,6-dihydro-7H-cyclopenta[d]pyrimidine, and after adding 10 ml of a chloroform solution of hydrochloric acid (containing 0.6 g of hydrochloric acid), the mixture was reacted under reflux for 3 hours. After the reaction, a 28% sodium methylate-methanol solution was added to the reaction mixture under cooling to make it alkaline. After removing solid material, the filtrate was condensed under reduced pressure and the obtained residue was applied to silica gel column chromatography to obtain 6.08 g of the title compound as yellowish white powder.

m.p. 225° to 227° C.

Mass (CI); m/z=379 (M$^+$+1)

NMR (δ, CDCl$_3$); 1.12 to 1.33 (2H, m), 1.72 to 1.92 (2H, m), 2.04 to 2.35 (3H, m), 2.09 (3H, s), 2.52 to 2.68 (1H, m), 2.68 to 2.93 (4H, m), 2.93 to 3.18 (3H, m), 3.94 to 4.12 (1H, m), 4.55 to 4.70 (1H, m), 6.65 (1H, s, br), 7.79 (2H, d, J=8.8 Hz), 7.89 (2H, d, J=8.8 Hz), 8.65 (1H, s) (2) N-(5,6-dihydro-7H-cyclopenta[d]pyrimidin-4-yl)-4-[(piperidin-4-yl)acetyl]aniline·2HCl salt 50 ml of conc. hydrochloric acid was added to 6.08 g of N-(5,6-dihydro-7H-cyclopenta[d]pyrimidin-4-yl)-4-[(1-acetylpiperidin-4-yl)acetyl]aniline, and after refluxing the mixture under heating, the solvent was removed by distillation under reduced pressure. The obtained solid was washed with hot-ethanol to obtain 5.13 g of the title compound as yellowish white powder.

Mass (CI); m/z=337 (M$^+$+1)

NMR (δ, CDCl$_3$-DMSO-d$_6$); 1.48 to 1.69 (2H, m), 1.84 to 2.00 (2H, m), 2.10 to 2.35 (3H, m), 2.72 to 3.21 (8H, m), 3.21 to 3.38 (2H, m), 7.92 (2H, d, J=9.2 Hz), 7.99 (2H, d, J=8.6 Hz), 8.84 (1H, s), 10.64 (1H, s)

(3) N-(5,6-dihydro-7H-cyclopenta[d]pyrimidin-4-yl)-4-[(1-benzylpiperidin-4-yl)acetyl]aniline 50 ml of acetone, 1.14 g of potassium carbonate and 0.4 ml of benzyl bromide were added to 1.34 g of N-(5,6-dihydro-7H-cyclopenta[d]pyrimidin-4-yl)-4-[(piperidin-4-yl)acetyl]aniline, and the mixture was stirred at room temperature for 4 hours. After separating the solid by filtration and removing the solvent by distillation under reduced pressure, the obtained residue was applied to silica gel column chromatography to obtain 1.05 g of the title compound as yellowish white powder.

m.p. 212° to 214° C. (decomposed)

Mass; m/z=426 (M$^+$)

NMR (δ, CDCl$_3$); 1.28 to 1.48 (2H, m), 1.67 to 1.80 (2H, m), 1.90 to 2.09 (3H, m), 2.12 to 2.28 (2H, m), 2.79 to 2.90 (6H, m), 2.98 to 3.05 (2H, m), 3.49 (2H, s), 6.42 (1H, s), 7.20 to 7.38 (5H, m), 7.77 (2H, d, J=8.8 Hz), 7.96 (2H, d, J=8.8 Hz), 8.66 (1H, s)

EXAMPLE 27

N-(5-methylpyrimidin-4-yl)-4-{[1-(2-pyridylmethyl)piperidin-4-yl]acetyl}aniline (Compound II-219 in Table 1)

In the same manner as in Example 26-(1), (2) and (3) except for using 4-chloro-5-methylpyrimidine in place of 4-chloro-5,6-dihydro-7H-cyclopenta[d]pyrimidine and using 2-chloromethylpyridine in place of benzyl bromide in Example 26-(1), (2) and (3), the following compounds were obtained, respectively.

(1) N-(5-methylpyrimidin-4-yl)-4-[(1-acetylpiperidin-4yl)acetyl]aniline

Yellowish white solid

Mass (CI); m/z=353 (M$^+$+1)

NMR (δ, CDCl$_3$); 1.12 to 1.30 (2H, m), 1.73 to 1.93 (3H, m), 2.08 (3H, s), 2.26 (3H, s), 2.52 to 2.67 (1H, m), 2.84 to 2.93 (2H, m), 3.02 to 3.17 (1H, m), 3.73 to 3.86 (1H, m), 4.54 to 4.67 (1H, m), 6.92 (1H, s), 7.82 (2H, d, J=8.6 Hz), 7.97 (2H, d, J=9.2 Hz), 8.24 (1H, s), 8.69 (1H, s)

(2) N-(5-methylpyrimidin-4-yl)-4-[(piperidin-4-yl)acetyl]aniline

Yellowish white solid

Mass (CI); m/z=311 (M$^+$+1)

NMR (δ, CDCl$_3$); 1.46 to 1.70 (2H, m), 1.82 to 1.98 (3H, m), 2.42 (3H, s), 2.83 to 3.09 (2H, m), 3.02 (2H, d, J=6.7 Hz), 3.21 to 3.38 (2H, m), 7.85 (2H, d, J=8.5 Hz), 8.02 (2H, d, J=8.5 Hz), 8.43 (1H, s), 8.86 (1H, s), 10.36 (1H, s)

(3) N-(5-methylpyrimidin-4-yl)-4-{[1-(2-pyridylmethyl)piperidin-4-yl]acetyl}aniline White crystal m.p. 207° to 209° C.

Mass (CI); m/z=402 (M$^+$+1)

NMR (δ, CDCl$_3$); 1.33 to 1.50 (2H, m), 1.66 to 1.81 (2H, m), 1.81 to 1.94 (1H, m), 2.07 to 2.20 (2H, m), 2.52 (3H, s), 2.86 (2H, d, J=6.7 Hz), 2.78 to 2.95 (2H, m), 3.64 (2H, s), 6.63 (1H, s), 7.11 to 7.20 (1H, m), 7.40 (1H, d, J=7.3 Hz), 7.61 to 7.70 (1H, m), 7.79 (2H, d, J=8.5 Hz), 7.98 (2H, d, J=9.2 Hz), 8.25 (1H, s), 8.55 (1H, d, J=4.8 Hz), 8.70 (1H, s)

EXAMPLE 28

(E)-N-(5,6-dihydro-7H-cyclopenta[d]pyrimidin-4-yl)-4-[4-(1-benzylpiperidin-4-yl)-2-butenoyl]aniline (Compound II-6 in Table 1)

30 ml of ethanol and 0.58 g of 4-chloro-5,6-dihydro-7H-cyclopenta[d]pyrimidine were added to 1.21 g of 4-[4-(1-benzylpiperidin-4-yl)-3-hydroxybutanoyl] aniline·trifluoroacetate, 1 ml of an ethanol solution of hydrochloric acid (containing 0.29 g of hydrochloric acid) was added thereto and the mixture was stirred under heating at 60° C. for 40 minutes. Then, a saturated sodium hydrogen carbonate aqueous solution was added thereto and the mixture was extracted with chloroform. After drying over anhydrous sodium sulfate, the solvent was removed by distillation under reduced pressure and the obtained residue was applied to silica gel column chromatography to obtain 0.40 g of the title compound as yellow powder.

m.p. 184° to 185° C.

Mass (CI); m/z=453 (M$^+$+1)

NMR (δ, CDCl$_3$); 1.24 to 1.60 (3H, m), 1.60 to 1.82 (2H, m), 1.88 to 2.05 (2H, m), 2.10 to 2.34 (4H, m), 2.80 to 2.98 (4H, m), 2.98 to 3.08 (2H, m), 3.50 (2H, s), 6.48 (1H, s, br), 6.90 (1H, d, J=16.9 Hz), 6.98 to 7.12 (1H, m), 7.12 to 7.41 (5H, m), 7.78 (2H, d, J=8.8 Hz), 7.97 (2H, d, J=8.8 Hz), 8.66 (1H, s)

EXAMPLE 29

N-(5,6-dihydro-7H-cyclopenta[d]pyrimidin-4-yl)-4-[4-(1-benzylpiperidin-4-yl)butanoyl]aniline (Compound II-3 in Table 1)

30 ml of ethanol and 0.1 g of platinum oxide were added to 0.24 g of (E)-N-(5,6-dihydro-7H-cyclopenta[d]pyrimidin-4-yl)-4-[4-(1-benzylpiperidin-4-yl)-2-butenoyl]aniline, and the mixture was stirred at room temperature under a hydrogen stream for 45 minutes. After removing the solid by filtration, the solvent was removed by distillation and the obtained residue was applied to silica gel column chromatography to obtain 0.19 g of the title compound as white powder.

m.p. 170° to 173° C.

Mass (CI); m/z=455 (M$^+$+1)

NMR (δ, CDCl$_3$); 1.14 to 1.38 (5H, m), 1.56 to 1.83 (6H, m), 1.83 to 2.01 (2H, m), 2.14 to 2.27 (2H, m), 2.85 to 2.96 (4H, m), 2.96 to 3.06 (2H, m), 3.49 (2H, s), 6.42 (1H, s, br), 7.19 to 7.35 (5H, m), 7.76 (2H, d, J=8.8 Hz), 7.97 (2H, d, J=8.8 Hz), 8.65 (1H, s)

EXAMPLE 30

(a) N-(5,6-dihydro-7H-cyclopenta[d]pyrimidin-4-yl)-4 [(1-benzyl-4-hydroxypiperidin-4-yl)acetyl]aniline (Compound II-216 in Table 1), (b) N-(5,6-dihydro-7H-cyclopenta[d]pyrimidin-4-yl)-4 [(1-benzyl-4-ethoxypiperidin-4-yl)acetyl]aniline (Compound II-215 in Table 1) and (c) N-(5,6-dihydro-7H-cyclopenta[d]pyrimidin-4-yl)-4 [(1-benzyl-1,2,5,6-tetrahydropyridin-4-yl)acetyl]aniline (Compound II-217 in Table 1)

30 ml of ethanol and 0.59 g of 4-chloro-5,6-dihydro-7H-cyclopenta[d]pyrimidine were added to 1.04 g of 4-[(1-benzyl-4-hydroxypiperidin-4-yl)acetyl] aniline·trifluoroacetate, then 1 ml of an ethanol solution of hydrochloric acid (containing 0.29 g of hydrochloric acid) was added to the mixture and the mixture was stirred at 60° C. for 45 minutes. Thereafter, 1 ml of triethylamine and water were added thereto, and the reaction mixture was extracted with chloroform and dried over anhydrous sodium sulfate. After removing the solvent by distillation under reduced pressure, the obtained residue was applied to silica gel column chromatography to obtain 0.60 g, 0.23 g and 0.05 g of the title compounds (a), (b) and (c), respectively.

Compound of (a)

Yellowish white crystal m.p. 193° to 195° C.

Mass (CI); m/z=443 (M$^+$+1)

NMR (δ, CDCl$_3$); 1.62 to 1.88 (4H, m), 2.12 to 2.30 (2H, m), 2.42 to 2.58 (2H, m), 2.58 to 2.72 (2H, m), 2.86 (2H, t, J=7.3 Hz), 2.93 to 3.06 (2H, m), 3.08 (2H, s), 3.56 (2H, s), 4.14 (2H, s), 6.49 (1H, s, br), 7.21 to 7.38 (5H, m), 7.79 (2H, d, J=8.6 Hz), 7.95 (2H, d, J=8.6 Hz), 8.66 (1H, s)

Compound of (b)

Yellowish white crystal m.p. 142° to 143° C.

Mass (CI); m/z=471 (M$^+$+1)

NMR (δ, CDCl$_3$); 1.13 (3H, t, J=7.7 Hz), 1.74 to 1.95 (4H, m), 2.13 to 2.28 (2H, m), 2.28 to 2.44 (2H, m), 2.54 to 2.70 (2H, m), 2.85 (2H, t, J=7.3 Hz), 3.01 (2H, t, J=7.9 Hz), 3.10 (2H, s), 3.40 to 3.48 (2H, m), 3.51 (2H, s, br), 6.43 (1H, s), 7.18 to 7.38 (5H, m), 7.76 (2H, d, J=8.5 Hz), 7.96 (2H, d, J=9.2 Hz), 8.65 (1H, s)

Compound of (c)

Pale yellow crystal m.p. 165° to 167° C.

Mass; 424 (M$^+$)

NMR (δ, CDCl$_3$); 2.12 to 2.28 (4H, m), 2.53 to 2.66 (2H, m), 2.78 to 2.91 (2H, m), 2.91 to 3.08 (4H, m), 3.60 (2H, s), 3.61 (2H, s), 5.54 (1H, s, br), 6.47 (1H, s), 7.20 to 7.59 (5H, m), 7.77 (2H, d, J=8.5 Hz), 7.99 (2H, d, J=8.5 Hz), 8.65 (1H, s)

EXAMPLE 31

N-(5,6-dihydro-7H-cyclopenta[d]pyrimidin-4-yl)-4-[(1-benzyl-4-piperidinyliden)acetyl]aniline (Compound II-4 in Table 1)

To a mixed solvent of 40 ml of chloroform and 20 ml of ethanol were added 2.33 g of 4-[(1-benzyl-4-piperidinyliden)acetyl]aniline and 1.63 g of 4-chloro-5,6-dihydro-7H-cyclopenta[d]pyrimidine, and further 6 ml of an ethanol solution of hydrochloric acid (containing 0.4 g of hydrochloric acid) was added to the mixture and the mixture was stirred at 50° to 60° C. for 3.5 hours under heating. Then, under ice cooling, a 28% sodium methylate-methanol solution was added to the mixture to make it alkaline, and then the solvent was removed by distillation under reduced pressure and the obtained residue was applied to silica gel column chromatography to obtain 0.3 g of the title compound as yellowish white powder.

Mass (CI); m/z=425 (M$^+$+1)

NMR (δ, CDCl$_3$); 2.13 to 2.24 (2H, m), 2.40 to 2.51 (2H, m), 2.51 to 2.65 (4H, m), 2.75 to 2.90 (2H, m), 2.90 to 3.06 (4H, m), 3.54 (2H, s), 6.50 (1H, s), 6.64 (1H, s), 7.18 to 7.43 (5H, m), 7.61 (2H, d, J=9.2 Hz), 7.95 (2H, d, J=8.5 Hz), 8.65 (1H, s)

EXAMPLE 32

N-(5,6-dihydro-7H-cyclopenta[d]pyrimidin-4-yl)-4-{3-[1-(2-thienylmethyl)piperidin-4-yl] propanoyl}aniline·2HCl (2HCl salt of Compound II-104 in Table 1)

30 ml of 1,2-dichloroethane and 0.07 ml of triethylsilane were added to 0.20 g of N-(5,6-dihydro-7H-cyclopenta[d] pyrimidin-4-yl)-4-{3-[1-(2-thienylmethyl)piperidin-4-yl] propenoyl}aniline, then 0.35 ml of trifluoroacetic acid was added to the mixture and the mixture was stirred at 50° C. for 3 hours under heating. After the reaction, the solvent was removed by distillation under reduced pressure, a 1N sodium hydroxide aqueous solution was added to the residue and the residue was extracted with chloroform. After drying over anhydrous sodium sulfate, the solvent was removed by distillation under reduced pressure and the obtained residue was applied to silica gel column chromatography to obtain an ocherous solid. The solid was recrystallized form isopropyl alcohol and further treated with hydrochloric acid to obtain 0.05 g of the title compound as white powder.

(as ¾H$_2$O adduct)

m.p. 187° C. (decomposed)

Mass (CI); m/z=447 (M$^+$+1)

NMR (δ, CDCl$_3$); 1.14 to 1.46 (2H, m), 1.46 to 1.84 (5H, m), 1.88 to 2.12 (2H, m), 2.12 to 2.20 (2H, m), 2.74 to 3.10 (8H, m), 3.70 to 3.85 (2H, m), 6.40 (1H, s), 6.87 to 7.02 (2H, m), 7.16 to 7.20 (6H, m), 7.76 (2H, d, J=9.2 Hz), 7.97 (2H, d, J=8.5 Hz), 8.65 (1H, s)

EXAMPLE 33

N-(7-hydroxy-5,6-dihydro-7H-cyclopenta[d]pyrimidin-4-yl)-4-[3-(1-benzylpiperidin-4-yl)propanoyl]aniline (Compound II-167 in Table 1)

To 15 ml of ethanol were added 0.60 g of 4-[3-(1-benzylpiperidin-4-yl)propanoyl]aniline and 0.51 g of 7-acetoxy-4-chloro-5,6-dihydro-7H-cyclopenta[d]pyrimidine, then 3 ml of an ethanol solution of hydrochloric acid (containing 0.19 g of hydrochloric acid) was added to the mixture and the mixture was reacted under reflux for 30 minutes. After cooling, a 28% sodium methylate-methanol solution was added to the reaction mixture to make it alkaline, and the mixture was condensed under reduced pressure. The obtained residue was applied to silica gel column chromatography to obtain 0.49 g of the title compound as white crystal.

m.p. 189° to 190° C.

Mass; m/z=456 (M$^+$)

NMR (δ, CDCl$_3$-DMSO-d$_6$); 1.21 to 1.45 (3H, m), 1.56 to 1.81 (4H, m), 1.86 to 2.11 (3H, m), 2.47 to 3.08 (7H, m), 3.50 (2H, s), 4.83 (1H, br), 5.05 to 5.17 (1H, m), 7.16 to 7.38 (5H, m), 7.87 (2H, d, J=8.8 Hz), 7.94 (2H, d, J=8.8 Hz), 8.16 (1H, s), 8.68 (1H, s)

EXAMPLE 34

N-(7-hydroxy-5,6-dihydro-7H-cyclopenta[d]pyrimidin-4-yl)-4-[(1-benzylpiperidin-4-yl)acetyl]aniline (Compound II-236 in Table 1)

In the same manner as in Example 33 except for using 4-[1-benzylpiperidin-4-yl)acetyl]aniline in place of 4-[3(1-benzylpiperidin-4-yl)propanoyl]aniline, the reaction was carried out to obtain the tile compound as white crystal.

m.p. 174° to 176° C.

Mass; m/z=442 (M$^+$)

NMR (δ, CDCl$_3$-DMSO-d$_6$); 1.18 to 1.48 (3H, m), 1.66 to 1.80 (2H, m), 1.88 to 2.13 (4H, m), 2.50 to 2.66 (1H, m), 2.66 to 3.05 (3H, m), 2.85 (2H, d, J=6.7 Hz), 3.49 (2H, s), 5.09 to 5.20 (1H, m), 7.18 to 7.43 (6H, m), 7.85 (2H, d, J=9.2 Hz), 7.95 (2H, d, J=9.2 Hz), 8.69 (1H, s)

EXAMPLE 35

N-(7-acetoxy-5,6-dihydro-7H-cyclopenta[d]pyrimidin-4-yl)-4-[(1-benzylpiperidin-4-yl)acetyl]aniline (Compound II-237 in Table 1)

20 ml of chloroform and 0.65 ml of acetic anhydride were added to 0.35 g of N-(7-hydroxy-5,6-dihydro-7H-cyclopenta[d]pyrimidin-4-yl)-4-[(1-benzylpiperidin-4-yl)acetyl] aniline, and the mixture was refluxed under heating for 4 hours. Then, the solvent was removed by distillation under reduced pressure and the obtained residue was applied to silica gel column chromatography to obtain 0.16 g of the title compound as white crystal.

(as ½H$_2$O adduct)

m.p. 210° to 212° C.

Mass; m/z=484 (M$^+$)

NMR (δ, CDCl$_3$); 1.29 to 1.47 (3H, m), 1.54 to 1.63 (2H, m), 1.68 to 1.94 (4H, m), 2.15 (3H, s), 2.67 to 3.04 (4H, m), 2.86 (2H, d, J=6.7 Hz), 3.50 (2H, s, br), 6.07 to 6.14 (1H, m), 6.53 (1H, s), 7.19 to 7.34 (5H, m), 7.78 (2H, d, J=9.2 Hz), 7.98 (2H, d, J=8.6 Hz), 8.78 (1H, s)

EXAMPLE 36

N-(5,6-dihydro-7H-cyclopenta[d]pyrimidin-4-yl)-4-{3-[1-(2-aminobenzyl)piperidin-4-yl]propanoyl}aniline (Compound II-272 in Table 1)

To 0.59 g of N- (5,6-dihydro-7H-cyclopenta[d]pyrimidin-4-yl)-4-3-[1-(2-nitrobenzyl)piperidin-4-yl]propanoyl)aniline were added 20 ml of ethanol, 40 ml of methanol, 5 ml of acetic acid and 0.05 g of platinum oxide, and the mixture was stirred at room temperature under a hydrogen stream for 4 hours. Then, after the solid was removed by filtration and the solvent was removed by distillation under reduced pressure, a saturated sodium hydrogen carbonate aqueous solution was added to the residue and the mixture was extracted with chloroform. The solvent was removed by distillation under reduced pressure and the obtained solid was recrystallized from ethanol to obtain 0.32 g of the title compound as pale brown crystal.

Mass; m/z=455 (M$^+$)

NMR (δ, CDCl$_3$); 1.12 to 1.32 (3H, m), 1.56 to 1.77 (4H, m), 1.83 to 1.98 (2H, m), 2.14 to 2.28 (2H, m), 2.79 to 3.07 (8H, m), 3.47 (2H, s), 4.81 (1H, s, br), 6.43 (1H, s, br), 6.62 to 6.68 (2H, m), 6.97 (1H, d, J=6.7 Hz), 7.05 to 7.11 (1H, m), 7.76 (2H, d, J=8.5 Hz), 7.97 (2H, d, J=9.2 Hz), 8.65 (1H, s)

EXAMPLE 37

N- (5,6-dihydro-7H-cyclopenta[d]pyrimidin-4-yl)-4-{3-[1-(2-acetylaminobenzyl)piperidin-4-yl]propanoyl}aniline (Compound II-249 in Table 1)

To 0.17 g of N-(5,6-dihydro-7H-cyclopenta[d]pyrimidin-4-yl)-4-(3-[1-(2-aminobenzyl)piperidin-4-yl]propanoyl)aniline were added 30 ml of chloroform, 1 ml of acetic anhydride and 0.38 g of 4-dimethylaminopyridine, and the mixture was stirred at 50° C. for 10 minutes. Then, the solvent was removed by distillation under reduced pressure and the obtained residue was applied to silica gel column chromatography to obtain 0.06 g of the title compound as white crystal.

m.p. 219° to 221.5° C.

Mass; m/z=497 (M$^+$)

NMR (δ, CDCl$_3$); 1.14 to 1.34 (2H, m), 1.34 to 1.50 (1H, m), 1.66 to 1.89 (4H, m), 1.96 to 2.10 (2H, m), 2.14 (3H, s), 2.11 to 2.28 (2H, m), 2.80 to 3.08 (8H, m), 3.57 (2H, s), 6.44 (1H, s), 6.94 to 7.01 (1H, m), 7.25 (2H, d, J=6.1 Hz), 7.23 to 7.31 (1H, m), 7.78 (2H, d, J=8.5 Hz), 7.97 (2H, d, J=9.2 Hz), 8.27 (1H, d, J=8.6 Hz), 8.65 (1H, s), 11.04 (1H, s)

EXAMPLE 38

N-acetyl-N-(5,6-dihydro-7H-cyclopenta[d]pyrimidin-4yl)-4-[3-(1-benzylpiperidin-4-yl)propanoyl]aniline·2HCl (2HCl salt of Compound II-221 in Table 1)

To 10 ml of a chloroform solution containing 0.72 g of N-(5,6-dihydro-7H-cyclopenta[d]pyrimidin-4 -yl)-4-[3-(1-benzylpiperidin-4-yl)propanoyl]aniline were added under ice cooling 0.66 g of triethylamine and 0.46 ml of acetyl chloride. After stirring under ice cooling for one hour, a saturated saline solution was added to the mixture and the mixture was extracted with chloroform. The chloroform layer was dried over anhydrous sodium sulfate and condensed under reduced pressure. The obtained residue was applied to silica gel column chromatography to obtain the free material of the title compound. This material was dissolved in ethyl acetate and treated with a hydrogen chloride gas to obtain 0.54 g of the title compound as pale brown crystal.

(as $H_2O$ adduct)

m.p. 128° to 131.5° C.

Mass (CI); m/z=483 ($M^+$+1)

NMR (δ, $CDCl_3$); 1.52 to 1.96 (5H, m), 2.00 to 2.38 (4H, m), 2.23 (3H, s), 2.53 to 2.86 (4H, m), 2.93 to 3.12 (2H, m), 3.34 to 3.57 (4H, m), 4.16 (2H, d, J=4.4 Hz), 7.35 (2H, d, J=8.1 Hz), 7.40 to 7.53 (3H, m), 7.57 to 7.70 (2H, m), 8.08 (2H, d, J=8.1 Hz), 8.83 (1H, s), 12.25 (1H, s, br)

EXAMPLES 39 TO 78

In the same manner as in Example 1, 2, 3, 23, 24 or 36, the following compounds were obtained.

| Example | Compound | Characteristics. Physical properties |
|---|---|---|
| 39 | N-(5,6-dihydro-7H-cyclopenta[d]pyrimidin-4-yl)-4-{3-[1-(2-fluorobenzyl)piperidin-4-yl]propanoyl}aniline.2HCl (2HCl salt of Compound II-20 in Table 1) | (as ½$H_2O$ adduct) White powder m.p. 205 to 209° C. (decomposed) |
| 40 | N-(5,6-dihydro-7H-cyclopenta[d]pyrimidin-4-yl)-4-{3-[1-(4-chlorobenzyl)piperidin-4-yl]propanoyl}aniline (Compound II-50 in Table 1) | White powder m.p. 213 to 216° C. |
| 41 | N-(5,6-dihydro-7H-cyclopenta[d]pyrimidin-4-yl)-4-{3-[1-(3-chlorobenzyl)piperidin-4-yl]propanoyl}aniline.2HCl (2Hcl salt of Compound II-56 in Table 1) | (as ¼$H_2O$ adduct) Yellow crystal m.p. 189 to 191° C. |
| 42 | N-(5,6-dihydro-7H-cyclopenta[d]pyrimidin-4-yl)-4-{3-[1-(3-methoxybenzyl)piperidin-4-yl]propanoyl}aniline.2HCl (2HCl salt of Compound II-32 in Table 1) | (as ½$H_2O$ adduct) Yellowish white powder m.p. 186 to 188° C. |
| 43 | N-(5,6-dihydro-7H-cyclopenta[d]pyrimidin-4-yl)-4-{3-[1-(2-methoxybenzyl)piperidin-4-yl]propanoyl}aniline (Compound II-38 in Table 1) | Yellowish white powder m.p. 169.5 to 172 °C. |
| 44 | N-(5,6-dihydro-7H-cyclopenta[d]pyrimidin-4-yl)-4-{3-[1-(3-benzyloxybenzyl)piperidin-4-yl]propanoyl}aniline (Compound II-239 in Table 1) | (as ½$H_2O$ adduct) Yellowish white powder m.p. 193 to 195° C. |
| 45 | N-(5,6-dihydro-7H-cyclopenta[d]pyrimidin-4-yl)-4-{3-[1-(4-methylbenzyl)piperidin-4-yl]propanoyl}aniline.HCl (HCl salt of Compound II-68 in Table 1) | Yellowish white powder m.p. 192 to 195° C. (decomposed) |
| 46 | N-(5,6-dihydro-7H-cyclopenta[d]pyrimidin-4-yl)-4-{3-[1-(3-methylbenzyl)piperidin-4-yl]propanoyl}aniline (Compound II-214 in Table 1) | (as ½$H_2O$ adduct) White powder m.p. 116 to 117.5 °C. |
| 47 | N-(5,6-dihydro-7H-cyclopenta[d]pyrimidin-4-yl)-4-{3-[1-(4-trifluoromethylbenzyl)piperidin-4-yl]propanoyl}aniline (Compound II-80 in Table 1) | (as ¼$H_2O$ adduct) Yellowish white crystal m.p. 216 to 218° C. |
| 48 | N-(5,6-dihydro-7H-cyclopenta[d]pyrimidin-4-yl)-4-{3-[1-(3-trifluoromethylbenzyl)piperidin-4-yl]propanoyl}aniline (Compound II-232 in Table 1) | Yellow crystal m.p. 209 to 211.5 °C. |
| 49 | N-(5,6-dihydro-7H-cyclopenta[d]pyrimidin-4-yl)-4-{3-[1-(4-cyanobenzyl)piperidin-4-yl]propanoyl}aniline (Compound II-218 in Table 1) | White powder m.p. 180 to 182.5 °C. |
| 50 | N-(5,6-dihydro-7H-cyclopenta[d]pyrimidin-4-yl)-4-{3-[1-(3-cyanobenzyl)piperidin-4-yl]propanoyl}aniline (Compound II-225 in Table 1) | White powder m.p. 188 to 190° C. (decomposed) |
| 51 | N-(5,6-dihydro-7H-cyclopenta[d]pyrimidin-4-yl)-4-{3-[1-(1-naphthylmethyl)piperidin-4-yl]propanoyl}aniline (Compound II-224 in Table 1) | White powder m.p. 197 to 199° C. |
| 52 | N-(5,6-dihydro-7H-cyclopenta[d]pyrimidin-4-yl)-4-{3-[1-(sec-phenethyl)piperidin-4-yl]propanoyl}aniline (Compound II-86 in Table 1) | Pale yellow crystal m.p. 190 to 193° C. (decomposed) |
| 53 | N-(5,6-dihydro-7H-cyclopenta[d]pyrimidin-4-yl)-4-{3-[1-(2-pyridylmethyl)piperidin-4-yl]propanoyl}aniline (Compound II-110 in Table 1) | Yellow crystal m.p. 181.5 to 183 °C. |
| 54 | N-(5,6-dihydro-7H-cyclopenta[d]pyrimidin-4-yl)-4-{3-[1-(3-pyridylmethyl)piperidin-4-yl]propanoyl}aniline (Compound II-210 in Table 1) | Pale brown crystal m.p. 167 to 169° C. |
| 55 | N-(5,6-dihydro-7H-cyclopenta[d]pyrimidin-4-yl)-4-{3-[1-(4-pyridylmethyl)piperidin-4-yl]propanoyl}aniline (Compound II-116 in Table 1) | (as ¼$H_2O$ adduct) Pale brown crystal m.p. 174 to 175° C. |
| 56 | N-(5,6-dihydro-7H-cyclopenta[d]pyrimidin-4-yl)-4-{3-[1-(6-methyl-2-pyridylmethyl)piperidin-4-yl)propanoyl}aniline (Compound II-238 in Table 1) | Pale yellow crystal m.p. 200 to 201.5 °C. |
| 57 | (E)-N-(5,6-dihydro-7H-cyclopenta[d]pyrimidin-4-yl)-4-{3-[1-(2-thienylmethyl)piperidin-4-yl]propenoyl}aniline (Compound II-107 in Table 1) | Yellowish white crystal m.p. 199 to 200° C. |
| 58 | N-(5,6-dihydro-7H-cyclopenta[d]pyrimidin-4-yl)-4-{3-[1-(3,4-methylenedioxybenzyl)piperidin-4-yl)propanoyl}aniline (Compound II-231 in Table 1) | White crystal m.p. 198.5 to 200 °C. |
| 59 | N-(5,6-dihydro-7H-cyclopenta[d]pyrimidin-4-yl)-4-{3-[1-(3,4-ethylenedioxybenzyl)piperidin-4-yl]propanoyl}aniline (Compound II-235 in Table 1) | Yellowish white crystal m.p. 185 to 186° C. |
| 60 | N-(5,6-dihydro-7H-cyclopenta[d]pyrimidin-4-yl)-4-{3-[1-(2,3-dimethoxybenzyl)piperidin-4-yl]propanoyl}aniline (Compound II-233 in Table 1) | White crystal m.p. 179 to 181° C. |
| 61 | N-(6,6-dimethyl-5,6-dihydro-7H-cyclopenta[d]pyrimidin-4-yl)-4- | (as ½$H_2O$ adduct) Pale yellow crystal |

| Example | Compound | Characteristics. Physical properties |
|---|---|---|
| | [3-benzylpiperidin-4-yl)-propanoyl]aniline.2HCl (2HCl salt of Compound II-198 in Table 1) | m.p. 225 to 227° C. |
| 62 | N-(pyrimidin-4-yl)-4-[3-(1-benzylpiperidin-4-yl)propanoyl]aniline (Compound II-136 in Table 1) | Pale yellow crystal m.p. 149.5 to 151 °C. |
| 63 | N-(5-methylpyrimidin-4-yl)-4-[3-(1-benzylpiperidin-4-yl)propanoyl]aniline.2HCl (2HCl salt of Compound II-189 in Table 1) | (½H$_2$O adduct) White powder m.p. 180 to 184° C. |
| 64 | N-(5,6-diethylpyrimidin-4-yl)-4-[3-(1-benzylpiperidin-4-yl)propanoyl]aniline (Compound II-223 in Table 1) | White needle crystal m.p. 137 to 139° C. |
| 65 | N-(5-butyl-6-methylpyrimidin-4-yl)-4-[3-(1-benzylpiperidin-4-yl)propanoyl]aniline (Compound II-154 in Table 1) | White powder m.p. 149.5 to 151 °C. |
| 66 | N-(5-ethoxycarbonylpyrimidin-4-yl)-4-[3-(1-benzylpiperidin-4-yl)propanoyl]aniline (Compound II-222 in Table 1) | Pale yellow crystal m.p. 117 to 118.5 °C. |
| 67 | N-(6-ethoxypyrimidin-4-yl)-4-[3-(1-benzylpiperidin-4-yl)-propanoyl]aniline (Compound II-149 in Table 1) | Pale yellow crystal m.p. 168 to 170° C. |
| 68 | N-(6-chloro-5-methylpyrimidin-4-yl)-4-[3-(1-benzylpiperidin-4-yl)propanoyl]aniline (Compound II-190 in Table 1) | (as ½H$_2$O adduct) White needle crystal m.p. 175 to 177° C. |
| 69 | N-(5-chloropyrimidin-4-yl)-4-[3-(1-benzylpiperidin-4-yl)-propanoyl]aniline (Compound II-229 in Table 1) | Pale brown crystal m.p. 142 to 144° C. |
| 70 | N-(5-bromopyrimidin-4-yl)-4-[3-(1-benzylpiperidin-4-yl)propanoyl]aniline (Compound II-230 in Table 1) | Pale yellow crystal m.p. 151 to 153° C. |
| 71 | N-(5-nitro-6-methoxypyrimidin-4-yl)-4-[3-(1-benzylpiperidin-4-yl)propanoyl]aniline (Compound II-240 in Table 1) | Yellow crystal m.p. 126 to 128° C. |
| 72 | N-(5-methylpyrimidin-4-yl)-4-{3-[1-(2-pyridylmethyl)piperidin-4-yl)propanoyl]aniline (Compound II-248 in Table 1) | White crystal m.p. 142 to 143° C. |
| 73 | N-(5-amino-6-chloropyrimidin-4-yl)-4-[3-(1-benzylpiperidin-4-yl)propanoyl]aniline (Compound II-241 in Table 1) | (as ¼H$_2$O adduct) Yellowish orange crystal m.p. 163 to 165° C. |
| 74 | N-(5,6-dihydro-7H-cyclopenta[d]pyrimidin-4-yl)-4-{3-[1-(4-nitrobenzyl)piperidin-4-yl]-propanoyl}aniline (Compound II-74 in Table 1) | White powder m.p. 200 to 202° C. |
| 75 | N-(5,6-dihydro-7H-cyclopenta[d]pyrimidin-4-yl)-4-{3-[1-(3-nitrobenzyl)piperidin-4-yl]-propanoyl}aniline (Compound II-243 in Table 1) | White powder m.p. 184.5 to 186 °C. |
| 76 | N-(5,6-dihydro-7H-cyclopenta[d]pyrimidin-4-yl)-4-{3-[1-(4-aminobenzyl)piperidin-4-yl]-propanoyl}aniline (Compound II-271 in Table 1) | Pale brown powder m.p. 174 to 176.5 °C. |
| 77 | N-(5,6-dihydro-7H-cyclopenta[d]pyrimidin-4-yl)-4-{3-[1-(3-aminobenzyl)piperidin-4-yl]-propanoyl}aniline (Compound II-244 in Table 1) | (as ½H$_2$O adduct) White needle crystal m.p. 187 to 188° C. |
| 78 | N-(5,6-dihydro-7H-cyclopenta[d]pyrimidin-4-yl)-4-{3-[1-(4-hydroxybenzyl)piperidin-4-yl]-propanoyl}aniline (Compound II-44 in Table 1) | White powder NMR (δ, CD$_3$OD); 1.20–1.49 (3H, m), 1.58–1.80 (4H, m), 1.98–2.10 (2H, m), 2.15–2.27 (2H, m), 2.87–3.03 (8H, m), 3.59 (2H, s), 6.86 (2H, d, J=8.4Hz), 7.29 (2H, d, J=8.4 Hz), 7.90 (2H, d, J=8.8Hz), 7.98 (2H, d, J=8.8Hz), 8.51 (1H, s) |

EXAMPLES 79 TO 91

In the same manner as in Example 3, 25, 26, 27 or 31, the following compounds were obtained.

| Example | Compound | Characteristics. Physical properties |
|---|---|---|
| 79 | N-(5,6-dimethylpyrimidin-4-yl)-4-[(1-benzylpiperidin-4-yl)-acetyl]aniline (Compound II-234 in Table 1) | White crystal m.p. 212 to 214° C. |
| 80 | N-(5,6-dihydro-7H-cyclopenta[d]pyrimidin-4-yl)-4-[(1-benzylpiperidin-4-yl)acetyl]-2-methoxyaniline.2HCl (2HCl salt of Compound II-245 in Table 1) | (as ½H$_2$O adduct) White crystal m.p. 228 to 232° C. |
| 81 | N-(5,6,7,8-tetrahydroquinazolin-4-yl)-4-[(1-benzylpiperidin-4-yl)acetyl]-2-methoxyaniline.2HCl (2HCl salt of Compound II-246 in Table 1) | (as H$_2$O adduct) White crystal m.p. 215 to 219° C. |
| 82 | N-(5,6-dihydro-7H-cyclopenta[d]pyrimidin-4-yl)-4-[(1-benzylpiperidin-4-yl)acetyl]-2-chloroaniline (Compound II-247 in Table 1) | Pale yellow crystal m.p. 128 to 130° C. |
| 83 | N-(5,6-dihydro-7H-cyclopenta[d]pyrimidin-4-yl)-4-{[1-(4-fluorobenzyl)-4-piperidinyliden]acetyl}aniline (Compound II-10 in Table 1) | Yellow crystal m.p. 195 to 197° C. (decomposed) |
| 84 | N-(5,6-dihydro-7H-cyclopenta[d]pyrimidin-4-yl)-4-{[1-(4-fluorobenzyl)piperidin-4-yl]-acetyl}aniline (Compound II-7 in Table 1) | White crystal m.p. 191 to 193° C. |
| 85 | N-(5,6-dihydro-7H-cyclopenta[d]pyrimidin-4-yl)-4-{[1-(2-pyridylmethyl)piperidi-4-yl]-acetyl}aniline (Compound II-109 in Table 1) | White crystal m.p. 196 to 197.5 °C. |
| 86 | N-(5,6-dihydro-7H-cyclopenta[d]pyrimidin-4-yl)-4-{[1-(2-methoxybenzyl)piperidin-4-yl]-acetyl}aniline (Compound II-37 in Table 1) | Yellowish white crystal m.p. 168 to 170° C. |
| 87 | N-(5,6-dihydro-7H-cyclopenta[d]pyrimidin-4-yl)-4-{[1-(2-thienylmethyl)piperidin-4-yl]-acetyl}aniline (Compund II-103 in Table 1) | White crystal m.p. 197 to 199° C. |
| 88 | N-(5-methylpyrimidin-4-yl)-4-{[1-(2-thienylmethyl)piperidin-4-yl]acetyl}aniline (Compound II-258 in Table 1) | White crystal m.p. 209 to 211° C. |
| 89 | N-(5-methylpyrimidin-4-yl)-4-[(1-phenethylpiperidin-4-yl)-acetyl]aniline (Compound II-301 in Table 1) | White crystal m.p. 193 to 194° C. |
| 90 | N-(5-methylpyrimidin-4-yl)-4-[(1-diphenylmethylpiperidin-4-yl)acetyl]aniline (Compound II-302 in Table 1) | White crystal m.p. 195.5 to 197 °C. |
| 91 | N-(5,6-dihydro-7H-cyclopenta | White crystal |

| Example | Compound | Characteristics. Physical properties |
|---|---|---|
| | [d]pyrimidin-4-yl)-4-{[1-(2-furylmethyl)piperidin-4-yl]-acetyl}aniline (Compund II-269 in Table 1) | m.p. 207 to 209° C. |
| 92 | N-(5-methylpyrimidin-4-yl)-4-{[1-(3-phenylpropyl)piperidin-4-yl]acetyl}aniline (Compound II-317 in Table 1) | Yellowish white crystal m.p. 167.5 to 169 °C. |
| 93 | N-(5-ethylpyrimidin-4-yl)-4-[(1-benzylpiperidin-4-yl)-acetyl]aniline (Compound II-252 in Table 1) | White crystal m.p. 169 to 171° C. |
| 94 | N-(5-propylpyrimidin-4-yl)-4-[(1-benzylpiperidin-4-yl)-acetyl]aniline (Compound II-253 in Table 1) | Yellow crystal m.p. 140.5 to 141.5 °C. |
| 95 | N-(5-methylpyrimidin-4-yl)-4-{[1-(3-thienylmethyl)piperidin-4-yl]acetyl}aniline (Compound II-259 in Table 1) | White crystal m.p. 212 to 214° C. |
| 96 | N-(5,6-dihydro-7H-cyclopenta-[d]pyrimidin-4-yl)-4-{[1-(3-thienylmethyl)piperidin-4-yl]-acetyl}aniline (Compound II-267 in Table 1) | Yellowish white crystal m.p. 193 to 195° C. |
| 97 | N-(5-methylpyrimidin-4-yl)-4-[(1-benzylpiperidin-4-yl)-acetyl]-3-methoxyaniline (Compound II-266 in Table 1) | Pale brown crystal m.p. 168 to 170° C. |

Reference Example 1

4-[3-(1-benzylpiperidin-4-yl)propenoyl]nitrobenzene

Under ice cooling, 0.40 g of 64% sodium hydride was added to 3.03 g of diethyl (4-nitrobenzoylmethyl)phosphonate dissolved in 30 ml of tetrahydrofuran. After about 10 minutes, 4.07 g of 4-formyl-1-benzylpiperidine was added to the mixture. The mixture was stirred under ice cooling for 30 minutes and then stirred at room temperature for about 16 hours. After completion of the reaction, water was added to the reaction mixture, and the mixture was extracted with ethyl acetate. The extract was dried over anhydrous sodium sulfate, and the solvent was removed under reduced pressure. The obtained residue was applied to silica gel column chromatography to obtain 1.99 g of the title compound as pale yellow crystal.

Mass; m/z=350 ($M^+$)

NMR ($\delta$, $CDCl_3$); 1.47 to 1.70 (2H, m), 1.70 to 1.87 (2H, m), 1.97 to 2.16 (2H, m), 2.16 to 2.40 (1H, m), 2.86 to 3.02 (2H, m), 3.53 (2H, m), 6.82 (1H, dd, J=15.6 Hz, J=−1 Hz), 7.09 (1H, dd, J=15.6 Hz, J=6.4 Hz), 7.21 to 7.37 (5H, m), 8.03 (2H, d, J=8.8 Hz), 8.32 (2H, d, J=8.8 Hz)

Reference Example 2

(E)-4-[3-(1-benzylpiperidin-4-yl)propenoyl]aniline 1.27 g of (E)-4-[3-(1-benzylpiperidin-4-yl)propenoyl]nitrobenzene was added to a mixed solution of 10 ml of acetic acid and 2 ml of hydrochloric acid, and then 1.38 g of stannous chloride was added thereto under ice cooling. The mixture was stirred for 24 hours. During the reaction, 0.69 g of stannous chloride was further added twice. After completion of the reaction, the reaction mixture was condensed under reduced pressure to obtain 5.50 g of a crude product of the title compound. This was used without purification for the next reaction.

Mass; m/z=320 ($M^+$)

TLC Rf value; 0.42 (silica gel produced by Merck Co.; 60$F_{254}$, solvent; chloroform/methanol=9/1)

Reference Example 3

4-[3-(1-t-butoxycarbonylpiperidin-4-yl)propenoyl]nitrobenzene 0.28 g of lithium chloride, 0.85 g of diisopropylethylamine and 2.13 g of 4-formyl-1-t-butoxycarbonylpiperidine were added to 2.0 g of diethyl (4-nitrobenzoylmethyl)phosphonate dissolved in 20 ml of acetonitrile, and the mixture was stirred at room temperature for about 3 days. Then, water was added to the reaction mixture, and the mixture was extracted with toluene. The extract was dried over anhydrous sodium sulfate and condensed. The obtained residue was applied to silica gel column chromatography to obtain 1.76 g of the title compound as pale yellow crystal.

Mass (CI); m/z=261 ($M^+$−99)

NMR ($\delta$, $CDCl_3$); 1.37 to 1.53 (2H, m), 1.47 (9H, s), 1.77 to 1.86 (2H, m), 2.40 to 2.52 (2H, m), 2.74 to 2.87 (2H, m), 4.08 to 4.28 (2H, m), 6.85 (1H, dd, J=1.5 Hz, 15.6 Hz), 7.06 (1H, dd, J=6.4 Hz, 15.1 Hz), 8.05 (2H, d, J=8.8 Hz), 8.32 (2H, d, J=8.8 Hz)

Reference Example 4

(E)-4-[3-(piperidin-4-yl)propenoyl]nitrobenzene 3 ml of trifluoroacetic acid was added to 2.52 g of (E)-4-[3-(1-t-butoxycarbonylpiperidin-4-yl)propenoyl]nitrobenzene dissolved in 20 ml of methylene chloride, and the mixture was stirred at room temperature for 3 hours. Subsequently, 7 ml of trifluoroacetic acid was further added to the mixture, and the mixture was stirred for 3 hours. Then, the solvent was removed by distillation, and a saturated sodium hydrogen carbonate solution was added to the residue. After the mixture was extracted with ethyl acetate, the extract was dried over anhydrous sodium sulfate and condensed. The obtained solid was washed with methylene chloride to obtain 0.7 g of the title compound as pale yellow powder.

Mass (CI); m/z=261 ($M^+$+1)

NMR ($\delta$, $CDCl_3$-DMSO-$d_6$); 1.80 to 2.12 (4H, m), 2.30 to 2.70 (1H, m), 2.89 to 3.08 (2H, m), 3.44 to 3.68 (2H, m), 6.90 (1H, d, J=15 to 16 Hz), 7.04 (1H, dd, J=15 to 16 Hz, J=6 to 7 Hz), 8.06 (2H, d, J=8 to 9 Hz), 8.32 (2H, d, J=8 to 9 Hz)

Reference Example 5

(E)-4-{3-[1-(3-fluorobenzyl)piperidin-4-yl]propenoyl}nitrobenzene 1.11 g of 3-fluorobenzylbromide and 2.53 g of potassium carbonate were added to 3.0 g of (E)-4-[3-(piperidin-4-yl)propenoyl]nitrobenzene dissolved in 30 ml of dimethylformamide at room temperature, and the mixture was stirred for 2 hours. After completion of the reaction, water was added to the reaction mixture, and the mixture was extracted with ethyl acetate. The extract was dried over anhydrous sodium sulfate, and the solvent was removed under reduced pressure. The obtained residue was applied to silica gel column chromatography to obtain 1.06 g of the title compound as pale yellow crystal.

Mass (CI); m/z=369 ($M^+$+1)

NMR (δ, CDCl₃); 1.46 to 1.88 (4H, m), 2.00 to 2.12 (2H, m), 2.18 to 2.40 (1H, m), 2.84 to 3.50 (2H, m), 3.51 (2H, s), 6.82 (1H, dd, J=−1 Hz, 15.6 Hz), 6.88 to 6.99 (1H, m), 7.03 to 7.14 (3H, m), 7.20 to 7.34 (1H, m), 8.04 (2H, d, J=8.8 Hz), 8.31 (2H, d, J=8.8 Hz)

In the same manner as in Reference example 5, the following compounds were obtained.

Reference Example 6

(E)-4-{3-[1-(4-fluorobenzyl)piperidin-4-yl]propenoyl}-nitrobenzene

Orange powder

Mass (CI); m/z=369 (M⁺+1)

NMR (δ, CDCl₃); 1.45 to 1.88 (4H, m), 1.92 to 2.16 (2H, m), 2.16 to 2.40 (1H, m), 2.85 to 3.00 (2H, m), 3.47 (2H, s), 6.81 (1H, dd, J=−1 Hz, 15.6 Hz), 6.95 to 7.05 (2H, m), 7.07 (1H, dd, J=6.4 Hz, J=15.6 Hz), 7.24 to 7.31 (2H, m), 8.03 (2H, d, J=8.8 Hz), 8.31 (2H, d, J=8.8 Hz)

Reference Example 7

(E)-4-(3-[1-(4-methoxybenzyl)piperidin-4-yl]propenoyl)nitrobenzene

Brown oily product

Mass; m/z=380 (M⁺)

NMR (δ, CDCl₃); 1.46 to 1.84 (4H, m), 1.97 to 2.10 (2H, m), 2.20 to 2.35 (1H, m), 2.91 to 2.99 (2H, m), 3.46 (2H, s), 3.82 (3H, s), 6.88 to 6.92 (3H, m), 7.10 (1H, dd, J=6 to 7 Hz, 15 to 16 Hz), 7.22 to 7.35 (2H, m), 8.03 (2H, d, J=8 to 9 Hz), 8.32 (2H, d, J=8 to 9 Hz)

Reference Example 8

(E)-4-(3-[1-(4-picolyl)piperidin-4-yl]propenoyl)nitrobenzene

Brown crystal

Mass; m/z=351 (M⁺)

NMR (δ, CDCl₃); 1.55 to 1.66 (2H, m), 1.78 to 1.85 (2H, m), 1.85 to 2.14 (2H, m), 2.25 to 2.37 (1H, m), 2.87 to 2.97 (2H, m), 3.53 (2H, s), 6.83 (1H, d, J=15.6 Hz), 7.08 (1H, dd, J=6.8 Hz, J=15.6 Hz), 7.28 (2H, d, J=5.9 Hz), 8.05 (2H, d, J=8.8 Hz), 8.32 (2H, d, J=8.8 Hz), 8.55 (2H, d, J=5.9 Hz)

Reference Example 9

4-chloro-7-fluoro-5,6-dihydro-7H-cyclopenta[d]pyrimidine (1) 5.54 g of lithium hydroxide·hydrate was added to 24.2 g of 7-acetoxy-4-chloro-5,6-dihydro-7H-cyclopenta[d]pyrimidine dissolved in 150 ml of tetrahydrofuran, and the mixture was stirred at room temperature for about 20 hours. After the reaction, water was added to the reaction mixture, and then the mixture was extracted with chloroform. The extract was dried over anhydrous sodium sulfate and then condensed. The obtained residue was applied to silica gel column chromatography to obtain 10.5 g of 4-chloro-7-hydroxy-5,6-dihydro-7H-cyclopenta[d]pyrimidine.

Mass; m/z=170

NMR (δ, CDCl₃); 2.00 to 2.23 (1H, m), 2.52 to 2.73 (1H, m), 2.79 to 3.02 (1H, m), 3.02 to 3.24 (1H, m), 5.20 (1H, br), 5.30 (1H, t, J=8.0 Hz), 8.90 (1H, s)

(2) Under ice cooling, 3.9 ml of diethylaminosulfite trifluoride (DAST) was added dropwise to 5.00 g of 4-chloro-7-hydroxy-5,6-dihydro-7H-cyclopenta[d]pyrimidine obtained above dissolved in 40 ml of chloroform, and the mixture was stirred at the same temperature for 10 minutes. After the solvent was removed under reduced pressure, water was added to the mixture, and the mixture was extracted with ethyl acetate. The extract was dried over anhydrous sodium sulfate and condensed. The obtained residue was applied to silica gel column chromatography to obtain 3.09 g of the title compound as a yellow oily product.

Mass; m/z=172 (M⁺)

NMR (δ, CDCl₃); 2.23 to 2.77 (2H, m), 2.87 to 3.40 (2H, m), 5.78 to 5.89 and 6.05 to 6.18 (total 1H, each m), 9.01 (1H, s)

Reference Example 10

4-[3-(1-benzylpiperidin-4-yl)propanoyl]aniline 2.00 g of (E)-4-[3-(1-benzylpiperidin-4-yl)propenoyl]nitrobenzene was added to a mixed solvent of 30 ml of ethanol and 5 ml of acetic acid, and then 0.20 g of platinum oxide was added thereto. Thereafter, the mixture was stirred in a hydrogen stream at room temperature for 7.5 hours. After the reaction, the catalyst was removed by filtration, and the filtrate was condensed under reduced pressure. The obtained residue was applied to silica gel column chromatography to obtain 0.69 g of the title compound as pale yellow crystal.

Mass; m/z=322 (M⁺)

NMR (δ, CDCl₃); 1.32 to 1.54 (3H, m), 1.63 to 1.78 (4H, m), 2.14 to 2.25 (2H, m), 2.86 (2H, t, J=7.3 Hz), 3.09 to 3.18 (2H, m), 3.77 (2H, s), 6.63 (2H, d, J=8.8 Hz), 7.28 to 7.37 (5H, m), 7.78 (2H, d, J=8.8 Hz)

Reference Example 11

(E)-4-[3-(1-acetylpiperidin-4-yl) propenoyl]nitrobenzene

In the same manner as in Reference example 3 except for using 4-formyl-1-acetylpiperidine in place of 4-formyl-t-butoxycarbonylpiperidine, the reaction was carried out to obtain the title compound as yellowish orange solid.

Mass; m/z=302 (M⁺)

NMR (δ, CDCl₃); 1.36 to 1.57 (2H, m), 1.83 to 1.99 (2H, m), 2.12 (3H, s), 2.48 to 2.75 (2H, m), 3.10 to 3.25 (1H, m), 3.85 to 3.96 (1H, m), 4.63 to 4.75 (1H, m), 6.86 (1H, d, J=15.9 Hz), 7.06 (1H, dd, J=15.8 Hz, 6.7 Hz), 8.06 (2H, d, J=9.2 Hz), 8.32 (2H, d, J=9.2 Hz)

Reference Example 12

4-[3-(1-acetylpiperidin-4-yl) propanoyl]aniline

To 6.74 g of (E)-4-[3-(1-acetylpiperidin-4-yl)propenoyl] nitrobenzene were added 300 ml of methanol and 0.30 g of platinum oxide, and under a hydrogen stream, the mixture was stirred at room temperature for 3 hours. Then, the solid was removed by filtration, the solvent was removed by distillation under reduced pressure, and the obtained residue was applied to silica gel column chromatography to obtain 4.81 g of the title compound as brownish white powder.

Mass; m/z=274 (M⁺)

NMR (δ, CDCl₃); 1.02 to 1.25 (2H, m), 1.46 to 1.86 (5H, m), 2.08 (3H, s), 2.43 to 2.61 (1H, m), 2.90 (2H, t, J=7.3 Hz), 2.95 to 3.09 (1H, m), 3.70 to 3.86 (1H, m), 4.27(2H, s, br), 4.52 to 4.64 (1H, m), 6.65 (2H, d, J=8.6 Hz), 7.80 (2H, d, J=8.6 Hz)

Reference Example 13

N-acetyl-4-[(1-benzyl-4-hydroxypiperidin-4-yl)acetyl]aniline

A mixed solution comprising 140 ml of a tetrahydrofuran solution containing 10.00 g of 4-acetylaminoacetophenone and 10 ml of hexamethylphosphoric acid triamide (HMPA) was cooled to −60° C. under an argon stream, and then 83 ml of a tetrahydrofuran solution containing 1.5M of lithium diisopropylamide was added dropwise to the mixture. After completion of the dropwise addition, the mixture was stirred at −35° to −30° C. for 20 minutes and cooled again to −60° C. To the mixture was added dropwise 10.68 g of 1-benzyl-4-piperidone, and the temperature of the resulting mixture was gradually raised to room temperature. The reaction mixture was quenched to a saturated ammonium chloride aqueous solution, and 3.62 g of the precipitated title compound was collected by filtration. The filtrate was further extracted with ethyl acetate and condensed, and then the condensate was applied to silica gel column chromatography to obtain 8.28 g of the title compound.

White crystal

Mass (CI); m/z=349 ($M^+$+1-$H_2O$)

NMR ($\delta$, $CDCl_3$); 1.67 to 1.89 (4H, m), 2.22 (3H, s), 2.50 to 2.77 (4H, m), 3.05 (2H, s), 3.62 (2H, s), 4.14 (1H, s), 7.21 to 7.45 (5H, m), 7.66 (2H, d, J=9.2 Hz), 7.87 (2H, d, J=9.2 Hz), 8.07 (1H, s, br)

Reference Example 14

N-acetyl-4-[(1-benzyl-4-piperidinyliden)acetyl] aniline and N-acetyl-4-[(1-benzyl-1,2,5,6-tetrahydropyridin-4-yl)acetyl]aniline To a chloroform solution containing 11.90 g of N-acetyl-4-[(1-benzyl-4-hydroxypiperidin-4-yl)acetyl]aniline was added 15 ml of pyridine under ice cooling, and then 3.8 ml of thionyl chloride was added dropwise thereto. After completion of the dropwise addition, the mixture was stirred at room temperature for about 6 hours. After completion of the reaction, ice-water was added and then a 1N sodium hydroxide aqueous solution was added to the mixture to make it weak alkaline, then the mixture was extracted with chloroform. The extract was dried over anhydrous sodium sulfate and then condensed. The residue obtained was applied to silica gel column chromatography to obtain 7.11 g of the mixture of the title compounds.

Brown liquid

Mass (CI); m/z=349 ($M^+$+1)

NMR ($\delta$, $CDCl_3$); 2.20 (3H, s), 2.37 to 2.63, 2.85 to 3.02 and 3.60 (total 8H, each m), 3.53 and 3.56 (total 2H, each s), 5.52 and 6.62 (total 1H, m and s, respectively), 7.18 to 7.39 (5H, m), 7.62 (2H, d, J=8.6 Hz), 7.85 to 8.05 (3H, m)

Reference Example 15

N-acetyl-4-[(1-benzylpiperidin-4-yl)acetyl]aniline

In a mixed solution of 80 ml of ethanol and 30 ml of toluene was dissolved 7.10 g of the mixture of N-acetyl-4 [(1-benzyl-4-piperidinyliden)acetyl]aniline and N-acetyl-4 [(1-benzyl-1,2,5,6-tetrahydropyridin-4-yl)acetyl]aniline obtained in Reference example 14, and then 0.10 g of platinum oxide was added thereto. The mixture was stirred under a hydrogen stream for 5.5 hours. After the reaction, the catalyst was removed by filtration and condensed under reduced pressure. The residue obtained was applied to silica gel column chromatography to obtain 5.54 g of the title compound.

Pale yellow crystal

Mass (CI); m/z=351 ($M^+$+1)

NMR ($\delta$, $CDCl_3$); 1.25 to 1.44 (2H, m), 1.63 to 1.77 (2H, m), 1.88 to 2.07 (3H, m), 2.19 (3H, s), 2.76 to 2.92 (4H, m), 3.48 (2H, s), 7.18 to 7.38 (5H, m), 7.62 (2H, d, J=9.2 Hz), 7.89 (2H, d, J=9.2 Hz), 8.13 (1H, s, br)

Reference example 16

4-[(1-benzylpiperidin-4-yl)acetyl]aniline·2HCl salt 5.54 g of N-acetyl-4-[(1-benzylpiperidin-4-yl)acetyl] aniline was added to a mixed solution of 15 ml of ethanol and 20 ml of conc. hydrochloric acid, and then the mixture was heated under reflux for 4.5 hours. After the reaction, the reaction mixture was condensed under reduced pressure, and the obtained solid was washed with ethanol to obtain 6.20 g of the title compound.

Pale brown crystal

Mass (CI); m/z=309 ($M^+$+1)

NMR ($\delta$, $CDCl_3$-DMSO-$d_6$); 1.68 to 1.97 (4H, m), 2.07 to 2.28 (1H, m), 2.82 to 3.10 (4H, m), 3.29 to 3.43 (2H, m), 4.27 (2H, d, J=5.5 Hz), 7.18 (2H, d, J=8.7 Hz), 7.31 to 7.51 (3H, m), 7.58 to 7.76 (2H, m), 7.87 (2H, d, J=8.7 Hz)

Reference Example 17

N-t-butoxycarbonyl-4-[(1-benzyl-4-hydroxypiperidin-4-yl)acetyl]aniline 30 ml of tetrahydrofuran was added to 2.00 g of N-t-butoxycarbonyl-4-acetylaniline, and 8.8 ml of a 1.7M t-butyl lithium·pentane solution was added thereto under an argon stream at −78° C. Then, 1.41 g of 1-benzyl-4-piperidone was dissolved in 20 ml of tetrahydrofuran, and the solution was added dropwise. After stirring for 2 hours, a saturated ammonium chloride aqueous solution was added to the reaction mixture, and the mixture was extracted with ethyl acetate and dried over anhydrous sodium sulfate. The solvent was removed by distillation under reduced pressure, and the obtained residue was applied to silica gel column chromatography to obtain 2.07 g of the title compound as white powder.

Mass (CI); m/z=307 ($M^+$−118)

NMR ($\delta$, $CDCl_3$); 1.53 (9H, s), 1.60 to 1.75 (2H, m), 1.75 to 1.83 (2H, m), 2.43 to 2.53 (2H, m), 2.56 to 2.65 (2H, m), 3.06 (2H, s), 3.54 (2H, s), 4.10 (1H, s, br), 6.74 (1H, s, br), 7.23 to 7.35 (5H, m), 7.45 (2H, d, J=8.8 Hz), 7.89 (2H, d, J=8.8 Hz)

Reference Example 18

4-[(1-benzyl-4-hydroxypiperidin-4-yl)acetyl] aniline·trifluoroacetate 30 ml of chloroform was added to 2.07 g of N-t-butoxycarbonyl-4-[(1-benzyl-4-hydroxypiperidin-4-yl)acetyl] aniline, trifluoroacetic acid was added thereto three times in a total amount of 8 ml, and the mixture was stirred at room temperature. Thereafter, the solvent was removed by distillation under reduced pressure, and the obtained residue was applied to silica gel column chromatography to obtain 1.14 g of the title compound as reddish white powder.

Mass (CI); m/z=325 (M$^+$+1)

NMR (δ, CDCl$_3$); 1.88 to 1.96 (2H, m), 2.01 to 2.16 (2H, m), 3.03 (2H, s), 3.13 to 3.36 (4H, m), 4.19 (2H, s), 5.01 (2H, br), 6.63 (2H, d, J=8.8 Hz), 7.38 to 7.55 (5H, m), 7.73 (2H, d, J=8.8 Hz), 12.07 (1H, br)

Reference Example 19

(a) N-t-butoxycarbonyl-4-[(1-benzyl-4-piperidinyliden)acetyl]aniline and (b) N-t-butoxycarbonyl-4-[(1-benzyl-1,2,5,6-tetrahydropyridin-4-yl)acetyl]aniline 100 ml of chloroform was added to 14.9 g of N-t-butoxycarbonyl-4-[2-(1-benzyl-4-hydroxypiperidin-4-yl)acetyl]aniline. After 3.1 ml of thionyl chloride was added to the mixture under ice cooling, 11.8 ml of triethylamine was added dropwise thereto. After the mixture was stirred at room temperature for 1 hour, water was added to the reaction mixture, and the mixture was extracted with chloroform. The extract was dried over anhydrous sodium sulfate, and the solvent was removed by distillation under reduced pressure. The obtained residue was applied to silica gel column chromatography to obtain the title compounds, respectively.

Compound of (a)

White powder

Mass (CI); m/z=407 (M$^+$+1)

NMR (δ, CDCl$_3$); 1.57 (9H, s), 2.38 to 2.49 (2H, m), 2.49 to 2.67 (4H, m), 2.86 to 3.00 (2H, m), 3.56 (2H, s), 6.61 (1H, s), 6.66 (1H, s), 7.23 to 7.39 (5H, m), 7.44 (2H, d, J=8.5 Hz), 7.90 (2H, d, J=8.5 Hz)

Compound of (b)

White powder

Mass (CI); m/z=407 (M$^+$+1)

NMR (δ, CDCl$_3$); 1.52 (9H, s), 2.11 to 2.22 (2H, m), 2.22 to 2.54 (2H, m), 2.95 to 3.04 (2H, m), 3.57 (4H, s), 5.50 to 5.56 (1H, m), 6.76 (1H, s, br), 7.19 to 7.39 (5H, m), 7.43 (2H, d, J=8.8 Hz), 7.92 (2H, d, J=8.8 Hz)

Reference Example 20

4-[(1-benzyl-4-piperidinylidene)acetyl]aniline 4.12 g of N-t-butoxycarbonyl-4-[(1-benzyl-4-piperidinyliden)acetyl]aniline was added to 50 ml of chloroform, and then 10 ml of trifluoroacetic acid was added thereto. The mixture was stirred at room temperature for 4 hours. After the reaction, the reaction mixture was condensed under reduced pressure, and the residue was dissolved in chloroform. Then, the solution was neutralized by adding a 28% sodium methylate·methanol solution thereto. The residue obtained by condensation under reduced pressure was applied to silica gel column chromatography to obtain 2.33 g of the title compound as bluish green powder.

Mass; m/z=306 (M$^+$)

NMR (δ, CDCl$_3$); 2.29 to 2.69 (2H, m), 2.69 to 3.05 (2H, m), 3.31 to 3.86 (4H, m), 4.22 (2H, s), 6.64 (2H, d, J=8.6 Hz), 6.71 (1H, s), 7.73 (2H, d, J=9.2 Hz)

Reference Example 21

N-t-butoxycarbonyl-4-[(1-acetyl-4-hydroxypiperidin-4-yl)acetyl]aniline

In the same manner as in Reference example 17 except for using 1-acetyl-4-piperidone in place of 1-benzyl-4-piperidone, the reaction was carried out to obtain the title compound as white solid.

Mass (SIMS); 377 (M$^+$+1)

NMR (δ, CDCl$_3$); 1.37 to 1.62 (2H, m), 1.53 (9H, s ), 1.75 to 1.95 (2H, m), 2.10 (3H, s), 3.06 (2H, s), 3.47 to 3.67 (2H, m), 4.32 to 4.47 (2H, m), 7.07 (1H, s, br), 7.50 (2H, d, J=8.8 Hz ), 7.88 (2H, d, J=8.8 Hz )

Reference Example 22

N-t-butoxycarbonyl-4-[(1-acetyl-4-piperidinyliden) acetyl]aniline and N-t-butoxycarbonyl-4-[(1-acetyl-1,2,5,6-tetrahydropyridin-4-yl) acetyl]aniline In the same manner as in Reference example 14, the reaction was carried out by using the compound obtained in Reference example 21 to obtain the mixture of the title compounds.

Yellowish white powder

Mass (CI); m/z=359 (M$^+$+1)

NMR (δ, CDCl$_3$); 1.53 (9H, s), 2.12 and 2.16 (total 3H, each s), 1.98 to 2.30, 2.38 to 2.57, 2.85 to 3.01, 3.38 to 3.82 and 3.82 to 4.13 (total 8H, each m), 5.45 to 5.64 and 7.01 (total 1H, m and s, respectively), 6.75 and 7.01 (total 1H, s, respectively), 7.47 (2H, d, J=8.8 Hz), 7.91 (2H, d, J=8.8 Hz)

Reference Example 23

N-t-butoxycarbonyl-4-[(1-acetylpiperidin-4-yl)acetyl]aniline

In the same manner as in Reference example 15, the reaction was carried out by using the mixture obtained in Reference example 22 to obtain the title compound as white powder.

Mass (CI); m/z=261 (M$^+$–99)

NMR (δ, CDCl$_3$); 1.11 to 1.32 (2H, m), 1.53 (9H, s), 1.72 to 1.90 (2H, m), 2.08 (3H, s), 2.15 to 2.34 (1H, m), 2.53 to 2.66 (1H, m), 2.82 to 2.90 (2H, m), 3.02 to 3.17 (1H, m), 3.73 to 3.85 (1H, m), 4.57 to 4.68 (1H, m), 6.79 (1H, s, br), 7.46 (2H, d, J=8.8 Hz), 7.90 (2H, d, J=8.8 Hz)

Reference Example 24

4-[(1-acetylpiperidin-4-yl) acetyl]aniline 50 ml of chloroform was added to 6.90 g of N-t-butoxycarbonyl-[4-(1-acetylpiperidin-4-yl)acetyl]aniline, and trifluoroacetic acid was added to the mixture at room temperature until no foaming occurred. The solvent was removed by distillation under reduced pressure, water was added to the residue, and the mixture was neutralized with sodium hydrogen carbonate and then extracted with chloroform. After the extract was dried over anhydrous sodium sulfate, the solvent was removed by distillation under reduced pressure. The obtained residue was applied to silica gel column chromatography to obtain 3.56 g of the title compound as yellow solid.

Mass (CI); m/z=261 (M$^+$+1)

NMR (δ, CDCl₃); 1.10 to 1.30 (2H, m), 1.68 to 1.91 (2H, m), 2.08 (3H, s), 2.12 to 2.34 (1H, m), 2.48 to 2.68 (1H, m), 2.68 to 2.93 (2H, m), 3.00 to 3.17 (1H, m), 3.72 to 3.85 (1H, m), 4.54 (1H, m), 6.66 (2H, d, J=8.8 Hz), 7.80 (2H, d, J=8.8 Hz)

Reference Example 25

N-t-butoxycarbonyl-4-[4-(1-benzylpiperidin-4-yl)-3-hydroxybutanoyl]aniline 50 ml of tetrahydrofuran was added to 3.80 g of N-t-butoxycarbonyl-4-acetylaniline, and 19.0 ml of a 1.7M t-butyl lithium·pentane solution was added dropwise thereto under an argon stream at −78° C. Subsequently, a solution of 3.50 g of (1-benzylpiperidin-4-yl)acetaldehyde dissolved in 10 ml of tetrahydrofuran was added to the mixture, and the resulting mixture was stirred until its temperature was returned to room temperature. Then, a saturated ammonium chloride aqueous solution was added to the reaction mixture, the mixture was extracted with ethyl acetate, and the extract was dried over anhydrous sodium sulfate. Then, the solvent was removed by distillation under reduced pressure, and the obtained residue was applied to silica gel column chromatography to obtain 4.57 g of the title compound as white powder.

Mass (CI); m/z=453 (M⁺+1)

NMR (δ, CDCl₃); 1.15 to 1.42 (4H, m), 1.42 to 1.72 (4H, m), 1.53 (9H, s), 1.72 to 1.86 (1H, m), 1.86 to 2.08 (2H, m), 2.84 to 2.95 (2H, m), 3.50 (2H, s), 4.23 to 4.38 (1H, m), 6.86 (1H, s, br), 7.13 to 7.40 (5H, m), 7.45 (2H, d, J=8.8 Hz), 7.89 (2H, d, J=8.8 Hz)

Reference Example 26

4-[4-(1-benzylpiperidin-4-yl)-3-hydroxybutanoyl]aniline·trifluoroacetate 50 ml of dichloromethane was added to 4.55 g of N-t-butoxycarbonyl-4-[4-(1-benzylpiperidin-4-yl)-3-hydroxybutanoyl]aniline, and trifluoroacetic acid was added to the mixture at room temperature until no foaming occurred. Then, the solvent was removed by distillation under reduced pressure, and the obtained residue was applied to silica gel column chromatography to obtain 1.21 g of the title compound as white powder.

Mass (CI); m/z=353 (M⁺+1)

NMR (δ, CDCl₃); 1.22 to 2.08 (7H, m), 2.62 to 2.84 (2H, m), 2.94 (2H, d, J=5.9 Hz), 3.42 to 3.62 (2H, m), 4.20 (3H, m, br), 6.63 (2H, d, J=8.8 Hz), 7.36 to 7.55 (5H, m), 7.73 (2H, d, J=8.8 Hz)

Reference Examples 27 TO 42

In the same manner as in Reference example 5, the following compounds were obtained.

| Reference example No. | Compound (characteristics) | Mass (m/z) | NMR (δ, CDCl₃) |
|---|---|---|---|
| 27 | (E)-4-{3-[1-(2-fluorobenzyl)-piperidin-4-yl]propenoyl}-nitrobenzene (brown liquid) | 368 (M⁺) | 1.54 to 1.67 (2H, m), 1.77 to 1.86 (2H, m), 2.08 to 2.18 (2H, m), 2.22 to 2.37 (1H, m), 2.92 to 3.01 (2H, m), 3.62 (2H, s), 6.82 (1H, d, J=15.6Hz), 7.00 to 7.17 (3H, m), 7.21 to 7.30 (1H, m), 7.35 to 7.43 (1H, m), 8.03 (2H, d, J=8.8Hz), 8.31 (2H, d, J=8.8Hz) |
| 28 | (E)-4-{3-[1-(3-chlorobenzyl)-piperidin-4-yl]propenoyl}-nitrobenzene (brown crystal) | 384 (M⁺) | 1.46 to 1.71 (2H, m), 1.75 to 1.89 (2H, m), 2.00 to 2.19 (2H, m), 2.22 to 2.39 (1H, m), 2.85 to 3.04 (2H, m), 3.52 (2H, s), 6.83 (1H, d, J=15Hz), 7.09 (1H, dd, J=15Hz, 6Hz), 7.15 to 7.41 (4H, m), 8.04 (2H, d, J=9Hz), 8.32 (2H, d, J=9Hz) |
| 29 | (E)-4-{3-[1-(3-methoxybenzyl)-piperidin-4-yl]propenoyl}-nitrobenzene (yellowish brown crystal) | 381 (CI) (M⁺+1) | 1.53 to 1.67 (2H, m), 1.75 to 1.85 (2H, m), 2.01 to 2.13 (2H, m), 2.24 to 2.37 (1H, m), 2.93 to 3.01 (2H, m), 3.51 (2H, s), 3.82 (3H, s), 6.82 (1H, d, J=15.6Hz), 6.80 to 6.84 (1H, m), 6.86 to 6.95 (1H, m), 7.08 (1H, dd, J=15.6Hz, 8.7Hz), 7.22 to 7.28 (1H, m), 8.03 (2H, d, J=8.8Hz), 8.31 (2H, d, J=8.8Hz) |
| 30 | (E)-4-{3-[1-(2-methoxybenzyl)-piperidin-4-yl]propenoyl}-nitrobenzene (pale yellow crystal) | 380 (M⁺) | 1.52 to 1.70 (2H, m), 1.70 to 1.85 (2H, m), 2.05 to 2.20 (2H, m), 2.20 to 2.38 (1H, m), 2.94 to 3.06 (2H, m), 3.59 (2H, s), 3.82 (3H, s), 6.81 (1H, d, J=15.3Hz), 6.84 to 6.99 (2H, m), 7.08 (1H, dd, J=15.3 Hz, 6.7Hz), 7.19 to 7.29 (1H, m), 7.35 (1H, d, J=7.3Hz), 8.03 (2H, d, J=8.5Hz), 8.31 (2H, d, J=8.5Hz) |
| 31 | (E)-4-{3-[1-(3-methylbenzyl)-piperidin-4-yl]propenoyl}-nitrobenzene | 364 (M⁺) | 1.47 to 1.71 (2H, m), 1.71 to 1.89 (2H, m), 1.96 to 2.13 (2H, m), 2.21 to 2.40 (1H, m), 2.35 (3H, s), 2.88 to 3.03 (2H, m), 3.49 (2H, s), 6.82 (1H, d, J=16.9Hz), |

-continued

| Reference example No. | Compound (characteristics) | Mass (m/z) | NMR (δ, CDCl₃) |
|---|---|---|---|
| | (yellow crystal) | | 7.02 to 7.29 (5H, m), 8.03 (2H, d, J=8.8Hz), 8.31 (2H, d, J=8.8Hz) |
| 32 | (E)-4-{3-[1-(3-trifluoromethyl-benzyl)piperidin-4-yl]propenoyl}nitrobenzene (brown liquid) | 418 (M⁺) | 1.49 to 1.70 (2H, m), 1.70 to 1.87 (2H, m), 2.00 to 2.16 (2H, m), 2.22 to 2.40 (1H, m), 2.85 to 2.97 (2H, m), 3.57 (2H, s), 6.83 (1H, d, J=15.9Hz), 7.09 (1H, dd, J=15.9Hz, 6.7Hz), 7.37 to 7.48 (1H, m), 7.48 to 7.58 (2H, m), 7.60 (1H, s), 8.04 (2H, d, J=9.2Hz), 8.31 (2H, d, J=9.2Hz) |
| 33 | (E)-4-{3-[1-(4-cyanobenzyl)-piperidin-4-yl]propenoyl}-nitrobenzene (yellow crystal) | 375 (M⁺) | 1.48 to 1.70 (2H, m), 1.75 to 1.87 (2H, m), 2.03 to 2.17 (2H, m), 2.23 to 2.40 (1H, m), 2.82 to 2.97 (2H, m), 3.56 (2H, s), 6.83 (1H, d, J=15.4Hz), 7.08 (1H, dd, J=15.4Hz, 6.6Hz), 7.46 (2H, d, J=8.1Hz), 7.61 (2H, d, J=8.1Hz), 8.04 (2H, d, J=8.8Hz), 8.32 (2H, d, 8.8hz) |
| 34 | (E)-4-{3-[1-(3-cyanobenzyl)-piperidin-4-yl]propenoyl}-nitrobenzene (brown liquid) | 375 (M⁺) | 1.47 to 1.70 (2H, m), 1.75 to 1.89 (2H, m), 2.02 to 2.18 (2H, m), 2.22 to 2.44 (1H, m), 2.82 to 2.96 (2H, m), 3.59 (2H, s), 6.84 (1H, d, J=15.4Hz), 7.09 (1H, dd, J=15.4Hz, 6.6Hz), 7.37 to 7.50 (1H, m), 7.50 to 7.62 (2H, m), 7.66 (1H, s), 8.05 (2H, d, J=8.8Hz), 8.32 (2H, d, J=8.8Hz) |
| 35 | (E)-4-{3-[1-(1-naphthylmethyl)-piperidin-4-yl]propenoyl}-nitrobenzene (brown liquid) | 400 (M⁺) | 1.46 to 1.66 (2H, m), 1.71 to 1.85 (2H, m), 2.04 to 2.22 (2H, m), 2.22 to 2.40 (1H, m), 2.93 to 3.07 (2H, m), 3.91 (2H, s), 6.80 (1H, d, J=16.3Hz), 7.07 (1H, dd, J=16.3Hz, 6.6Hz), 7.37 to 7.55 (4H, m), 7.74 to 7.89 (2H, m), 8.02 (2H, d, J=8.8Hz), 8.30 (3H, d, 8.8Hz) |
| 36 | (E)-4-{3-[1-(β-phenethyl)piperidin-4-yl]propenoyl}nitrobenzene (reddish brown liquid) | 364 (M⁺) | 1.39 (3H, d, J=6.6Hz), 1.43 to 2.13 (6H, m), 2.13 to 2.32 (1H, m), 2.81 to 2.93 (1H, m), 3.04 to 3.17 (1H, m), 3.46 (1H, q, J=6.6Hz), 6.79 (1H, d, J=15.4Hz), 7.06 (1H, dd, J=15.4Hz, 6.6Hz), 7.17 to 7.39 (5H, m), 8.02 (2H, d, J=8.8Hz), 8.30 (2H, d, J=8.8Hz) |
| 37 | (E)-4-{3-[1-(3-pyridylmethyl)-piperidiin-4-yl]propenoyl}-nitrobenzene (reddish brown crystal) | 352 (CI) (M⁺+1) | 1.49 to 1.68 (2H, m), 1.74 to 1.88 (2H, m), 2.01 to 2.16 (2H, m), 2.22 to 2.39 (1H, m), 2.83 to 2.99 (2H, m), 3.54 (2H, s), 6.83 (1H, d, J=15.9Hz), 7.08 (1H, dd, J=15.9 Hz, 6.7Hz), 7.21 to 7.30 (1H, m), 7.63 to 7.72 (1H, m), 8.04 (2H, d, J=9.2Hz), 8.31 (2H, d, J=9.2Hz), 8.46 to 8.58 (2H, m) |
| 38 | (E)-4-{3-[1-(6-methyl-2-pyridyl-methyl)piperidin-4-yl]propenoyl}-nitrobenzene (yellowish brown crystal) | 366 (CI) (M⁺+1) | 1.53 to 1.72 (2H,m), 1.74 to 1.86 (2H, m), 2.09 to 2.24 (2H, m), 2.24 to 2.39 (1H, m), 2.55 (3H, s), 2.93 to 3.03 (2H, m), 3.65 (2H, s), 6.83 (1H, d, J=15.3Hz), 7.03 (1H, d, J=7.9Hz), 7.09 (1H, dd, J=15.3Hz, 6.7Hz), 7.55 (1H, t, J=7.9Hz), 8.04 (2H, d, J=9.2Hz), 8.31 (2H, d, J=9.2Hz) |
| 39 | (E)-4-{3-[1-(2-thienylmethyl)-piperidin-4-yl]propenoyl}-nitrobenzene (yellow crystal) | 357 (CI) (M⁺+1) | 1.54 to 1.66 (2H, m), 1.76 to 1.85 (2H, m), 2.03 to 2.15 (2H, m), 2.23 to 2.36 (1H, m), 2.96 to 3.04 (2H, m), 3.75 (2H, s), 6.82 (1H, d, J=15.6Hz), 6.99 to 7.03 (1H, m), 7.03 to 7.06 (1H, m), 7.08 (1H, dd, J=15.6Hz, 6.4Hz), 7.24 (1H, d, J=6.4Hz), 8.02 (2H, d, J=8.8Hz), 8.31 (2H, d, J=8.8Hz) |
| 40 | (E)-4-{3-[1-(3,4-methylenedioxy- | 394 (M⁺) | 1.48 to 1.67 (2H, m), 1.74 to 1.87 (2H, m), 1.96 to 2.11 (2H, m), |

-continued

| Reference example No. | Compound (characteristics) | Mass (m/z) | NMR (δ, CDCl₃) |
|---|---|---|---|
| | benzyl)piperidin-4-yl]propenoyl}nitrobenzene (pale yellow crystal) | | 2.20 to 2.37 (1H, m), 2.88 to 3.00 (2H, m), 3.43 (2H, s), 5.94 (2H, s), 6.74 (2H, s), 6.82 (1H, d, J=15.9Hz), 6.85 (1H, s), 7.08 (1H, dd, J=15.9Hz, 6.7Hz), 8.03 (2H, d, J=9.2Hz), 8.31 (2H, d, J=9.2Hz) |
| 41 | (E)-4-{3-[1-(3,4-ethylenedioxybenzyl)piperidin-4-yl]propenoyl}nitrobenzene (brown liquid) | 409 (CI) (M⁺+1) | 1.49 to 1.72 (2H, m), 1.72 to 1.84 (2H, m), 1.95 to 2.11 (2H, m), 2.20 to 2.36 (1H, m), 2.89 to 2.99 (2H, m), 3.41 (2H, s), 4.25 (4H, s), 6.81 (1H, d, J=15.3Hz), 6.79 to 6.84 (3H, m), 7.08 (1H, dd, J=15.3Hz, 6.7Hz), 8.03 (2H, d, J=9.2Hz), 8.31 (2H, d, J=8.8Hz) |
| 42 | (E)-4-{3-[1-(2,3-dimethoxybenzyl)piperidin-4-yl]propenoyl}-nitrobenzene (brown liquid) | 410 (M⁺) | 1.46 to 1.66 (2H, m), 1.73 to 1.85 (2H, m), 2.02 to 2.18 (2H, m), 2.18 to 2.37 (1H, m), 2.94 to 3.03 (2H, m), 3.57 (2H, s), 3.83 (3H, s), 3.87 (3H, s), 6.80 (1H, d, J=15.9Hz), 6.80 to 6.86 (1H, m), 6.95 to 7.00 (2H, m), 7.07 (1H, dd, J=15.3Hz, 6.7Hz), 8.03 (2H, d, J=9.2Hz), 8.31 (2H, d, J=9.2Hz) |

Reference Examples 43 to 56

In the same manner as in Reference example 10, the following compounds were obtained.

| Reference example No. | Compound (characteristics) | Mass (m/z) | NMR (δ, CDCl₃) |
|---|---|---|---|
| 43 | 4-{3-[1-(2-fluorobenzyl)-piperidin-4-yl]propanoyl}-aniline (pale yellow crystal) | 340 (M⁺) | 1.19 to 1.40 (3H, m), 1.54 to 1.78 (4H, m), 1.91 to 2.09 (2H, m), 2.77 to 2.96 (4H, m), 3.57 (2H, s), 4.09 (2H, s, br), 6.63 (2H, d, J=8.8Hz), 6.95 to 7.13 (2H, m), 7.16 to 7.29 (1H, m), 7.34 to 7.43 (1H, m), 7.80 (2H, d, J=8.8Hz) |
| 44 | 4-{3-[1-(4-chlorobenzyl)-piperidin-4-yl]propanoyl}-aniline (white crystal) | 356 (M⁺) | 1.23 to 1.42 (3H, m), 1.63 to 1.75 (4H, m), 1.85 to 2.04 (2H, m), 2.81 to 2.95 (4H, m), 3.39 to 3.54 (2H, br), 4.09 (2H, br), 6.64 (2H, d), 7.23 to 7.33 (4H, m), 7.80 (2H, d) |
| 45 | 4-{3-[1-(2-methoxybenzyl)-piperidin-4-yl]propanoyl}-aniline.HCl salt (yellowish brown crystal) | 352 (M⁺) | (CDCl₃DMSO-d₆) 1.38 to 1.59 (1H, m), 1.59 to 1.90 (6H, m), 2.38 to 2.62 (2H, m), 2.86 (2H, t, J=7.3Hz), 3.16 to 3.33 (2H, m), 3.85 (3H, s), 4.01 (2H, s, br), 4.69 (2H, s, br), 6.64 (2H, d, J=8.6Hz), 6.90 to 7.03 (2H, m), 7.30 to 7.40 (1H, m), 7.54 to 7.63 (1H, m), 7.74 (2H, d, J=8.6Hz) |
| 46 | 4-{3-[1-(3-benzyloxybenzyl)piperidin-4-yl]propanoyl}-aniline (brown liquid) | 428 (M⁺) | 1.20 to 1.39 (3H, m), 1.59 to 1.74 (4H, m), 1.85 to 2.00 (2H, m), 2.79 to 3.01 (4H, m), 3.46 (2H, s), 4.09 (2H, s, br), 5.06 (2H, s), 6.64 (2H, d, J=8.6Hz), 6.82 to 6.91 (2H, m), 7.18 (1H, s), 7.19 to 7.27 (1H, m), 7.31 to 7.48 (5H, m), 7.80 (2H, d, J=8.6Hz) |
| 47 | 4-{3-[1-(3-methylbenzyl)-piperidin-4-yl]propanoyl}-aniline (yellow crystal) | 336 (M⁺) | 1.19 to 1.40 (3H, m), 1.53 to 1.77 (4H, m), 1.84 to 2.01 (2H, m), 2.34 (3H, s), 2.76 to 2.96 (4H, m), 3.44 (2H, s), 4.11 (2H, s, br), 6.63 (2H, d, J=8.8Hz), 7.00 to 7.26 (4H, m), 7.80 (2H, d, J=8.8Hz) |

| Reference example No. | Compound (characteristics) | Mass (m/z) | NMR (δ, CDCl$_3$) |
|---|---|---|---|
| 48 | 4-{3-[1-(3-tri-fluorobenzyl)-piperidin-4-yl]propanoyl}-aniline (yellow crystal) | 390 (M$^+$) | 1.17 to 1.42 (3H, m), 1.56 to 1.80 (4H, m), 1.88 to 2.04 (2H, m), 2.79 to 2.94 (4H, m), 3.51 (2H, s), 4.12 (2H, s, br), 6.64 (2H, d, J=8.6Hz), 7.37 to 7.45 (1H, m), 7.45 to 7.56 (2H, m), 7.57 (1H, s), 7.80 (1H, d, J=8.6Hz) |
| 49 | 4-{3-[1-(4-cyanobenzyl)-piperidin-4-yl]propanoyl}-aniline (pale brown crystal) | 347 (M$^+$) | (CDCl$_3$-DMSO-d$_6$) 1.13 to 1.40 (3H, m), 1.51 to 1.78 (4H, m), 1.87 to 2.05 (2H, m), 2.69 to 2.92 (4H, m), 3.52 (2H, s), 4.98 (2H, s, br), 6.63 (2H, d, J=8.8Hz), 7.46 (2H, d, J=8.1Hz), 7.60 (2H, d, J=8.1Hz), 7.74 (2H, d, J=8.8Hz) |
| 50 | 4-{3-[1-(2-naphthylmethyl)-piperidin-4-yl]propanoyl}-aniline.HCl salt (yellowish brown crystal) | 372 (M$^+$) | (CDCl$_3$-DMSO-d$_6$) 1.28 to 1.50 (1H, m), 1.50 to 1.81 (6H, m), 2.10 to 2.50 (2H, m), 2.83 (2H, t, J=7.3Hz), 2.93 to 3.27 (2H, m), 3.81 to 4.27 (2H, br), 5.29 (2H, s), 6.61 (2H, d, J=8.8Hz), 7.40 to 7.59 (4H, m), 7.69 (2H, d, J=8.8Hz), 7.76 to 7.92 (2H, m), 8.23 to 8.34 (1H, m) |
| 51 | 4-{3-[1-(2-pyridylmethyl)-piperidin-4-yl]propanoyl}-aniline (yellow crystal) | 323 (M$^+$) | 1.20 to 1.45 (3H, m), 1.50 to 1.80 (4H, m), 1.95 to 2.15 (2H, m), 2.80 to 3.00 (4H, m), 3.64 (2H, s), 4.09 (2H, s, br), 6.64 (2H, d, J=8.8Hz), 7.10 to 7.20 (1H, m), 7.38 to 7.47 (1H, m), 7.60 to 7.69 (1H, m), 7.81 (2H, d, J=8.8Hz), 8.52 to 8.60 (1H, m) |
| 52 | 4-{3-[1-(3-pyridylmethyl)-piperidin-4-yl]propanoyl}-aniline (pale yellow crystal) | 323 (M$^+$) | 1.13 to 1.40 (3H, m), 1.54 to 1.78 (4H, m), 1.84 to 2.03 (2H, m), 2.75 to 2.93 (4H, m), 3.48 (2H, s), 4.19 (2H, s, br), 6.64 (2H, d, J=8.8Hz), 7.19 to 7.30 (1H, m), 7.62 to 7.71 (1H, m), 7.80 (2H, d, J=8.8Hz), 8.45 to 8.58 (2H, m) |
| 53 | 4-{3-[1-(4-pyridylmethyl)-piperidin-4-yl]propanoyl}-aniline (pale yellow crystal) | 323 (M$^+$) | 1.18 to 1.41 (3H, m), 1.50 to 1.79 (4H, m), 1.89 to 2.07 (2H, m), 2.73 to 2.93 (4H, m), 3.48 (2H, s), 4.10 (2H, s, br), 6.64 (2H, d, J=8.8Hz), 7.27 (2H, d, J=5.9Hz), 7.81 (2H, d, J=8.8Hz), 8.52 (2H, d, J=5.9Hz) |
| 54 | 4-{3-[1-(6-methyl-4-pyridylmethyl)piperidin-4-yl]propanoyl}aniline (yellow crystal) | 338 (CI) (M$^+$+1) | 1.26 to 1.46 (3H, m), 1.62 to 1.76 (4H, m), 1.97 to 2.13 (2H, m), 2.54 (3H, s), 2.83 to 2.95 (4H, m), 3.61 (2H, s), 4.10 (2H, s, br), 6.64 (2H, d, J=9.2Hz), 7.00 (1H, d, J=7.3Hz), 7.21 to 7.30 (1H, m), 7.49 to 7.58 (1H, m), 7.81 (2H, d, J=9.2Hz) |
| 55 | 4-{3-[1-(3,4-ethylenedioxybenzyl)piperidin-4-yl]propanoyl}aniline (brown liquid) | 380 (M$^+$) | 1.24 to 1.38 (3H, m), 1.61 to 1.74 (4H, m), 1.83 to 1.97 (2H, m), 2.81 to 2.93 (4H, m), 3.37 (2H, s), 4.10 (2H, s, br), 4.24 (4H, s), 6.64 (2H, d, J=9.2Hz), 6.78 to 6.82 (3H, m), 7.80 (2H, d, J=9.2Hz) |
| 56 | 4-{3-[1-(2,3-dimethoxybenzyl)piperidin-4-yl]propanoyl}-aniline (brown liquid) | 382 (M$^+$) | 1.20 to 1.37 (3H, m), 1.62 to 1.74 (4H, m), 1.94 to 2.07 (2H, m), 2.82 to 2.97 (4H, m), 3.54 (2H, s), 4.82 (3H, s), 3.86 (3H, s), 4.12, (2H, s, br) 6.64 (2H, d, J=8.6Hz), 6.82 (1H, d, J=7.3Hz), 6.94 to 7.05 (2H, m), 7.80 (2H, d, J=8.6Hz) |

Reference Examples 57 to 66

In the same manner as in Reference examples 13, 14, 15 and 16, the following compounds were obtained.

| Reference example No. | Compound (characteristics) | Mass (m/z) | NMR (δ, (CDCl$_3$)) |
|---|---|---|---|
| 57 | N-trifluoroacetyl-4-[(1-benzyl-4-piperidinylidene)acetyl]aniline (pale yellow crystal) | 403 (M$^+$+1) | 2.39 to 2.49 (2H, m), 2.49 to 2.66 (4H, m), 2.87 to 3.00 (2H, m), 3.54 (2H, s), 6.63 (1H, s), 7.17 to 7.41 (5H, m), 7.69 (2H, d, J=8.5Hz), 7.97 (2H, d, J=8.5Hz), 8.38 (1H, br) |
| 58 | N-trifluoroacetyl-4-[(1-benzyl-piperidin-4-yl)-acetyl]aniline (pale yellow crystal) | 405 (M$^+$+1) | 1.25 to 1.47 (2H, m), 1.63 to 1.79 (2H, m), 1.87 to 2.08 (3H, m), 2.76 to 2.94 (4H, m), 3.49 (2H, s), 7.18 to 7.37 (5H, m), 7.70 (2H, d, J=9.1Hz), 7.97 (2H, d, J=9.1Hz) |
| 59 | N-acetyl-4-[(1-benzyl-4-hydroxy-piperidin-4-yl)-acetyl]-2-methoxyaniline (pale yellow crystal) | 397 (M$^+$+1) | 1.56 to 1.90 (4H, m), 2.23 (3H, s), 2.40 to 2.69 (4H, m), 3.09 (2H, s), 3.52 (2H, s), 3.96 (3H, s), 4.10 (1H, s), 6.93 (1H, d, J=8.5Hz), 7.17 to 7.40 (5H, m), 7.67 to 7.80 (2H, m), 8.99 (1H, d, J=2.4Hz) |
| 60 | N-acetyl-4-[(1-benzyl-4-piperidinylidene)acetyl]-2-methoxyaniline (yellow crystal) | 379 (M$^+$+1) | 2.22 (3H, s), 2.37 to 2.48 (2H, m), 2.48 to 2.65 (4H, m), 2.88 to 2.99 (2H, m), 3.53 (2H, s), 3.94 (3H, s), 6.65 (1H, s), 6.934 (1H, d, J=8.5Hz), 7.20 to 7.39 (5H, m), 7.67 to 7.80 (2H, m), 8.97 (1H, d, J=2.4Hz) |
| 61 | N-acetyl-4-[(1-benzylpiperidin-4-yl)acetyl]-2-methoxyaniline (yellowish brown liquid) | 381 (M$^+$+1) | 1.30 to 1.44 (2H, m), 1.60 to 1.78 (3H, m), 1.93 to 2.06 (2H, m), 2.22 (3H, s), 2.79 to 2.91 (4H, m), 3.49 (2H, s), 3.94 (3H, s), 6.92 (1H, d, J=8.8Hz), 7.20 to 7.36 (5H, m), 7.72 (1H, dd, J=8.8Hz, 2.0Hz), 7.76 (1H, s, br), 8.98 (1H, d, J=2.0Hz) |
| 62 | 4-[(1-benzyl-piperidin-4-yl)acetyl]-2-methoxyaniline.2HCl salt (pale brown crystal) | 339 (M$^+$+1) | (CDCl$_3$-DMSO-d$_6$) 1.66 to 1.72 (2H, m), 1.72 to 1.96 (2H, m), 2.09 to 2.23 (1H, m), 2.88 to 3.07 (4H, m), 3.29 to 3.40 (2H, m), 3.99 (3H, s), 4.27 (2H, d, J=4.9Hz), 7.20 (1H, d, J=8.8Hz), 7.39 to 7.46 (3H, m), 7.60 to 7.72 (2H, m), 7.92 (1H, dd, J=8.8Hz, 2.0Hz), 7.98 (1H, d, J=2.0Hz), 10.82 (1H, br) |
| 63 | N-acetyl-4-[(1-benzyl-4-hydroxy-piperidin-4-yl)-acetyl]-2-chloroaniline (pale brown liquid) | 382 (M$^+$ −18) | 1.58 to 1.87 (4H, m), 2.82 (3H, s), 2.40 to 2.71 (4H, m), 3.05 (2H, s), 3.52 (2H, s), 3.80 (1H, s), 7.20 to 7.36 (5H, m), 7.78 to 7.90 (2H, m), 7.98 (1H, d, J=1.8Hz), 8.56 (1H, d, J=9.1Hz) |
| 64 | Mixture of N-acetyl-4-[()1-benzyl-4-piperidinylidene-acetyl]-2-chloroaniline and N-acetyl-4-[(1-benzyl-1,2,5,6-tetrahydropyridin-4-yl)acetyl]-2-chloroaniline (pale brown liquid) | 383 (M$^+$+1) | 2.08 to 2.22, 2.40 to 2.65, 2.88 to 3.04 and 3.30 to 3.64 (total 10H), 2.28 (3H, s), 5.33 and 6.60 (total 1H), 7.17 to 7.39 (5H, m), 7.73 to 7.91 (2H, m), 7.96 to 8.03 (1H, m), 8.49 to 8.57 (1H, m) |
| 65 | N-acetyl-4-[(1-benzylpiperidin-4-yl)acetyl]-2-chloroaniline.HCl salt (pale yellow crystal) | 385 (M$^+$+1) | 1.81 to 2.03 (2H, m), 2.03 to 2.35 (3H, m), 2.28 (3H, s), 2.59 to 2.80 (2H, m), 2.88 to 2.99 (2H, m), 3.34 to 3.52 (2H, m), 4.14 (2H, s), 7.40 to 7.50 (3H, m), 7.57 to 7.68 (2H, m), 7.77 to 7.88 (2H, m), 7.95 (1H, d, J=1.8Hz), 8.55 (1H, d, J=9.1Hz) |
| 66 | 4-[(1-benzyl-piperidin-4-yl)acetyl]-2-chloroaniline.2HCl salt (pale | 343 (M$^+$+1) | (CDCl$_3$-DMSO-d$_6$) 1.82 to 2.00 (2H, m), 2.00 to 2.32 (3H, m), 2.61 to 2.90 (2H, m), 2.84 (2H, d, J=6.1Hz), 3.33 to 3.53 (2H, m), 4.15 (2H, d, J=4.9Hz), 6.89 (1H, d, |

-continued

| Reference example No. | Compound (characteristics) | Mass (m/z) | NMR (δ, (CDCl$_3$)) |
|---|---|---|---|
| | brown solid) | | J=8.6Hz), 7.35 to 7.52 (3H, m), 7.52 to 7.74 (3H, m), 7.83 (1H, d, J=2.4Hz), 12.22 (1H, br) |
| 67 | N-acetyl-4-[(1-benzyl-4-hydroxy-piperidin-4-yl)acetyl]-3-methoxyaniline (pale yellow liquid) | 397 (M$^+$+1) | 1.61 to 1.78 (4H, m), 2.24 (3H, s), 2.39 to 2.91 (4H, m), 3.08 (2H, s), 3.53 (2H, s), 3.81 (1H, s, br), 3.88 (3H, s), 6.60 (1H, dd, J=9.2Hz, 2.4Hz), 7.16 to 7.40 (5H, m), 7.80 (1H, d, J=9.2Hz), 8.43 (1H, d, J=2.4Hz), 11.95 (1H, s, br) |
| 68 | N-acetyl-4-[(1-benzylpiperidin-4-yl)acetyl]-3-methoxyaniline (pale yellow liquid) | 381 (M$^+$+1) | 1.27 to 1.46 (2H, m), 1.64 to 1.78 (2H, m), 1.83 to 2.09 (3H, m), 2.23 (3H, s), 2.75 to 2.94 (2H, m), 2.84 (2H, d, J=6.7Hz), 3.49 (2H, s), 3.87 (3H, s), 6.60 (1H, dd, J=9.2Hz, 2.4Hz), 7.13 to 7.40 (5H, m), 7.81 (1H, d, J=8.6Hz), 8.42 (1H, d, J=2.4Hz), 12.15 (1H, s, br) |
| 69 | 4-[(1-benzyl-piperidin-4-yl)acetyl]-3-methoxyaniline. 2HCl salt (reddish brown solid) | 339 (M$^+$+1) | (CDCl$_3$-DMSO-d$_6$) 1.84 to 2.33 (5H, m), 2.74 to 2.98 (2H, m), 2.87 (2H, d, J=6.1Hz), 3.31 to 3.50 (2H, m), 3.82 (3H, s), 4.21 (2H, d, J=4.9Hz), 6.38 (1H, dd, J=9.2Hz, 2.4Hz), 6.52 (1H, d, J=2.4Hz), 7.28 to 7.52 (3H, m), 7.52 to 7.83 (3H, m), 11.70 (1H, br) |

EFFECTS OF THE INVENTION

The compound having the formula (I) of the present invention has excellent selective inhibiting activities to both of acetylcholinesterase and A type monoamine oxidase, and is extremely useful as an antidepressant and an agent for curing senile dementia.

As an administration form for such purposes, there may be mentioned, for example, oral administration by a tablet, a capsule, a granule, a powder, syrup, etc. or parenteral administration by an intravenous injection, an intramuscular injection, a suppository, etc. The dose varies depending on age, body weight, symptoms, an administration form, an administration time, etc., but it is generally about 1 to 1,000 mg per day in one dose or divided doses to an adult.

Test example 1. Acetylcholinesterase-inhibiting activity

As an enzyme source, a crude synaptosome fraction of a rat cerebrum was used. The crude synaptosome fraction was prepared by homogenizing a rat cerebrum in a 0.32M sucrose solution and, after centrifugal operation, suspending it in a 0.1M phosphate buffer.

The activity of acetylcholinesterase was measured by a partially modified method of the method of Ellman et. al. (Ellman, G. L. et al., Biochem. Pharmacol., 7, 88 (1961)). That is, to the crude synaptosome fraction of the rat cerebrum suitably diluted with a 0.1M phosphate buffer were added each compound to be tested, 5,5'-dithiobis(2-nitrobenzoic acid) (hereinafter referred to as DTNB) and acetylthiocholine as a substrate, and the mixture was incubated at 25° C. for a predetermined time. Subsequently, the amount of yellow anions formed by reaction of acetylthiocholine and DTNB was measured as absorbance at 410 nm to determine the activity of acetylcholinesterase.

Enzyme activity-inhibiting rates were calculated from absorbances in the presence of the compounds to be tested having various concentrations based on absorbances in the absence of the compounds to be tested, with absorbance when reaction was carried out in the absence of the substrate being defined as blank. IC$_{50}$ values were calculated by Hill analysis.

Test example 2. Butyrylcholinesterase-inhibiting activity

As an enzyme source, a rat serum was used.

The activity of butyrylcholinesterase was measured by a partially modified method of the above method of Ellman et. al. That is, to the rat serum suitably diluted with a 0.1M phosphate buffer were added each compound to be tested, DTNB and butyrylthiocholine as a substrate, and the mixture was incubated at 25° C. for a predetermined time. Subsequently, the amount of yellow anions formed by reaction of butyrylthiocholine and DTNB was measured as absorbance at 410 nm to determine the activity of butyrylcholinesterase.

Enzyme activity-inhibiting rates were calculated from absorbances in the presence of the compounds to be tested having various concentrations based on absorbances in the absence of the compounds to be tested, with absorbance when reaction was carried out in the absence of the substrate being defined as blank. IC$_{50}$ values were calculated by Hill analysis.

Test example 3. A type and B type monoamine oxidase-inhibiting activity

As an enzyme source, a rat cerebrum homogenized in a 0.1M phosphate buffer was used.

The activities of monoamine oxidases were measured by a partially modified method of the method of Da Prada et al. (Da Prada, M. et al., J. Pharmacol. Exp. Ther., 248 (1), 400

(1989)). That is, the rat cerebrum homogenate suitably diluted with a 0.1M phosphate buffer and each compound to be tested were preincubated at 37° C. for 30 minutes. Then, a substrate labeled with $^{14}$C (5-hydroxy-tryptamine (5-HT) having a final concentration of 200 µM was used in measurement of the activity of A type monoamine oxidase, and β-phenylethylamine (β-PEA) having a final concentration of 20 µM was used in measurement of the activity of B type monoamine oxidase) was added to the preincubated mixture, and the mixture was incubated at 37° C. for a predetermined time. After the reaction was terminated by adding hydrochloric acid (final concentration; 1.2M), the reaction mixture and a predetermined amount of an organic solvent (diethyl ether was used in measurement of the activity of A type monoamine oxidase, and heptane was used in measurement of the activity of B type monoamine oxidase) were vigorously stirred so that deaminated metabolites were extracted into the organic layer. After the mixture was separated into two layers by centrifugation, a part of the organic layer was mixed with liquid scintillation cocktail. Radioactivity extracted into the organic layer was measured by a liquid scintillation counter to calculate the enzyme activity.

Inhibiting rates were calculated from enzyme activities in the presence of the compounds to be tested having various concentrations based on enzyme activities in the absence of the compounds to be tested, with absorbance when reaction was carried out in the absence of the homogenate being defined as blank. IC$_{50}$ values were calculated by Hill analysis.

The results of Test examples 1 to 3 are shown in Table 3.

TABLE 3

| Compound to be tested | IC$_{50}$ value (M) | | | |
|---|---|---|---|---|
| | Inhibition of acetylcholinesterase | Inhibition of butyrylcholinesterase | Inhibition of A type monoamine oxidase | Inhibition of B type monoamine oxidase |
| Compound of Example 1 | $3.3 \times 10^{-9}$ | $>10^{-5}$ | $1.6 \times 10^{-6}$ | $>10^{-5}$ |
| Compound of Example 2 | $3.6 \times 10^{-9}$ | $>10^{-5}$ | $8.9 \times 10^{-7}$ | $>10^{-5}$ |
| Compound of Example 6 | $3.1 \times 10^{-9}$ | $>10^{-5}$ | $2.2 \times 10^{-7}$ | $>10^{-5}$ |
| Compound of Example 8 | $2.0 \times 10^{-9}$ | $>10^{-5}$ | $8.5 \times 10^{-8}$ | $>10^{-5}$ |
| Compound of Example 9 | $1.4 \times 10^{-9}$ | $>10^{-5}$ | $1.4 \times 10^{-6}$ | $>10^{-5}$ |
| Compound of Example 10 | $1.1 \times 10^{-9}$ | $>10^{-5}$ | $3.2 \times 10^{-7}$ | $>10^{-5}$ |
| Compound of Example 21 | $2.0 \times 10^{-8}$ | $>10^{-5}$ | $6.0 \times 10^{-7}$ | $>10^{-5}$ |
| Compound of Example 22 | $7.3 \times 10^{-9}$ | $>10^{-5}$ | $8.1 \times 10^{-7}$ | $>10^{-5}$ |
| Compound of Example 25 | $2.5 \times 10^{-7}$ | $>10^{-5}$ | $3.4 \times 10^{-7}$ | $6.8 \times 10^{-6}$ |
| Compound of Example 26 | $1.5 \times 10^{-7}$ | $>10^{-5}$ | $5.6 \times 10^{-8}$ | $>10^{-5}$ |
| Compound of Example 53 | $1.7 \times 10^{-8}$ | $>10^{-5}$ | $8.5 \times 10^{-8}$ | $>10^{-5}$ |
| Compound of Example 87 | $2.7 \times 10^{-7}$ | $>10^{-5}$ | $3.5 \times 10^{-8}$ | $>10^{-5}$ |
| Compound of Example 88 | $3.3 \times 10^{-7}$ | $>10^{-5}$ | $2.5 \times 10^{-7}$ | $2.1 \times 10^{-6}$ |
| Compound of Example 93 | $2.0 \times 10^{-7}$ | $>10^{-5}$ | $4.2 \times 10^{-7}$ | $7.2 \times 10^{-6}$ |
| Compound A | $7.3 \times 10^{-9}$ | $3.9 \times 10^{-6}$ | $>10^{-5}$ | $>10^{-5}$ |
| Compound B | $>10^{-5}$ | $>10^{-5}$ | $1.6 \times 10^{-7}$ | $>10^{-5}$ |

Compound A: 1-benzyl-4-[(5,6-dimethoxy-1-indanon)-2-yl]methylpiperidine
Compound B: 4-(4-cyanoanilino)-5,6-dihydro-7H-cyclopenta-[d]pyrimidine

We claim:
1. A pyrimidine compound of the formula (I):

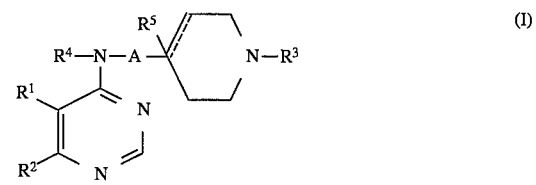

wherein R$^1$ and R$^2$ each represent a hydrogen atom, a halogen atom, an amino group, a nitro group, an alkyl group, a lower alkoxy group or a lower alkoxycarbonyl group, or R$^1$ and R$^2$ are bonded together to form a C$_{3-6}$ alkylene group, and said alkyl group and alkylene group being unsubstituted or substituted by a halogen, hydroxy, a lower alkoxy, a lower alkenyloxy, an aryloxy, an aralkyloxy or an acyloxy.

R$^3$ represents an aralkyl group or a C$_1$–C$_4$ alkyl group substituted by a hetero aromatic ring, the hetero aromatic ring comprising a 5- or 6-membered aromatic heteromonocyclic group having one or two hetero atoms selected from the group consisting of nitrogen, oxygen and sulfur, or a fused aromatic group comprising a benzene ring fused with said 5- or 6-membered aromatic heteromonocyclic group, and the aryl portion of said aralkyl group and said $C_1$–$C_4$ alkyl group being unsubstituted or substituted by a halogen, amino, alkanoylamino, cyano, nitro, hydroxy, a lower alkyl, a lower alkoxy, an aralkyloxy, an alkylenedioxy, a halogeno-lower alkyl or a halogeno-lower alkoxy, $R^4$ represents a hydrogen atom or an acyl group, $R^5$ represents a hydrogen atom, a hydroxy group or a lower alkoxy group, A represents

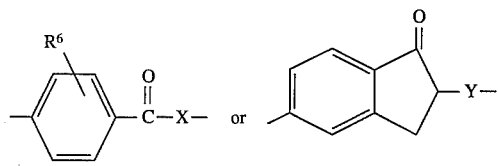

where $R^6$ represents a hydrogen atom, a halogen atom, a lower alkyl group or a lower alkoxy group, X represents —CH=, —CH=CH—$(CH_2)_p$—, —$CH_2$— or —$CH_2CH_2$—$(CH_2)_p$—, Y represents =CH—$(CH_2)_p$—, —$CH_2$—$(CH_2)_p$—, a single bond or a double bond and p represents 0 or 1, $\overline{...}$ represents a single bond or a double bond, and when $\overline{...}$ represents a double bond or X represents —CH=, or Y represents a double bond, $R^5$ does not exist, and a salt thereof.

2. The pyrimidine compound and a salt thereof according to claim 1 which is represented by the formula (II):

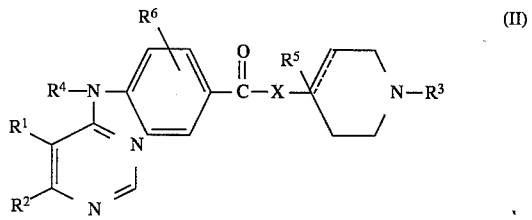

wherein $R^1$, $R^2$, $R^3$, $R^4$, $R^5$, $R^6$, X and $\overline{...}$ have the same meanings as defined above in claim 1.

3. The pyrimidine compound and a salt thereof according to claim 1 or 2, wherein $R^1$ and $R^2$ are bonded together to form a $C_{3-6}$ straight or branched alkylene group.

4. The pyrimidine compound and a salt thereof according to claim 3, wherein the alkylene group formed by bonding $R^1$ and $R^2$ together is a trimethylene group or a tetramethylene group.

5. The pyrimidine compound and a salt thereof according to claim 1, or 2, wherein $R^1$ and $R^2$ are the same or different and each represent a hydrogen atom, a fluorine atom, a chlorine atom, a bromine atom or a $C_{1-7}$ straight or branched alkyl group.

6. The pyrimidine compound and a salt thereof according to claim 5, wherein one of $R^1$ and $R^2$ is a $C_{1-4}$ alkyl group and the other is a hydrogen atom, a chlorine atom or a $C_{1-4}$ alkyl group.

7. The pyrimidine compound and a salt thereof according to claim 6, wherein $R^1$ is a $C_{1-4}$ alkyl group and $R^2$ is a hydrogen atom or a $C_{1-4}$ alkyl group.

8. The pyrimidine compound and a salt thereof according to claim 1 or 2, wherein $R^3$ is a benzyl group, a sec-phenethyl group, a fluorobenzyl group, a chlorobenzyl group, a methoxybenzyl group, a cyanobenzyl group, a nitrobenzyl group, a 2-thienylmethyl group, a 2-furylmethyl group, a 2-pyridylmethyl group or a 6-methyl-2-pyridylmethyl group.

9. The pyrimidine compound and a salt thereof according to claim 8, wherein $R^3$ is a benzyl group.

10. The pyrimidine compound and a salt thereof according to claim 1 or 2, wherein $R^4$ is a hydrogen atom or an acetyl group.

11. The pyrimidine compound and a salt thereof according to claim 1 or 2, wherein $R^5$ is a hydrogen atom.

12. The pyrimidine compound and a salt thereof according to claim 2, wherein $R^6$ is a hydrogen atom, a chlorine atom, a fluorine atom or a methoxy group.

13. The pyrimidine compound and a salt thereof according to claim 2, wherein all of $R^4$, $R^5$ and $R^6$ are hydrogen atoms.

14. The pyrimidine compound and a salt thereof according to claim 2, wherein X is —$CH_2$—, —$CH_2CH_2$— or —CH=CH— and $\overline{...}$ is a single bond.

15. The pyrimidine compound and a salt thereof according to claim 2, which is selected from the group consisting of (E)-N-(5,6-dimethylpyrimidin-4-yl)-4-[3-(1-benzylpiperidin-4-yl)propenoyl]aniline, (E)-N-(5,6-dihydro-7H-cyclopenta[d]pyrimidin-4-yl)-4-[3-(1-benzylpiperidin-4-yl)propenoyl]aniline, N-(5,6,7,8-tetrahydroquinazolin-4-yl)-4-[3-(1-benzyl-piperidin-4-yl)propanoyl]aniline, N-(5,6-dihydro-7H-cyclopenta[d]pyrimidin-4-([1-(2-thienylmethyl)piperidin-4-yl]acetyl)aniline, N-(5-methylpyrimidin-4-yl)-4-{[1-(2-thienylmethyl)-piperidin-4-yl]acetyl}aniline and N-(5-ethylpyrimidin-4-yl)-4-[(1-benzylpiperidin-4-yl)acetyl]aniline.

16. The pyrimidine compound and a salt thereof according to claim 2, wherein said compound is N-(5,6-dimethylpyrimidin-4-yl)-4-[3-(1-benzylpiperidin-4-yl)propanoyl]aniline.

17. The pyrimidine compound and a salt thereof according to claim 2, wherein said compound is N-(5,6-dihydro-7H-cyclopenta[d]pyrimidin-4-yl)-4-[3-(1-benzylpiperidin-4-yl)propanoyl]aniline.

18. The pyrimidine compound and a salt thereof according to claim 2, wherein said compound is N-(5-methylpyrimidin-4-yl)-4[(1-benzylpiperidin-4-yl)acetyl]aniline.

19. The pyrimidine compound and a salt thereof according to claim 2, wherein said compound is N-(5,6-dihydro-7H-cyclopenta[d]pyrimidin-4-yl)-4-[(1-benzylpiperidin-4-yl)acetyl]aniline.

20. The pyrimidine compound and a salt thereof according to claim 2, wherein said compound is N-(5,6-dihydro-7H-cyclopenta[d]pyrimidin-4-{3-[1-(2-pyridylmethyl)piperidin-4-yl]propanoyl}aniline.

21. The pyrimidine compound and a salt thereof according to claim 16, wherein $R^1$ and $R^2$ each represent a hydrogen atom, a halogen atom, an amino group, a nitro group, a $C_1$–$C_{10}$ alkyl group, a $C_1$–$C_4$ alkoxy group or a $C_2$–$C_5$ alkoxycarbonyl group or $R^1$ and $R^2$ are bonded together to form a $C_3$–$C_6$ alkylene group, and said $C_1$–$C_{10}$ alkyl group and said $C_3$–$C_6$ alkylene group being unsubstituted or substituted by a halogen, hydroxy, $C_1$–$C_4$ alkoxy, $C_3-C_4$ alkenyloxy, phenoxy, naphthoxy, benzyloxy, phenethyloxy, $C_7-C_8$ aralkyloxy or $C_1-C_{10}$ aliphatic acyloxy, $R^3$ represents an aryl $C_1-C_4$ alkyl group or a $C_1-C_4$ alkyl group substituted by a hetero aromatic ring, the hetero aromatic ring comprising a 5- or 6-membered hetermonocyclic group having one or two hetero atoms selected from the group consisting of nitrogen, oxygen and sulfur, or a fused aromatic group comprising a benzene ring fused with said 5- or 6-membered aromatic heteromonocyclic group, and the aryl portion of said aryl $C_1-C_4$ alkyl group and said $C_1-C_4$ alkyl group which is substituted by said hetero aromatic ring being unsubstituted or substituted by a halogen, amino, $C_1-C_4$ alkanoylamino, cyano, nitro, hydroxy, $C_1-C_4$ alkyl, $C_1-C_4$ alkoxy, benzyloxy, phenethyloxy, naphthylmethoxy, $C_7-C_{11}$ aralkyloxy, $C_1-C_2$ alkylenedioxy, a halogeno-$C_1-C_4$ alkyl or a halogeno-$C_1-C_4$ alkoxy, $R^4$ represents a hydrogen atom or a $C_1-C_{10}$ aliphatic acyl group, $R^5$ represents a hydrogen atom, a hydroxy group or a $C_1-C_4$ alkoxy group, and $R^6$ represents a hydrogen atom, a halogen atom, a $C_1-C_4$ alkyl group or a $C_1-C_4$ alkoxy group.

* * * * *

UNITED STATES PATENT AND TRADEMARK OFFICE
CERTIFICATE OF CORRECTION

PATENT NO. : 5,610,303
DATED : March 11, 1997
INVENTOR(S) : KIMURA et al

It is certified that error appears in the above-identified patent and that said Letters Patent is hereby corrected as shown below:

```
Column 122, line 60 (Claim 21):  after "claim"
     delete "16" and insert --1--.
```

Signed and Sealed this

Eighth Day of December, 1998

Attest:

BRUCE LEHMAN

Attesting Officer

Commissioner of Patents and Trademarks